US012797415B2

(12) United States Patent
Kwong et al.

(10) Patent No.: US 12,797,415 B2
(45) Date of Patent: Nov. 17, 2026

(54) SYNTHETIC ANTIGENS AS CHIMERIC ANTIGEN RECEPTOR (CAR) LIGANDS AND USES THEREOF

(71) Applicant: Georgia Tech Research Corporation, Atlanta, GA (US)

(72) Inventors: Gabriel Kwong, Atlanta, GA (US); Marielena Gamboa, Atlanta, GA (US); Ali Zamat, Atlanta, GA (US); Ji-Ho Park, Atlanta, GA (US); Heegon Kim, Atlanta, GA (US); Phillip J. Santangelo, Atlanta, GA (US); Daryll A. Vanover, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 749 days.

(21) Appl. No.: 18/032,012

(22) PCT Filed: Oct. 14, 2021

(86) PCT No.: PCT/US2021/054972
§ 371 (c)(1),
(2) Date: Apr. 14, 2023

(87) PCT Pub. No.: WO2022/081838
PCT Pub. Date: Apr. 21, 2022

(65) Prior Publication Data

US 2023/0390335 A1 Dec. 7, 2023

Related U.S. Application Data

(60) Provisional application No. 63/091,884, filed on Oct. 14, 2020.

(51) Int. Cl.

| | |
|---|---|
| ***A61K 35/17*** | (2025.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 16/11*** | (2026.01) |
| ***C12N 5/0783*** | (2010.01) |

(52) U.S. Cl.
CPC .............. *A61K 35/17* (2013.01); *A61K 40/11* (2025.01); *A61K 40/31* (2025.01); *A61K 40/421* (2025.01); *A61P 35/00* (2018.01); *C07K 16/11* (2026.01); *C12N 5/0636* (2013.01); *A61K 2239/13* (2023.05); *A61K 2239/31* (2023.05); *A61K 2239/38* (2023.05); *A61K 2239/49* (2023.05); *A61K 2239/50* (2023.05)

(58) Field of Classification Search
None
See application file for complete search history.

(56) References Cited

U.S. PATENT DOCUMENTS

| | | | |
|---|---|---|---|
| 4,342,566 | A | 8/1982 | Theofilopoulos et al. |
| 4,816,567 | A | 3/1989 | Cabilly et al. |
| 4,897,355 | A | 1/1990 | Eppstein et al. |
| 5,565,332 | A | 10/1996 | Hoogenboom et al. |
| 5,721,367 | A | 2/1998 | Kay et al. |
| 5,804,440 | A | 9/1998 | Burton et al. |
| 5,837,243 | A | 11/1998 | Deo et al. |
| 5,939,598 | A | 8/1999 | Kucherlapati et al. |
| 6,096,441 | A | 8/2000 | Hauser et al. |
| 6,130,364 | A | 10/2000 | Jakobovits et al. |
| 6,180,377 | B1 | 1/2001 | Morgan et al. |
| 6,261,834 | B1 | 7/2001 | Srivastava |
| 2009/0280567 | A1 | 11/2009 | Leake et al. |
| 2013/0287752 | A1 | 10/2013 | Davila et al. |
| 2016/0228573 | A1 | 8/2016 | Niyikiza et al. |
| 2017/0219596 | A1 | 8/2017 | Tanenbaum et al. |
| 2020/0230221 | A1 | 7/2020 | Irvine et al. |

FOREIGN PATENT DOCUMENTS

| | | | | |
|---|---|---|---|---|
| WO | 1994/029348 | | 12/1994 | |
| WO | WO-2016203052 | A1 * | 12/2016 | ............. A61K 39/12 |
| WO | 2019036724 | A2 | 2/2019 | |
| WO | 2020/185917 | A1 | 9/2020 | |
| WO | WO-2021108050 | A2 * | 6/2021 | ......... C12N 15/1136 |
| WO | WO-2021234694 | A1 * | 11/2021 | .............. A61P 35/00 |

OTHER PUBLICATIONS

Sela-Culang et al. The structural basis of antibody-antigen recognition. Fron. Immuno., vol. 4, Article 302, Oct. 2013. (Year: 2013).*
Bever et al. VHH antibodies: emerging reagents for the analysis of environmental chemicals. Anal Bioanal Chem (2016) 408:5985-6002. (Year: 2016).*
Detalle et al. Generation and Characterization of ALX-0171, a Potent Novel therapeutic nanobody for the treatment of respiratory syncytial virus infection. Antimicrobial Agnets and Chemotherapy. Jan. 2016, vol. 60, No. 1. (Year: 2016).*
Herold et al. Determinants of the assembly and function of antibody variable domains. Nature Scientific Reports, 7:12276, Sep. 25, 2017. (Year: 2017).*
SynAbs. Secondary Monoclonal Antibodies, Innovative anti-VHH antibodies: SYnAbs enters the nano-world. Jun. 10, 2019. (Year: 2019).*
Hacisuleyman and Erman. ModiBodies: A computational method for modifying nanobodies in nanobody-antigen complexes to improve binding affinity and specificity. Journal of Biological Physics (2020), May 2020, 46:189-208 (Year: 2020).*
Acsadi, Gyula, et al. "Human dystrophin expression in mdx mice after intramuscular injection of DNA constructs." Nature 352.6338 (1991): 815-818.

(Continued)

*Primary Examiner* — Gary B Nickol
*Assistant Examiner* — Amy M. Chattin
(74) *Attorney, Agent, or Firm* — Meunier Carlin & Curfman LLC

(57) ABSTRACT

Disclosed are synthetic antigen chimeric antigen receptor systems and methods of their use for the treatment of cancer.

22 Claims, 23 Drawing Sheets

Specification includes a Sequence Listing.

(56) References Cited

OTHER PUBLICATIONS

Bagshawe, K. D. "Towards generating cytotoxic agents at cancer sites. The First Bagshawe Lecture." Br. J. Cancer 60 (1989): 275-281.
Bagshawe, K. D., et al. "A cytotoxic agent can be generated selectively at cancer sites." British journal of cancer 58.6 (1988): 700-703.
Battelli, M. G., et al. "T lymphocyte killing by a xanthine-oxidase-containing immunotoxin." Cancer Immunology, Immunotherapy 35.6 (1992): 421-425.
Berkner, Kathleen L., et al. "Abundant expression of polyomavirus middle T antigen and dihydrofolate reductase in an adenovirus recombinant." Journal of virology 61.4 (1987): 1213-1220.
Bout, Abraham, et al. "Lung gene therapy: in vivo adenovirus-mediated gene transfer to rhesus monkey airway epithelium." Human Gene Therapy 5.1 (1994): 3-10.
Brigham, Kenneth L., et al. "Expression of a prokaryotic gene in cultured lung endothelial cells after lipofection with a plasmid vector." Am J Respir Cell Mol Biol 1.2 (1989): 95-100.
Brown, Dennis T., and Byron T. Burlingham. "Penetration of host cell membranes by adenovirus 2." Journal of Virology 12.2 (1973): 386-396.
Brown, Valerie I., and Mark I. Greene. "Molecular and cellular mechanisms of receptor-mediated endocytosis." DNA and cell biology 10.6 (1991): 399-409.
Brüggemann, Marianne, N. P. Davies, and I. R. Rosewell. "Designer mice: the production of human antibody repertoires in transgenic animals." The Year in immunology 7 (1993): 33-40.
Caillaud, Catherine, et al. "Adenoviral vector as a gene delivery system into cultured rat neuronal and glial cells." European Journal of Neuroscience 5.10 (1993): 1287-1291.
Chardonnet, Yvette, and Samuel Dales. "Early events in the interaction of adenoviruses with Hela cells: I. Penetration of type 5 and intracellular release of the DNA genome." Virology 40.3 (1970): 462-477.
Cotter, Murray A., and E. S. Robertson. "Molecular genetic analysis of herpesviruses and their potential use as vectors for gene therapy applications." Current Opinion in Molecular Therapeutics 1.5 (1999): 633-644.
Davidson, Dominique, and John A. Hassell. "Overproduction of polyomavirus middle T antigen in mammalian cells through the use of an adenovirus vector." Journal of virology 61.4 (1987): 1226-1239.
Felgner, Philip L., et al. "Lipofection: a highly efficient, lipid-mediated DNA-transfection procedure." Proceedings of the National Academy of Sciences 84.21 (1987): 7413-7417.
Gomez-Foix, Anna M., et al. "Adenovirus-mediated transfer of the muscle glycogen phosphorylase gene into hepatocytes confers altered regulation of glycogen metabolism." Journal of Biological Chemistry 267.35 (1992): 25129-25134.
Guzman, Raul J., et al. "Efficient gene transfer into myocardium by direct injection of adenovirus vectors." Circulation Research 73.6 (1993): 1202-1207.
Haj-Ahmad, Yousef, and Frank L. Graham. "Development of a helper-independent human adenovirus vector and its use in the transfer of the herpes simplex virus thymidine kinase gene." Journal of Virology 57.1 (1986): 267-274.
Handbook of Monoclonal Antibodies, Ferrone et al., eds., Noges Publications, Park Ridge, N.J., (1985) ch. 22 and pp. 303-357.
Hughes, Brenda J., et al. "Monoclonal antibody targeting of liposomes to mouse lung in vivo." Cancer research 49.22 (1989): 6214-6220.
Jakobovits, Aya, et al. "Analysis of homozygous mutant chimeric mice: deletion of the immunoglobulin heavy-chain joining region blocks B-cell development and antibody production." Proceedings of the National Academy of Sciences 90.6 (1993): 2551-2555.
Jakobovits, Aya, et al. "Germ-line transmission and expression of a human-derived yeast artificial chromosome." Nature 362.6417 (1993): 255-258.
Jones, Peter T., et al. "Replacing the complementarity-determining regions in a human antibody with those from a mouse." Nature 321.6069 (1986): 522-525.
Kirshenbaum, Lorrie A., et al. "Highly efficient gene transfer into adult ventricular myocytes by recombinant adenovirus." The Journal of clinical investigation 92.1 (1993): 381-387.
Köhler, Georges, and Cesar Milstein. "Continuous cultures of fused cells secreting antibody of predefined specificity." nature 256.5517 (1975): 495-497.
La Salle, G. Le Gal, et al. "An adenovirus vector for gene transfer into neurons and glia in the brain." Science 259.5097 (1993): 988-990.
Litzinger, David C, and Leaf Huang. "Biodistribution and immunotargetability of ganglioside-stabilized dioleoylphosphatidylethanolamine liposomes." Biochimica et Biophysica Acta (BBA)-Biomembranes 1104.1 (1992): 179-187.
Massie, Bernard, Yakov Gluzman, and John A. Hassell. "Construction of a helper-free recombinant adenovirus that expresses polyomavirus large T antigen." Molecular and cellular biology (1986), 6:2872-2883 (1986).
Morsy, Manal A., et al. "Efficient adenoviral-mediated ornithine transcarbamylase expression in deficient mouse and human hepatocytes." The Journal of clinical investigation 92.3 (1993): 1580-1586.
Moullier, Philippe, et al. "Correction of lysosomal storage in the liver and spleen of MPS VII mice by implantation of genetically modified skin fibroblasts." Nature genetics 4.2 (1993): 154-159.
Pietersz, Geoffrey A., and Ian FC McKenzie. "Antibody conjugates for the treatment of cancer." Immunological reviews 129.1 (1992): 57-80.
Presta, Leonard G. "Antibody engineering." Current Opinion in Structural Biology 2.4 (1992): 593-596.
Ragot, T., et al. "Replication-defective recombinant adenovirus expressing the Epstein-Barr virus (EBV) envelope glycoprotein gp340/220 induces protective immunity against EBV-induced lymphomas in the cottontop tamarin." Journal of General Virology 74.3 (1993): 501-507.
Ram, Zvi, et al. "In situ retroviral-mediated gene transfer for the treatment of brain tumors in rats." Cancer research 53.1 (1993): 83-88.
Rich, Devra P., et al. "Development and analysis of recombinant adenoviruses for gene therapy of cystic fibrosis." Human Gene Therapy 4.4 (1993): 461-476.
Riechmann, Lutz, et al. "Reshaping human antibodies for therapy." Nature 332.6162 (1988): 323-327.
Roessler, Blake J., et al. "Adenoviral-mediated gene transfer to rabbit synovium in vivo." The Journal of clinical investigation 92.2 (1993): 1085-1092.
Roffler, Steven R., et al. "Anti-neoplastic glucuronide prodrug treatment of human tumor cells targeted with a monoclonal antibody-enzyme conjugate." Biochemical pharmacology 42.10 (1991): 2062-2065.
Senter, Peter D., et al. "Generation of 5-fluorouracil from 5-fluorocytosine by monoclonal antibody-cytosine deaminase conjugates." Bioconjugate chemistry 2.6 (1991): 447-451.
Senter, Peter D., et al. "Generation of cytotoxic agents by targeted enzymes." Bioconjugate chemistry 4.1 (1993): 3-9.
Seth, Prem, et al. "Evidence that the penton base of adenovirus is involved in potentiation of toxicity of Pseudomonas exotoxin conjugated to epidermal growth factor." Molecular and Cellular Biology (1984).
Seth, Prem, et al. "Role of a low-pH environment in adenovirus enhancement of the toxicity of a Pseudomonas exotoxin-epidermal growth factor conjugate." Journal of virology 51.3 (1984): 650-655.
Smith et al., Antibodies in Human Diagnosis and Therapy, Haber et al., eds., Raven Press, New York (1977) pp. 365-389.
Sun, Tian-Qiang, David A. Fenstermacher, and Jean-Michel H. Vos. "Human artificial episomal chromosomes for cloning large DNA fragments in human cells." Nature genetics 8.1 (1994): 33-41.
Svensson, Ulla. "Role of vesicles during adenovirus 2 internalization into HeLa cells." Journal of virology 55.2 (1985): 442-449.
Varga, Mikael J., C. L. A. E. S. Weibull, and E. I. N. A. R. Everitt. "Infectious entry pathway of adenovirus type 2." Journal of virology 65.11 (1991): 6061-6070.

(56) References Cited

OTHER PUBLICATIONS

Verhoeyen, Martine, Cesar Milstein, and Greg Winter. "Reshaping human antibodies: grafting an antilysozyme activity." Science 239. 4847 (1988): 1534-1536.
Wickham, Thomas J., et al. "Integrins αvβ3 and αvβ5 promote adenovirus internalization but not virus attachment." Cell 73.2 (1993): 309-319.
Wolff, Jon A., et al. "Direct gene transfer into mouse muscle in vivo." Science 247.4949 (1990): 1465-1468.
Zabner, Joseph, et al. "Adenovirus-mediated gene transfer transiently corrects the chloride transport defect in nasal epithelia of patients with cystic fibrosis." Cell 75.2 (1993): 207-216.
Zabner, Joseph, et al. "Safety and efficacy of repetitive adenovirus-mediated transfer of CFTR cDNA to airway epithelia of primates and cotton rats." Nature genetics 6.1 (1994): 75-83.
Zhang "Generation and identification of recombinant adenovirus by liposome-mediated transfection and PCR analysis" BioTechniques 15:868-872 (1993).
Zoller, Mark J. "New recombinant DNA methodology for protein engineering." Current opinion in biotechnology 3.4 (1992): 348-354.
Extended European Search Report received in corresponding Application No. 21881082.8, dated Jan. 23, 2025.
Gamboa Lena et al: "Sensitizing solid tumors to CAR T cell-mediated cytotoxicity using synthetic antigens", , Dec. 19, 2024 (Dec. 19, 2024), XP093235752, Retrieved from the Internet: URL:https://submissions.mirasmart.com/SecureView/BMESArchive/rad21 oedlol.pdf [retrieved on Dec. 19, 2024].
International Search Report and Written Opinion received in PCT/US2021/054972 dated Jan. 14, 202.

* cited by examiner

FIG. 14A, FIG. 14B, FIG. 14C, FIG. 14D, and FIG. 14E

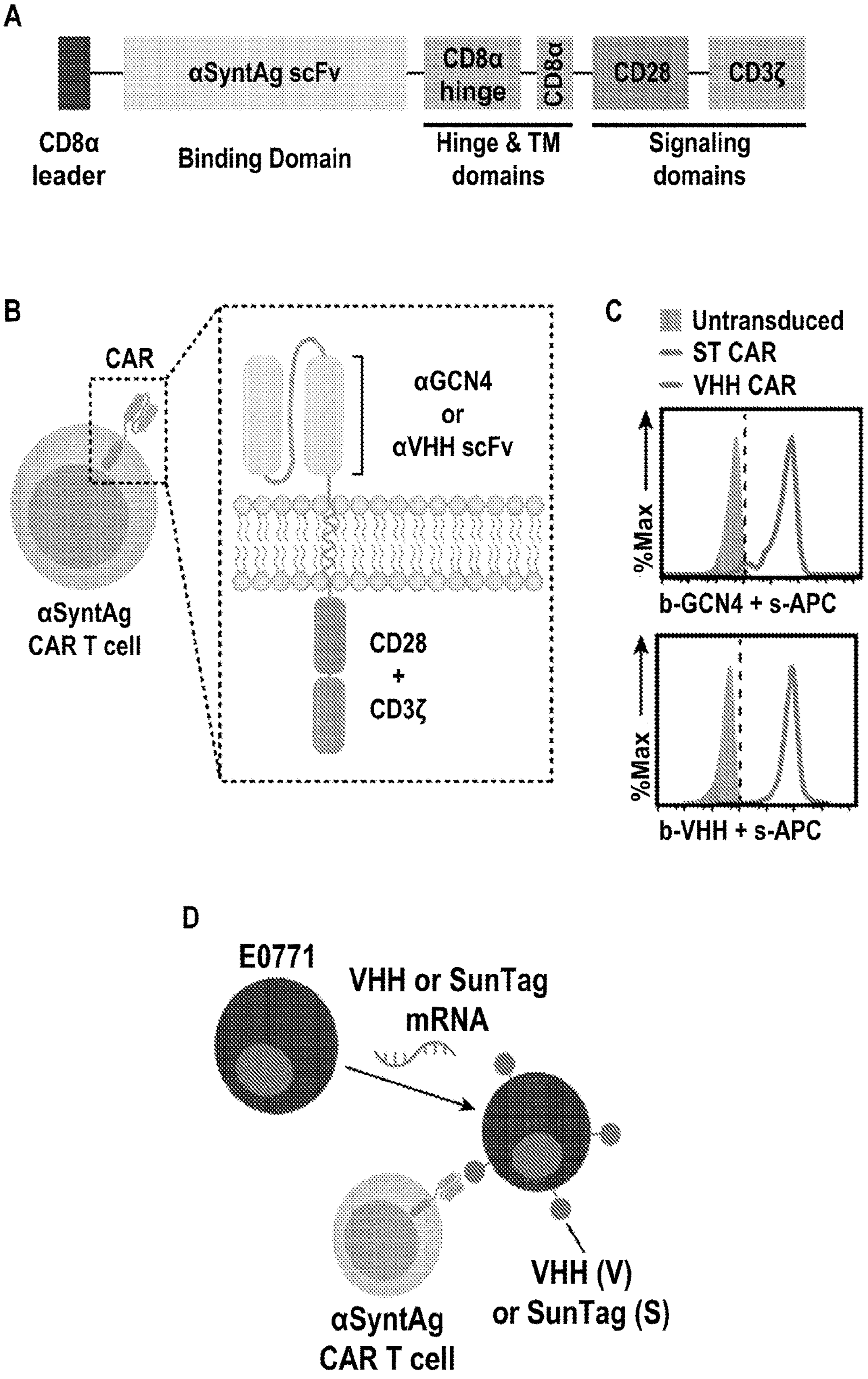
FIG. 16A, FIG. 16B, FIG. 16C, and FIG. 16D

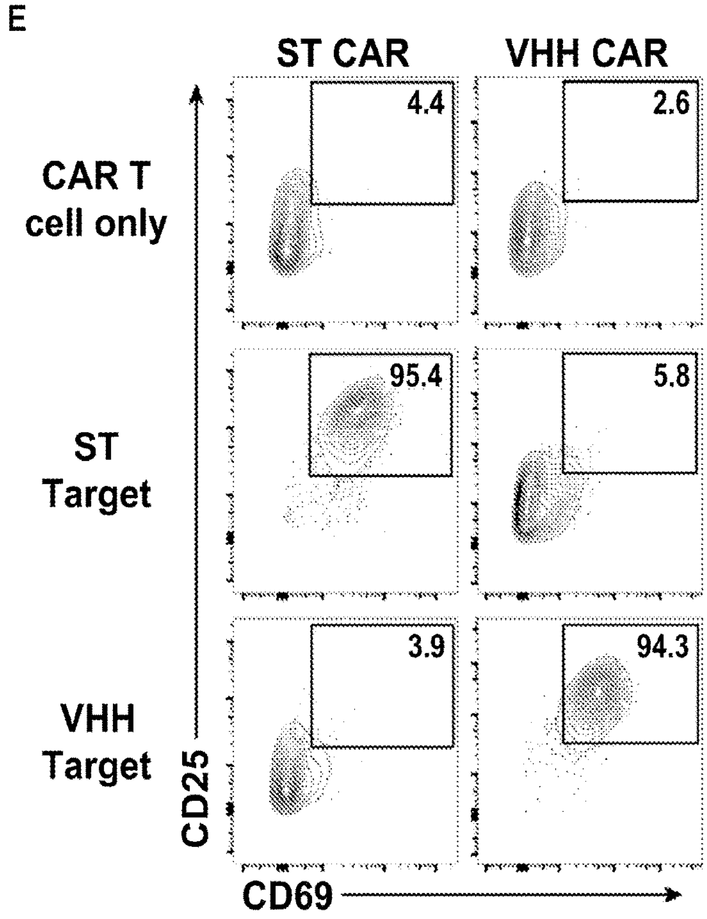
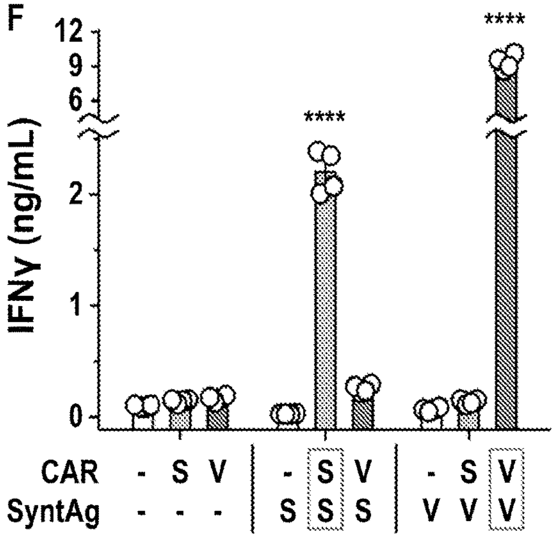
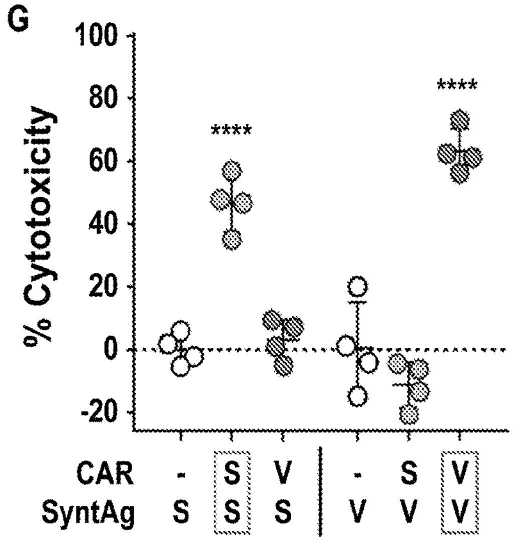
FIG. 16E, FIG. 16F, and FIG. 16G

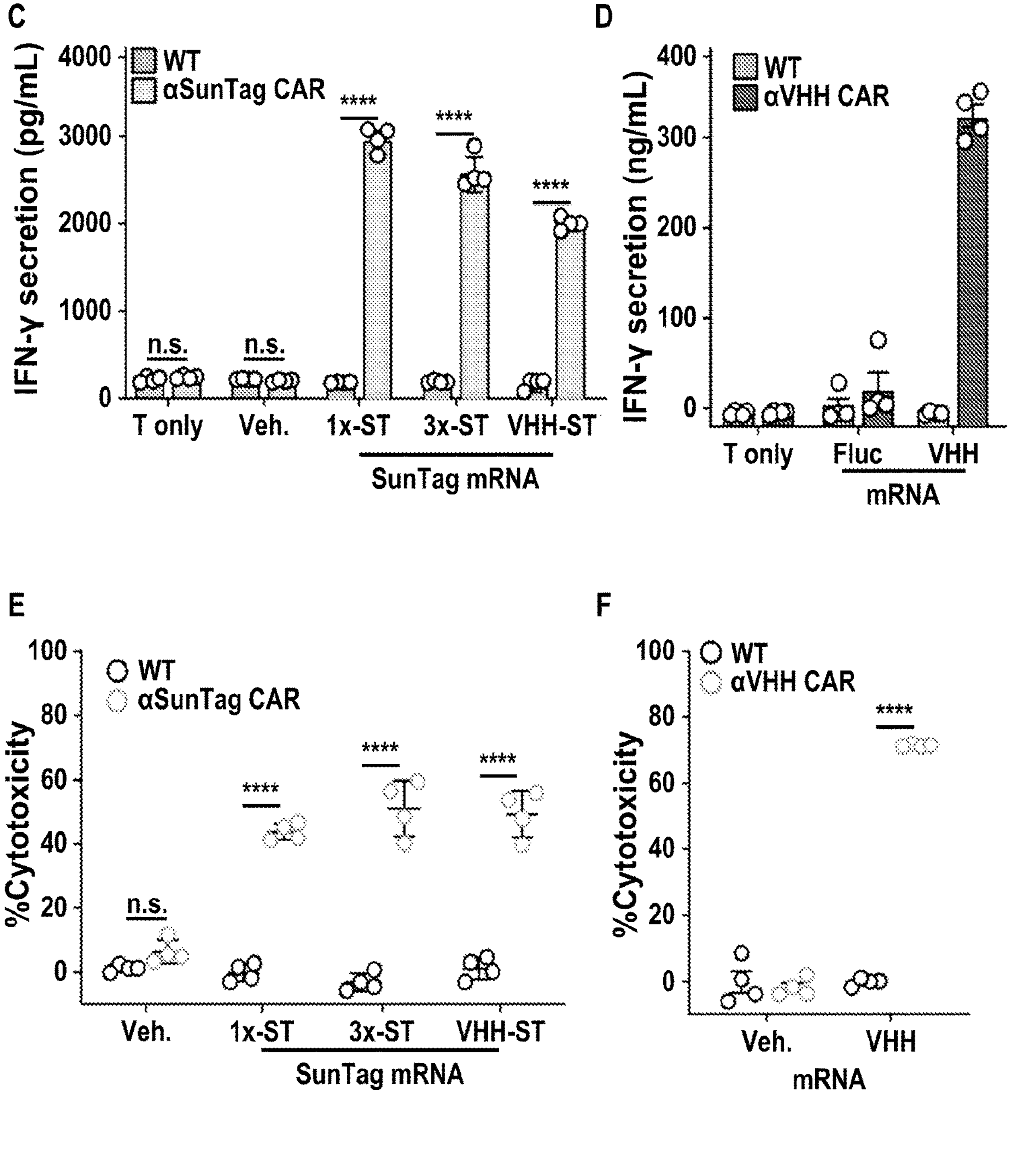
FIG. 17C, FIG. 17D, FIG. 17E, and FIG. 17F

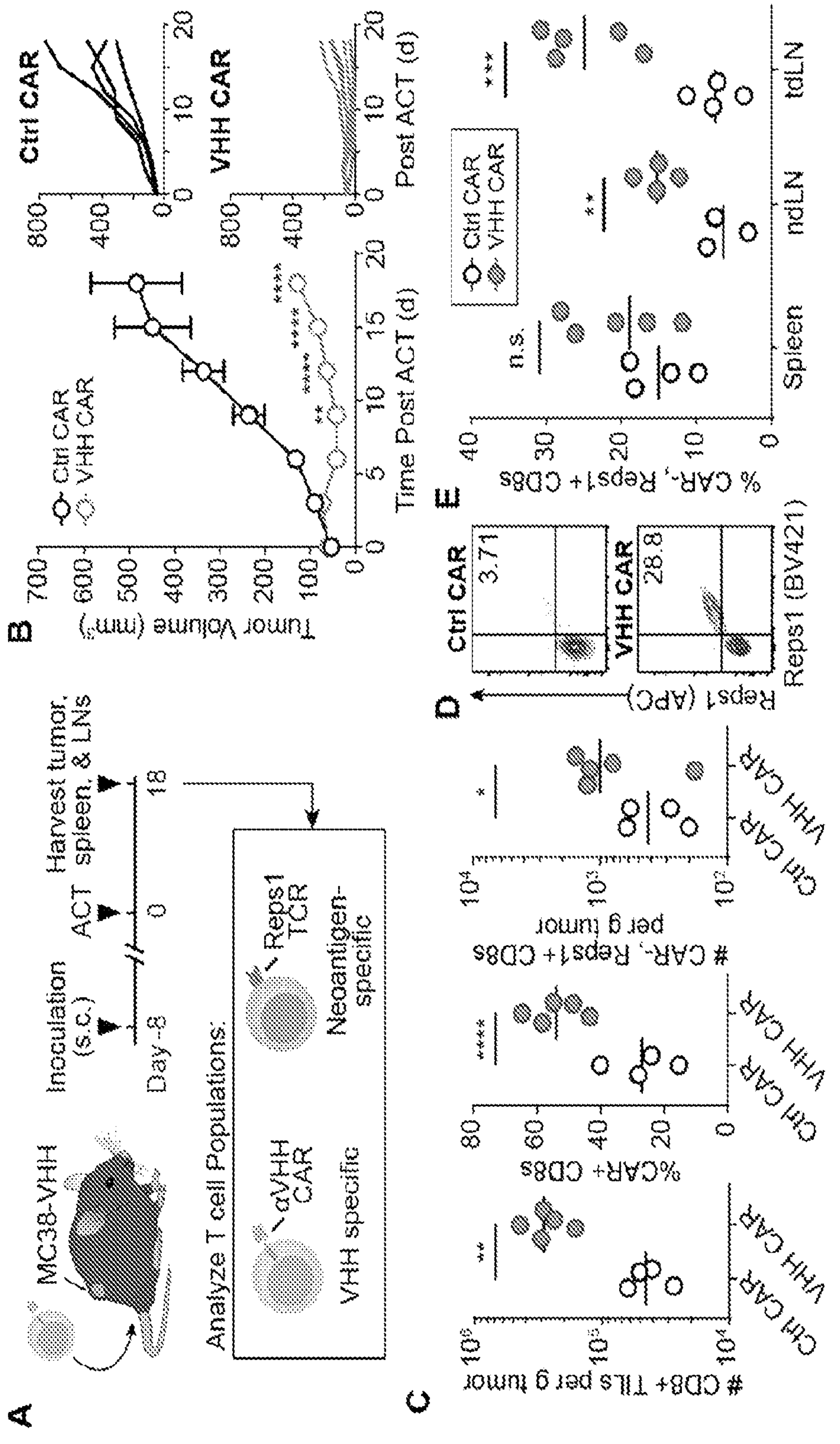
FIG. 21A, FIG. 21B, FIG. 21C, FIG. 21D, and FIG. 21E

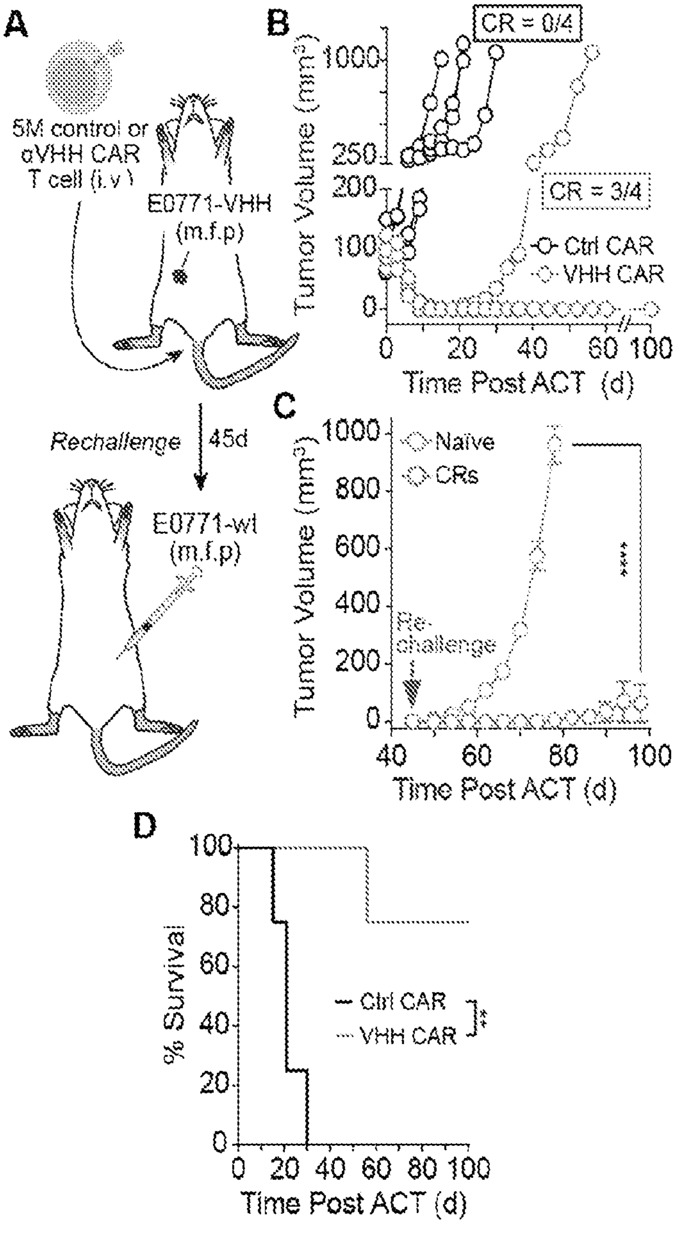
FIG. 22A, FIG. 22B, FIG. 22C, and FIG. 22D

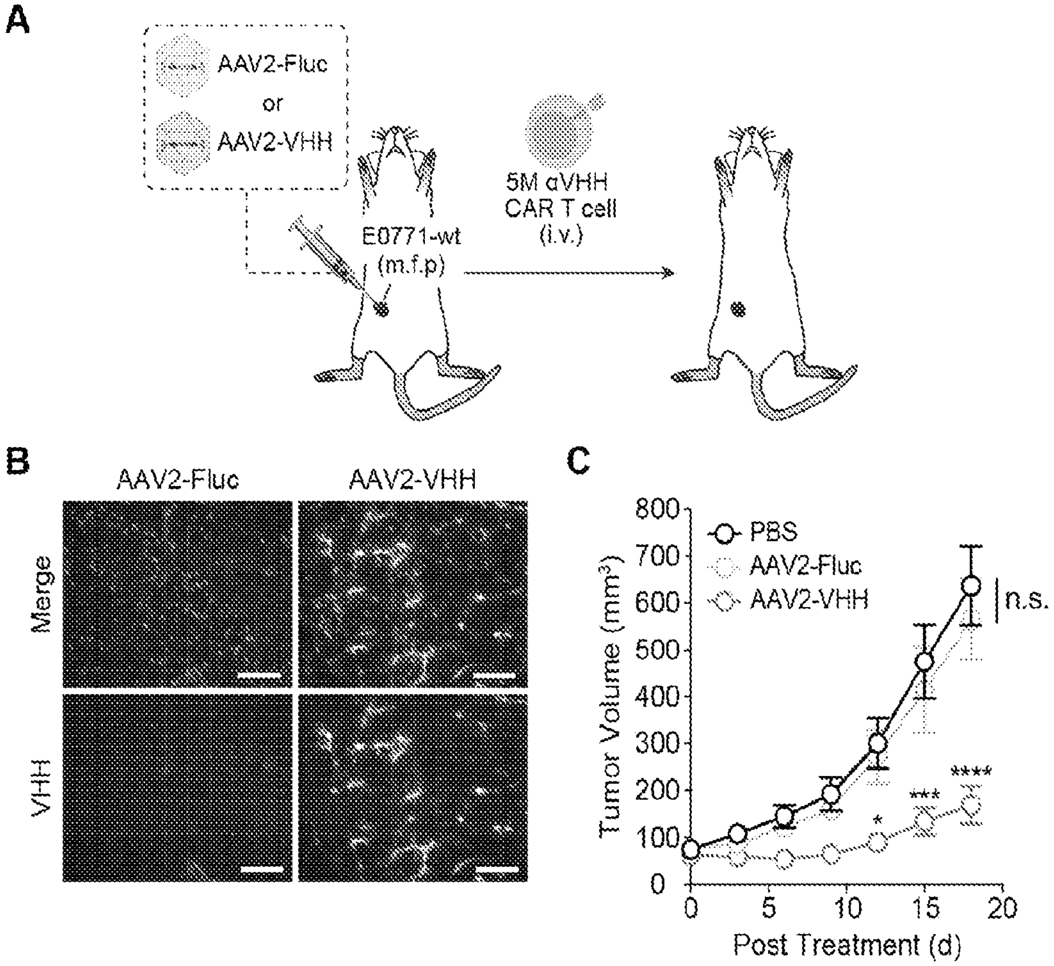
FIG. 23A, FIG. 23B, and FIG. 23C

SYNTHETIC ANTIGENS AS CHIMERIC ANTIGEN RECEPTOR (CAR) LIGANDS AND USES THEREOF

This application is a U.S. National Stage application filed under 35 U.S.C. § 371 of PCT/US2021/054972, filed on Oct. 14, 2021, which claims the benefit of U.S. Application No. 63/091,884, filed on Oct. 14, 2020, which is incorporated herein by reference in its entirety.

This invention was made with government support under Grant No. DP2HD091793 and UL1TR000454, awarded by the National Institutes of Health. The government has certain rights in the invention.

REFERENCE TO SEQUENCE LISTING

The sequence listing submitted on Apr. 14, 2023, as an .TXT file entitled "10034-069US1_Sequence_Listing.TXT" created on Apr. 13, 2023, and having a file size of 33,530 bytes is hereby incorporated by reference pursuant to 37 C.F.R. § 1.52(e)(5).

I. BACKGROUND

Cytotoxic T lymphocytes (CTL) have tremendous curative potential as cell-based therapies for cancer. Remarkably, adoptively transferred T cells engineered with chimeric antigen receptors (CARs) have shown regression of hematological cancers and in some patients, complete remission of metastatic disease. However, the scarcity and heterogeneity of suitable tumor associated antigens (TAAs) remains a major impediment to achieving effective immunity against solid tumors. Technical challenges associated with the identification of neoantigens characteristic of individual tumors—along with the need to engineer and validate CARs or TCRs against new targets—are significant bottlenecks to achieving therapeutic efficacy across tumor types and pose limitations for scalable manufacturing and rapid translation. Additionally, many validated TAAs share expression with healthy tissue (e.g. HER2, EGFR), leading to on-target/off-tumor toxicities, and targeting these endogenous antigens can render T cell therapies ineffective against tumor escape variants and heterogenous tumors. What is needed are new tumor-specific antigens that can be used as targets for immunotherapy.

II. SUMMARY

Disclosed are methods and compositions related to synthetic antigens and chimeric antigen receptors targeting said antigens.

In one aspect, disclosed herein are synthetic antigen-chimeric antigen receptor systems comprising a synthetic antigen (such as, for example small molecules (including, but not limited to Fluorescein isothiocyanate (FITC), 3-Amino-3-(2-nitro-phenyl)propionic Acid (ANP) or indocyanine green (ICG)) or genetically encoded antigens (including, but not limited to epidermal growth factor receptor viii (EGFRviii), fluorescent proteins (including, but not limited to EBFP2, GFP, eGFP, hrGFP, d2GFP, TurboGFP, BFP, CFP, YFP, mYFP, Cerulean3, mCFP, Midoriishi Cyan, mCherry, tdTomato, mTangerine, mTagBFP2, mTurquoise2, mStrawberry, mGrape1, mGrape2, mRaspberry, mPlum, mOrange, mBanana, mHoneydew, Azami Green, ZsGreen, TagGFP2, Emerald, superfolder GFP, Clover, mNeonGreen, mVenus, mCitrine, Turbo YFP, mPapaya1, mOrange2, TagRFP, TagRFP-T, TurboRFP, mRuby2, FusionRed, mKate2, mCardinal, mNeptune2, T-Sapphire, mAmetrine, LSSmOrance, LssmKate2, iRFP, iRFP670, iRFP682, iRFP702, iRFP713, and iRFP720), luciferases (including, but not limited to (gaussia luciferase, renilla luciferase, firefly luciferase, or cypridina luciferase), congenic markers (such as, for example, thy1.1, thy1.2, CD45.1, and CD45.2), GCN4 (GCN4), anti-respiratory syncytial virus F glycoprotein (RSV-F) VHH single domain antibody, tobacco etch virus (TEV) protease, influenza hemagglutinin (HA) surface glycoprotein, a headless HA stem-based antigen (mini-HA), GILGFVFTL (9-mer flu peptide) (SEQ ID NO: 14), GPPQWNNPP (an all d-amino acid peptide) (SEQ ID NO: 15), Cytomegalovirus (CMV) peptide, Epstein-Barr virus (EBV) peptide, ovalbulmin, heat shock protein 70 (HSP70), HSP90, flag tag (DYJDDDDK) (SEQ ID NO: 16), and/or HA Tag (YPYDVPDYA) (SEQ ID NO: 17); and a chimeric antigen receptor that targets said antigen. For example, the synthetic antigen of the synthetic antigen-chimeric antigen receptor systems can be encoded by any of SEQ ID NO: 8, SEQ ID NO: 9, SEQ ID NO: 10, or SEQ ID NO: 11.

In one aspect, disclosed herein are synthetic antigen-chimeric antigen receptor systems of any preceding aspect; wherein the chimeric antigen receptor comprises a single chain (sc) Fv (scFv) that specifically binds to the synthetic antigen (such as, for example general control protein GCN4 (GCN4), anti-respiratory syncytial virus F glycoprotein (RSV-F) VHH single domain antibody, or Fluorescein isothiocyanate (FITC)). In one aspect, the chimeric antigen receptor comprises the amino acid sequence as set forth in SEQ ID NO: 1, SEQ ID NO: 2, SEQ ID NO: 3, SEQ ID NO: 4, SEQ ID NO: 5, SEQ ID NO: 6, or SEQ ID NO: 7.

Also disclosed herein are synthetic antigen-chimeric antigen receptor systems of any preceding aspect, wherein the synthetic antigen and/or chimeric antigen receptor is encoded on a plasmid, viral vector (such as, for example, an Adenoviral vector, AAV vector, or lentiviral vector), minicircle DNA, or mRNA. In some aspects, the synthetic antigen of the synthetic antigen-chimeric antigen receptor system of any preceding aspect can be delivered by a fusogenic liposome (such as, for example a membrane fusogenic liposome (MFL)).

In one aspect, disclosed herein are synthetic antigen-chimeric antigen receptor systems of any preceding aspect, further comprising an immune cell (such as, for example, T cell, Natural Killer (NK) cell, NK T cell, or macrophage). In some aspect, the immune cell has been transduced with the chimeric antigen receptor creating a CAR T cell, CAR Natural Killer Cell (CAR NK cell), CAR NK T cell, CAR Macrophage (CARMA).

Also disclosed herein are methods of treating, reducing, decreasing, inhibiting, ameliorating, and/or preventing a cancer and/or metastasis in a subject comprising: transfecting/transducing a cancerous cell, tumor associated fibroblasts, myeloid-derived suppressor cells (MDSCs), regulatory T cells (Tregs), or extracellular matrix (ECM) with a synthetic antigen (such as, for example small molecules (including, but not limited to Fluorescein isothiocyanate (FITC), 3-Amino-3-(2-nitro-phenyl)propionic Acid (ANP) or indocyanine green (ICG)) or genetically encoded antigens (including, but not limited to epidermal growth factor receptor viii (EGFRviii), fluorescent proteins (including, but not limited to EBFP2, GFP, eGFP, hrGFP, d2GFP, TurboGFP, BFP, CFP, YFP, mYFP, Cerulean3, mCFP, Midoriishi Cyan, mCherry, tdTomato, mTangerine, mTagBFP2, mTurquoise2, mStrawberry, mGrape1, mGrape2, mRaspberry, mPlum, mOrange, mBanana, mHoneydew, Azami Green, ZsGreen, TagGFP2, Emerald, superfolder GFP, Clover, mNeonGreen, mVenus, mCitrine, Turbo YFP, mPapaya1, mOrange2, TagRFP, TagRFP-T, TurboRFP, mRuby2, FusionRed, mKate2, mCardinal, mNeptune2, T-Sapphire, mAmetrine, LSSmOrance, LssmKate2, iRFP, iRFP670, iRFP682, iRFP702, iRFP713, and iRFP720), luciferases (including, but not limited to (gaussia luciferase, renilla luciferase, firefly luciferase, or cypridina luciferase), congenic markers (such as, for example, thy1.1, thy1.2, CD45.1, and CD45.2), GCN4 (GCN4), anti-respiratory syncytial virus F glycoprotein (RSV-F) VHH single domain antibody, tobacco etch virus (TEV) protease, influenza hemagglutinin (HA) surface glycoprotein, a headless HA stem-based antigen (mini-HA), GILGFVFTL (9-mer flu peptide) (SEQ ID NO: 14), GPPQWNNPP (an all d-amino acid peptide) (SEQ ID NO: 15), Cytomegalovirus (CMV) peptide, Epstein-Barr virus (EBV) peptide, ovalbulmin, heat shock protein 70 (HSP70), HSP90, flag tag (DYJDDDDK) (SEQ ID NO: 16), and/or HA Tag (YPYDVPDYA) (SEQ ID NO: 17)); and administering to the subject a chimeric antigen receptor (CAR) immune cell (such as, for example, a CAR T cell, CAR Natural Killer Cell (CAR NK cell), CAR NK T cell, CAR Macrophage (CARMA)); wherein the CAR immune cell specifically targets and binds the synthetic antigen thereby killing the cancer cell. tumor associated fibroblast, regulatory T cells (Tregs), or myeloid-derived suppressor cell (MDSC).

In one aspect, disclosed herein are methods of treating, reducing, decreasing, inhibiting, ameliorating, and/or preventing a cancer and/or metastasis of any preceding aspect wherein the synthetic antigen is expressed on the membrane of the transfected/transduced cell. In some aspects the synthetic antigen is transfected/transduced into the cancerous cell, tumor associated fibroblasts, myeloid-derived suppressor cells (MDSCs), regulatory T cells (Tregs), or extracellular matrix (ECM), via plasmid, liposome, viral vector, minicircle DNA, or mRNA.

Also disclosed herein are methods of treating, reducing, decreasing, inhibiting, ameliorating, and/or preventing a cancer and/or metastasis of any preceding aspect, further comprising obtaining an immune cell (such as, for example, T cell, Natural Killer (NK) cell, NK T cell, or macrophage) from a donor source (such as, for example, an immune cell obtained from an autologous or allogeneic donor. Thus, in some aspects, disclosed herein are methods of treating, reducing, decreasing, inhibiting, ameliorating, and/or preventing a cancer and/or metastasis of any preceding aspect further comprising transducing the immune cell with the chimeric antigen receptor.

In one aspect, disclosed herein are methods of treating, reducing, decreasing, inhibiting, ameliorating, and/or preventing a cancer and/or metastasis of any preceding aspect wherein the CAR immune cell is administered to the subject before, after, or concurrently with the transfection/transduction of the cancerous cell, tumor associated fibroblasts, myeloid-derived suppressor cells (MDSCs), regulatory T cells (Tregs), or extracellular matrix (ECM).

In one aspect, disclosed herein are methods of treating, reducing, decreasing, inhibiting, ameliorating, and/or preventing a cancer and/or metastasis of any preceding aspect; wherein treatment of the primary tumor results in abscopal treatment of the metastatic tumor

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 13:
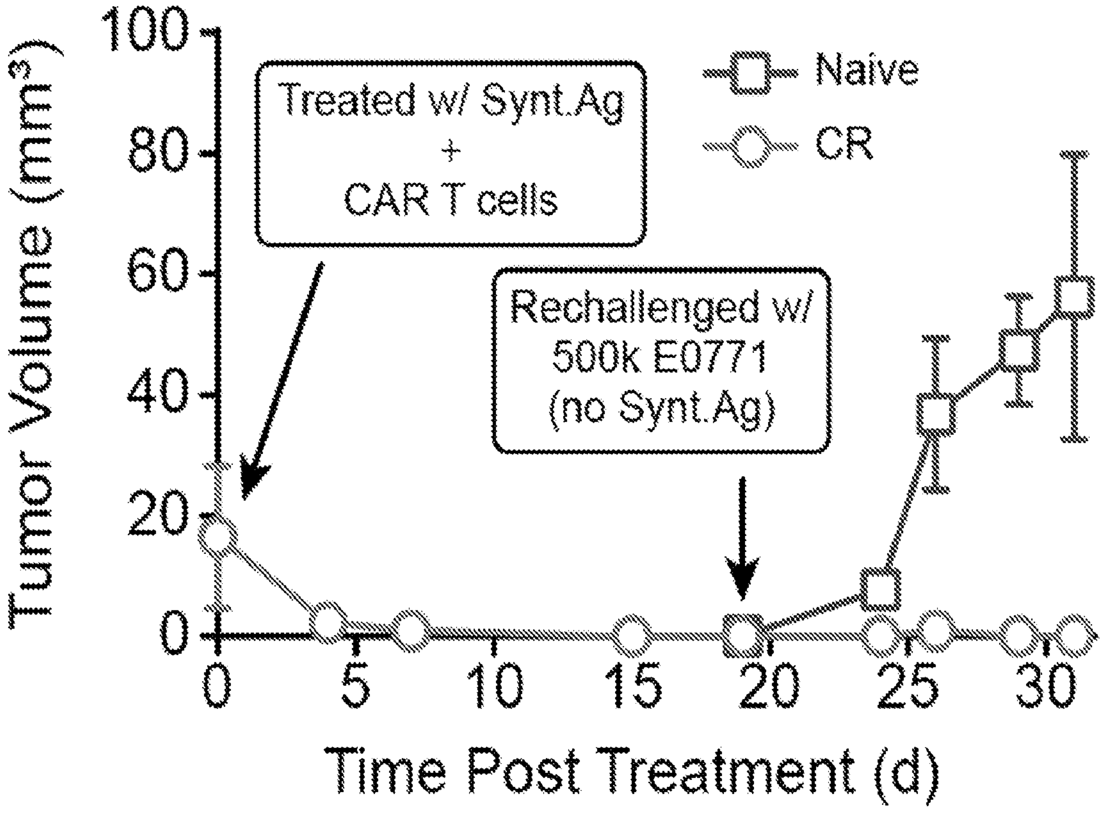

FIG. 13 shows tumor growth curves of mice which showed a complete response to synthetic antigen and CAR T cell treatment. Complete responders (CR) were rechallenged with 500k E0771 tumor cells 19 days after treatment. Naïve mice were treated as controls.

Figure 14:
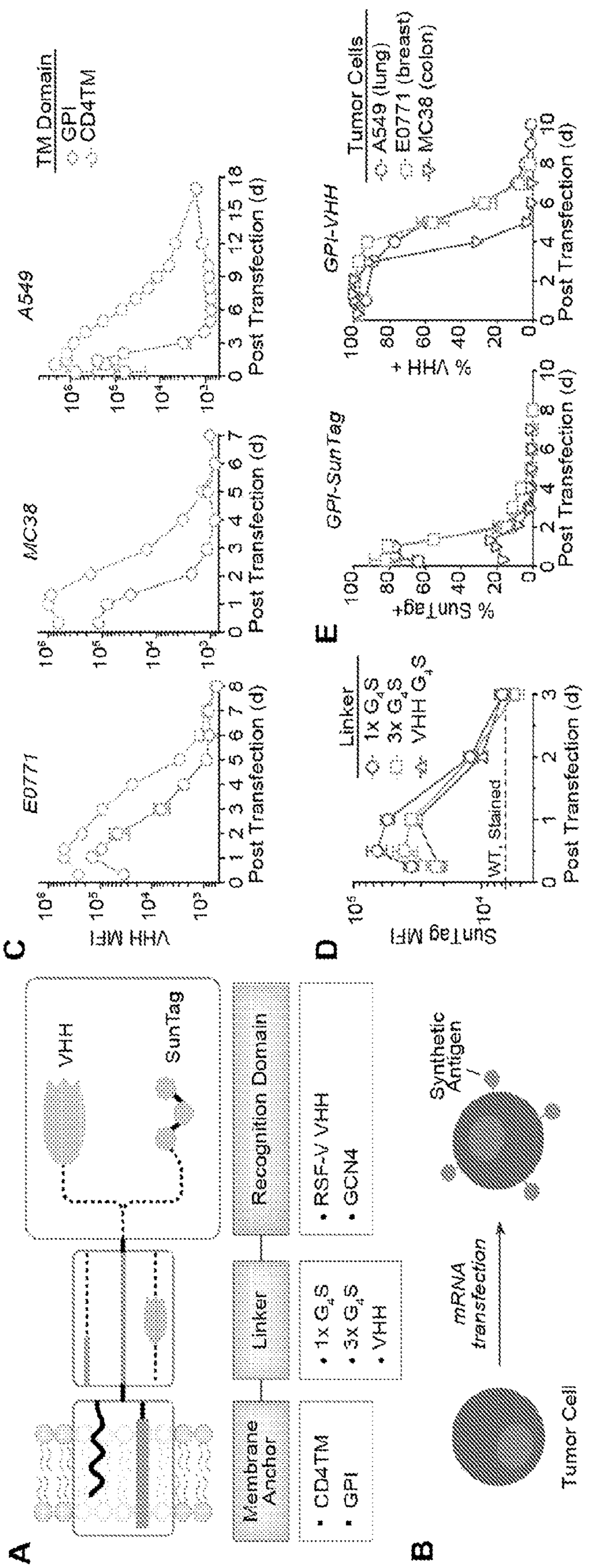

FIGS. 14A, 14B, 14C, 14D, and 14E show expression kinetics of synthetic antigen constructs. FIG. 14A shows mRNA constructs tested consist of a membrane anchor, a linker, and a recognition domain. These constructs are (14B) transfected into tumor cells to achieve synthetic antigen expression. FIG. 14C shows expression kinetics of GPI-anchored and CD4TM-anchored synthetic antigens consisting of a 1×G4S linker and the RSV-F VHH recognition domain on the surface of indicated tumor cells. FIG. 14D shows expression kinetics of mRNA constructs with a GPI-anchor, SunTag recognition domain, and indicated linker domains. FIG. 14E shows expression kinetics of GPI-anchored SunTag or VHH on the surface of indicated tumor cell lines.

Figure 15:
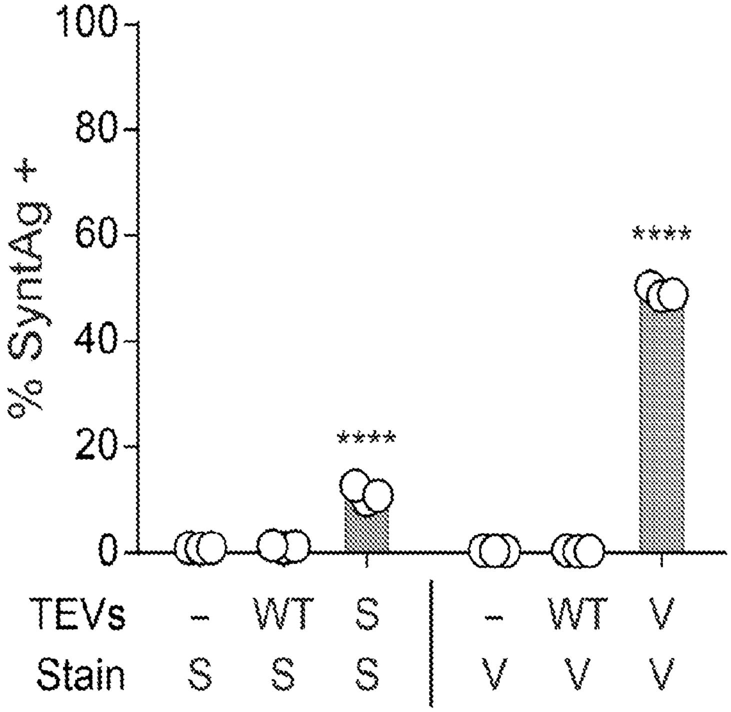

FIG. 15 shows synthetic antigens are propagated via tumor-derived extracellular vesicles. Tumor-derived extracellular vesicles (TEVs) were isolated from synthetic antigen treated E0771 tumor cells (WT=wildtype, S=SunTag, V=VHH). Wildtype tumor cells were then treated with TEVs and stained for synthetic antigen expression. One-way ANOVA; mean±s.d. is depicted; n=3, ****p<0.0001.

FIGS. 16A, 16B, 16C, 16D, 16E, 16F, and 16G show that murine αVHH and αGCN4 CAR T cells recognize and kill tumor cells expressing cognate synthetic antigens. FIGS. 16A and 16B show a schematic of murine CAR constructs for targeting synthetic antigens expressed on the surface of tumor cells. FIG. 16C shows surface expression of Suntag CAR (top) and VHH CAR (bottom) on primary murine T cells following retroviral transduction. FIG. 16D shows E0771 tumor cells were transfected with VHH or SunTag mRNA and co-incubated with either αVHH or αSunTag CARs. FIG. 16E shows staining of indicated T cell population with activation markers CD25 and CD69 following co-incubation with ST- or VHH-expressing E0771 tumor cells. FIG. 16F shows interferon gamma (IFN-γ) secretion by murine αSunTag CAR T, αVHH CAR T or untransduced (WT) T cells following a 24 hr co-culture at at a 2:1 effector:target (E:T) ratio with E0771 transfected with either VHH or SunTag mRNA. FIG. 16G shows killing of transfected E0771 tumor cells following the same 24-hr co-culture. One-way ANOVA; mean±s.d. is depicted; n=4; ****p<0.0001.

Figure 17A:
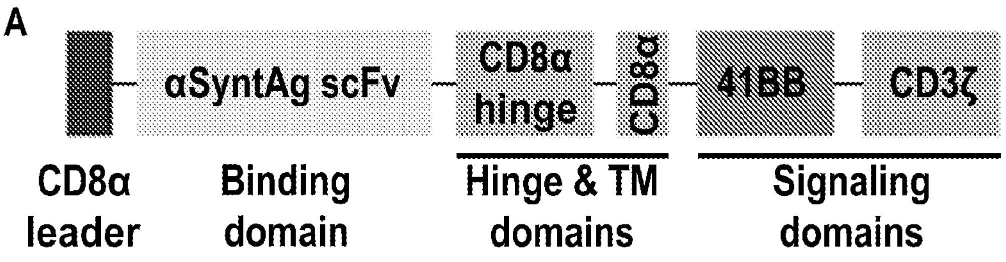
Figure 17B:
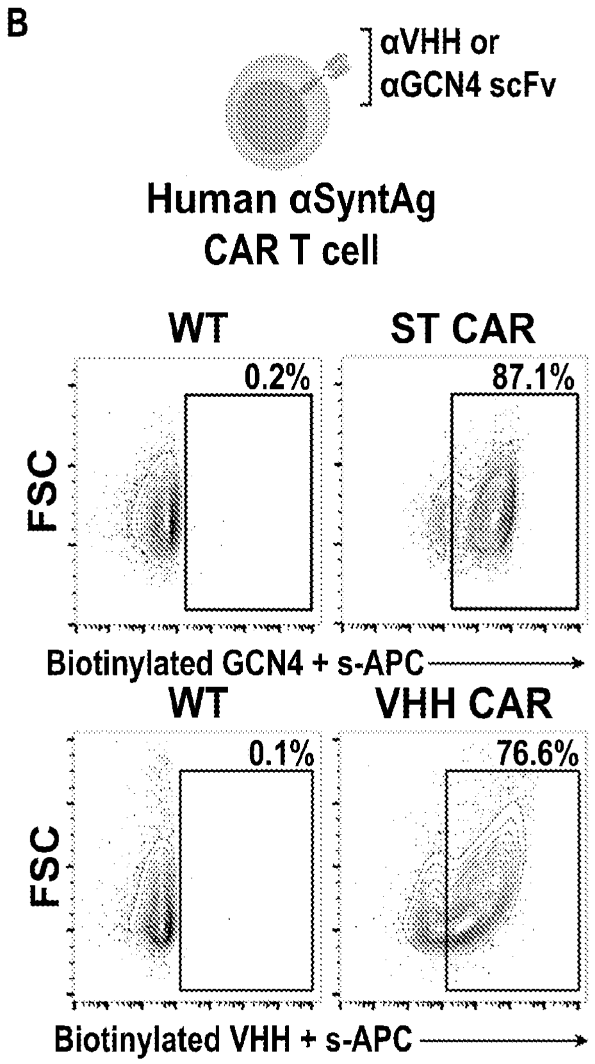

FIGS. 17A, 17B, 17C, 17D, 17E, and 17F show that Human αVHH and αGCN4 CAR T cells recognize and kill tumor cells expressing cognate synthetic antigens. FIG. 17A shows a schematic of human CAR constructs for targeting synthetic antigens (SyntAg) expressed on the surface of tumor cells. FIG. 17B shows surface expression of SunTag CAR (top) and VHH CAR (bottom) on primary murine T cells following lentiviral transduction. FIG. 17C shows interferon gamma (IFN-γ) secretion by αSunTag CAR T or untransduced (WT) T cells following a 24 hr coculture with A549 tumor cells expressing indicated SunTag constructs at a 1:1 effector:target (E:T) ratio. FIG. 17D shows interferon gamma (IFN-γ) secretion by αVHH CAR T or untransduced (WT) T cells following a 24 hr coculture with A549 tumor cells expressing VHH at a 2:1 effector:target (E:T) ratio. Killing of A549 tumor cells expressing either (17E) SunTag constructs or (17F) VHH following a 24 hr coculture with either CAR or untransduced (WT) T cells. Student's t-test; mean±s.d. is depicted; n=4; ****p<0.0001.

Figures 18A, 18B:
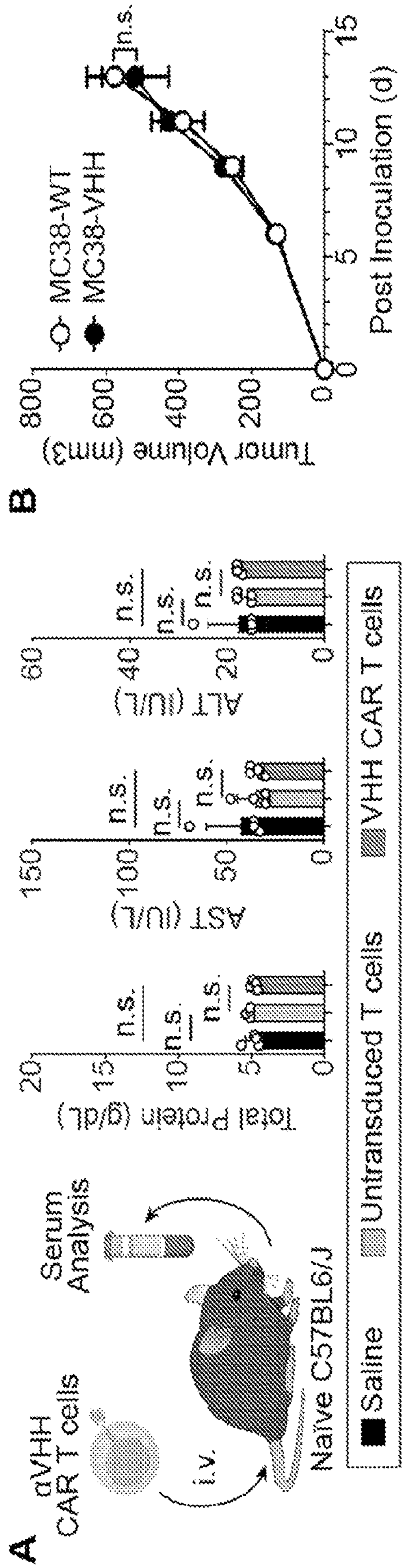

FIGS. 18A and 18B show αVHH CAR T cells are not toxic while VHH expression on tumor cells does not lead to changes in tumor growth. FIG. 18A show blood serum analysis 7d post i.v. administration of αVHH CAR T cells, untransduced T cells, or saline into naïve C57BL6/J mice. One-way ANOVA; mean±s.d. is depicted; n=4; n.s.=not significant. FIG. 18B shows tumor growth curves of wildtype MC38 (MC38-WT) or MC38 cells transduced to stably express VHH (MC38-VHH) without adoptive cell transfer of αVHH CAR T cells. Two-way ANOVA, mean±s.e.m. is depicted; n=4-6; n.s.=not significant.

Figure 19:
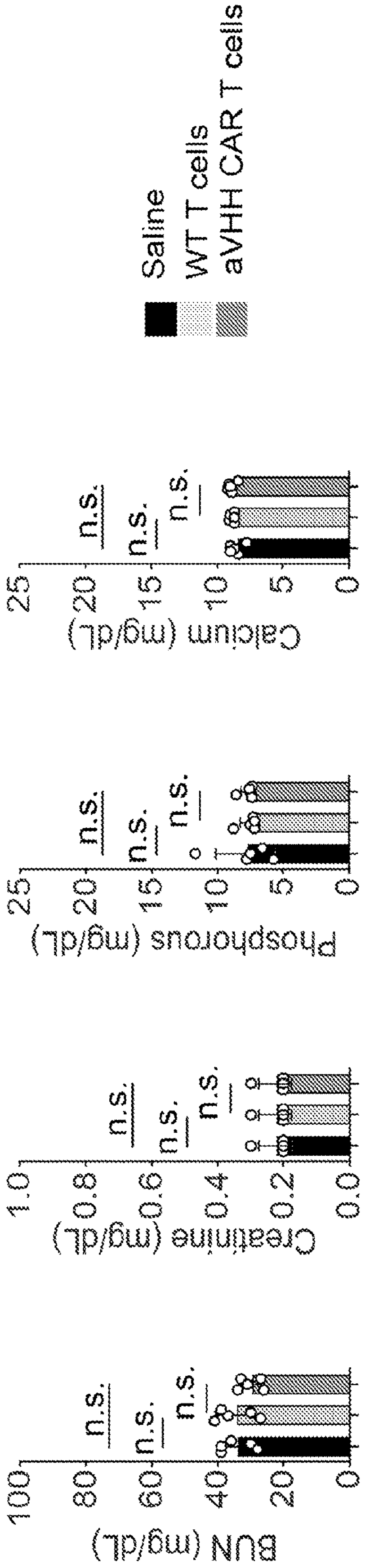

FIG. 19 shows additional blood serum analysis 7d post i.v. administration of αVHH CAR T cells, untransduced T cells, or saline.

Figures 20A, 20B:
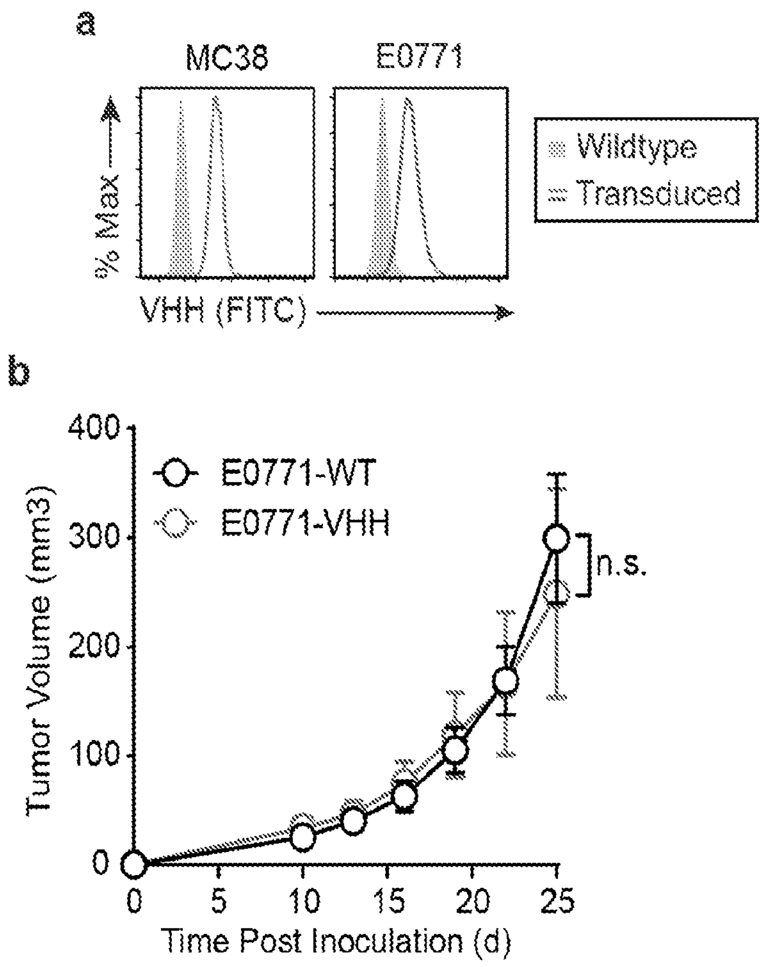

FIGS. 20A and 20B show tumor model characterization. FIG. 20A shows VHH expression on wildtype or transduced MC38 and E0771 tumor cells. FIG. 20B shows tumor growth curves of wildtype E0771 (E0771-WT) or E0771 cells transduced to stably express VHH (E0771-VHH) without adoptive cell transfer of αVHH CAR T cells. Two-way ANOVA, mean±s.e.m. is depicted; n=4-6; n.s.=not significant.

FIGS. 21A, 21B, 21C, 21D, and 21E show adoptive transfer of αVHH CAR T cells into mice with VHH-expressing tumors delays tumor growth, promotes infiltration of tumor-reactive T cells in the tumor, and leads to an increased frequency of tumor reactive T cells in the lymph nodes. FIG. 21A shows mice bearing MC38-VHH tumors were treated with αVHH CAR T cells. FIG. 21B show tumor growth curves of MC38-VHH tumor-bearing mice treated with αVHH CAR T cells. Two-way ANOVA, mean±s.e.m. is depicted; n=4; *p<0.05; p<0.01; *p<0.001; **p<0.0001. FIG. 21C shows count and frequency of indicated T cell populations isolated from the tumor. FIG. 21D shows representative flow plot of endogenous (CAR-) T cell expression of the Reps1 TCR, followed by (21**E) the frequency of this population in the tumor, non-draining (ndLN) and tumor draining (tdLN) lymph nodes. Student's t-test ANOVA, mean is depicted; n=4-5; *p<0.05; p<0.01; *p<0.001; ****p<0.0001.

FIGS. 22A, 22B, 22C, and 22D show cured mice treated with αVHH CARs are resistant to tumor rechallenge with wildtype tumors. FIG. 21A shows mice bearing E0771-VHH tumors were treated with αVHH CAR T cells. FIG. 21B shows individual traces of tumor growth curves of E0771-VHH tumor-bearing mice treated with control CAR T cells (black) or αVHH CAR T cells (blue) (CR=complete responders). 45 days after initial treatment, cured mice were (21C) rechallenged with wildtype E0771 tumor cells. VHH expression on wildtype or transduced MC38 and E0771 tumor cells. Two-way ANOVA, mean±s.e.m. is depicted; n.s.=not significant. FIG. 21D shows survival curves of tumor-bearing mice following initial treatment and rechallenge, log-rank (Mantel-Cox) test; **p<0.01.

FIGS. 23A, 23B, and 23C show AAV-mediated expression of VHH in combination with adoptive transfer of αVHH CAR T cells delays tumor growth. FIG. 23A shows mice bearing wildtype E0771 tumors were first treated with AAV2-Fluc or AAV2-VHH, followed by adoptive transfer of αVHH CAR T cells. FIG. 23B shows tumor cryosections were fixed and stained for VHH expression. Scale bar=60 μm. FIG. 23C shows tumor growth curves of wildtype E0771 tumor-bearing mice treated with AAV2 (Fluc or VHH) and αVHH CAR T cells. Two-way ANOVA, mean±s.e.m. is depicted; n=6; *p<0.05; *p<0.001; **p<0.0001.

Figure 24:
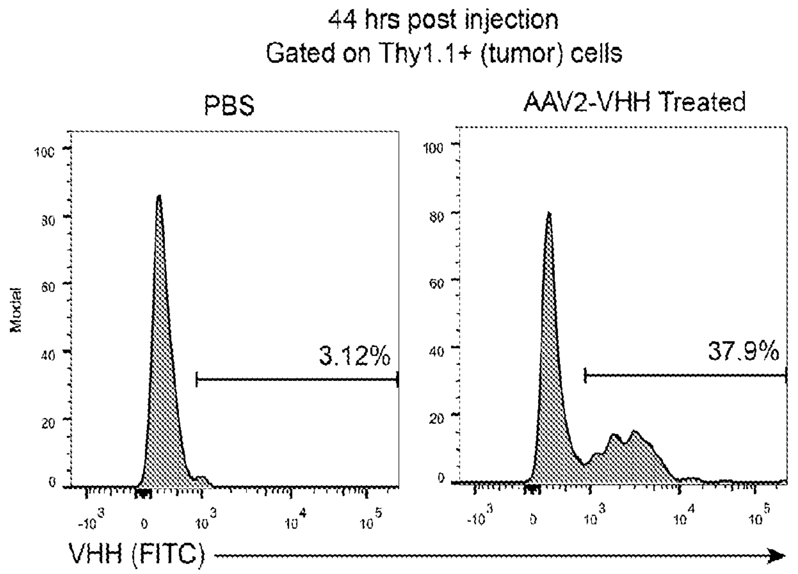

FIG. 24 shows AAV-mediated expression of VHH in MC38 tumors. VHH expression detected by flow cytometry 44 hrs post injection of 1.5e9 GCs of AAV2-VHH into MC38-Thy1.1 tumor cells. Data are gated on Thy1.1 (tumor) cells.

Figure 25:
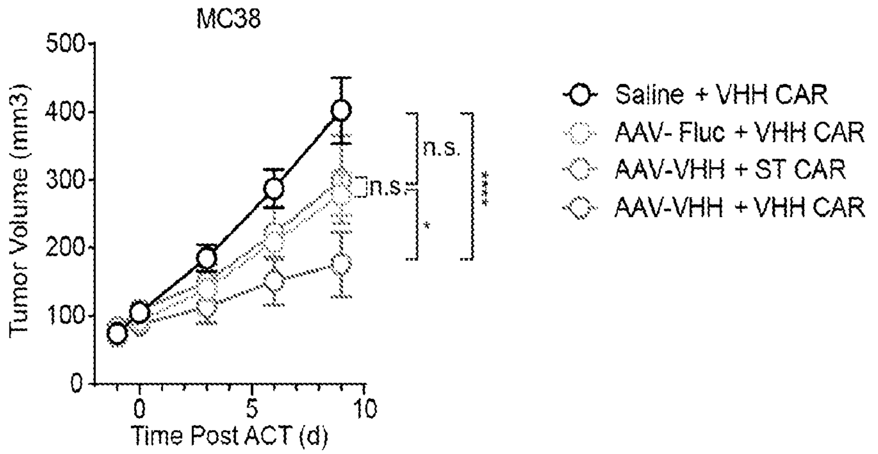

FIG. 25 shows AAV-mediated expression of VHH in combination with adoptive transfer of αVHH CAR T cells delays tumor growth in MC38 tumors. Tumor growth curves of wildtype MC38 tumor-bearing mice treated with AAV2 (Fluc or VHH) and indicated CAR T cells. Two-way ANOVA, mean±s.e.m. is depicted; n=6; *p<0.05; ****p<0.0001.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular synthetic antigen, chimeric antigen receptor recognizing said synthetic antigen, and/or synthetic antigen-chimeric antigen receptor system is disclosed and discussed and a number of modifications that can be made to a number of molecules including the synthetic antigen, chimeric antigen receptor recognizing said synthetic antigen, and/or synthetic antigen-chimeric antigen receptor system are discussed, specifically contemplated is each and every combination and permutation of synthetic antigen, chimeric antigen receptor recognizing said synthetic antigen, and/or synthetic antigen-chimeric antigen receptor system and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Figure 1:
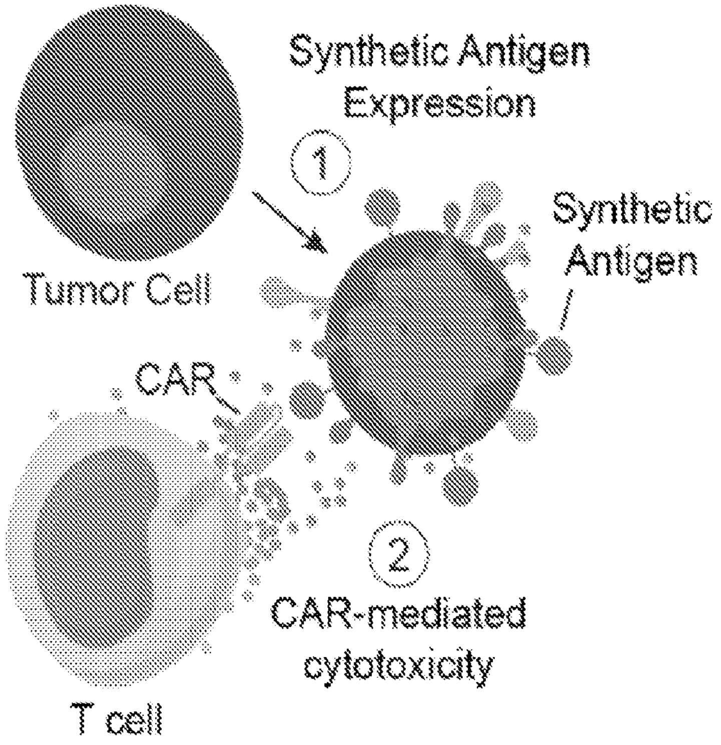
FIG. 1 shows that following delivery of synthetic antigens using non-viral methods, target tumor cells are recognized and killed by CAR T cells.

Herein is introduced the use of synthetic antigens as chimeric antigen receptor (CAR) ligands to sensitize tumors to T cell-mediated cytotoxicity (FIG. 1). To circumvent the challenges associated with identifying neoantigens, treating heterogenous tumors, and targeting endogenous antigens also expressed by healthy tissue, the expression of fully synthetic antigens was triggered on solid tumors in situ for subsequent targeting by chimeric antigen receptors (CARs). This platform renders tumors, including those which are untargetable and heterogenous, vulnerable to T cell recognition and enables the use of a single CAR construct to treat tumors lacking immunogenic antigens, ultimately expanding the application of CAR T cell therapies across cancer types. Accordingly, in one aspect, disclosed herein are synthetic antigen-chimeric antigen receptor systems comprising a synthetic antigen (such as, for example small molecules (including, but not limited to Fluorescein isothiocyanate (FITC), 3-Amino-3-(2-nitro-phenyl)propionic Acid (ANP) or indocyanine green (ICG)) or genetically encoded antigens (including, but not limited to epidermal growth factor receptor viii (EGFRviii), fluorescent proteins (including, but not limited to EBFP2, GFP, eGFP, hrGFP, d2GFP, TurboGFP, BFP, CFP, YFP, mYFP, Cerulean3, mCFP, Midoriishi Cyan, mCherry, tdTomato, mTangerine, mTagBFP2, mTurquoise2, mStrawberry, mGrape1, mGrape2, mRaspberry, mPlum, mOrange, mBanana, mHoneydew, Azami Green, ZsGreen, TagGFP2, Emerald, superfolder GFP, Clover, mNeonGreen, m Venus, mCitrine, Turbo YFP, mPapaya1, mOrange2, TagRFP, TagRFP-T, TurboRFP, mRuby2, FusionRed, mKate2, mCardinal, mNeptune2, T-Sapphire, mAmetrine, LSSmOrance, LssmKate2, iRFP, iRFP670, iRFP682, iRFP702, iRFP713, and iRFP720), luciferases (including, but not limited to (gaussia luciferase, renilla luciferase, firefly luciferase, or cypridina luciferase), congenic markers (such as, for example, thy1.1, thy1.2, CD45.1, and CD45.2), GCN4 (GCN4), anti-respiratory syncytial virus F glycoprotein (RSV-F) VHH single domain antibody, tobacco etch virus (TEV) protease, influenza hemagglutinin (HA) surface glycoprotein, a headless HA stem-based antigen (mini-HA), GILGFVFTL (9-mer flu peptide) (SEQ ID NO: 14), GPPQWNNPP (an all d-amino acid peptide) (SEQ ID NO: 15), Cytomegalovirus (CMV) peptide, Epstein-Barr virus (EBV) peptide, ovalbulmin, heat shock protein 70 (HSP70), HSP90, flag tag (DYJDDDDK) (SEQ ID NO: 16), and/or HA Tag (YPYDVPDYA) (SEQ ID NO: 17)); and a chimeric antigen receptor that targets said antigen (for example, a CAR comprising an amino acid sequence as set forth in SEQ ID NO: 1, SEQ ID NO: 2, SEQ ID NO: 4, SEQ ID NO: 5, SEQ ID NO: 6, and/or SEQ ID NO: 7).

It is understood and herein contemplated that, as used herein, "synthetic antigen" refers to any peptide, protein, glycoprotein, antibody or antibody fragment that is not endogenous to a host subject. Thus, not only can a synthetic antigen be a completely synthetic (i.e., man-made) peptide, protein, glycoprotein, antibody or antibody fragment including recombinant or designed peptides, proteins, glycoproteins, antibodies or antibody fragments (e.g., VHH) not found in nature, but also peptides, proteins, glycoproteins, antibodies or antibody fragments that are not encoded or expressed in the host subject (for example, a hypothetical avian protein or peptide that does not have a human homolog being used in a human subject). Examples of synthetic antigens are well known and can include, but are not limited to small molecules (including, but not limited to Fluorescein isothiocyanate (FITC), 3-Amino-3-(2-nitro-phenyl)propionic Acid (ANP) or indocyanine green (ICG)) or genetically encoded antigens (including, but not limited to epidermal growth factor receptor viii (EGFRviii), fluorescent proteins (including, but not limited to EBFP2, GFP, eGFP, hrGFP, d2GFP, TurboGFP, BFP, CFP, YFP, mYFP, Cerulean3, mCFP, Midoriishi Cyan, mCherry, tdTomato, mTangerine, mTagBFP2, mTurquoise2, mStrawberry, mGrape1, mGrape2, mRaspberry, mPlum, mOrange, mBanana, mHoneydew, Azami Green, ZsGreen, TagGFP2, Emerald, superfolder GFP, Clover, mNeonGreen, mVenus, mCitrine, Turbo YFP, mPapaya1, mOrange2, TagRFP, TagRFP-T, TurboRFP, mRuby2, FusionRed, mKate2, mCardinal, mNeptune2, T-Sapphire, mAmetrine, LSSmOrance, LssmKate2, iRFP, iRFP670, iRFP682, iRFP702, iRFP713, and iRFP720), luciferases (including, but not limited to (*gaussia* luciferase, *renilla* luciferase, firefly luciferase, or cypridina luciferase), congenic markers (such as, for example, thy1.1, thy1.2, CD45.1, and CD45.2), GCN4 (GCN4), anti-respiratory syncytial virus F glycoprotein (RSV-F) VHH single domain antibody, tobacco etch virus (TEV) protease, influenza hemagglutinin (HA) surface glycoprotein, a headless HA stem-based antigen (mini-HA), GILGFVFTL (9-mer flu peptide) (SEQ ID NO: 14), GPPQWNNPP (an all d-amino acid peptide) (SEQ ID NO: 15), Cytomegalovirus (CMV) peptide, Epstein-Barr virus (EBV) peptide, ovalbulmin, heat shock protein 70 (HSP70), HSP90, flag tag (DYJDDDDK) (SEQ ID NO: 16), and/or HA Tag (YPYDVPDYA) (SEQ ID NO: 17)). To enhance the expression level of the synthetic antigen, The synthetic antigen can be conjugated to a SunTag via linker or GPI anchor (such as, for example, SEQ ID NO: 8, SEQ ID NO: 9, and/or SEQ ID NO: 10). It is understood and herein contemplated that the synthetic antigens can be transfected or transduced into a target cell in vivo and ultimately expressed on a cell of interest (i.e., target cell). Upon expression on the cell surface, the synthetic antigen serves as a in vivo ligand for a chimeric antigen receptor. Thus, in one aspect, disclosed herein are synthetic antigen-chimeric antigen receptor systems wherein the synthetic antigen is expressed in vivo of a host subject.

As noted above, the disclosed synthetic antigen-chimeric antigen receptor systems also comprise chimeric antigen receptors (CARs) that recognize, and specifically bind to the synthetic antigen. In one aspect, disclosed herein are synthetic antigen-chimeric antigen receptor systems of any preceding aspect; wherein the chimeric antigen receptor comprises a single chain (sc) Fv (scFv) that specifically binds to the synthetic antigen (such as, for example general control protein GCN4 (GCN4), anti-respiratory syncytial virus F glycoprotein (RSV-F) VHH single domain antibody, or Fluorescein isothiocyanate (FITC)). In one aspect, the chimeric antigen receptor comprises the amino acid sequence as set forth in SEQ ID NO: 1, SEQ ID NO: 2, SEQ ID NO: 3, SEQ ID NO: 4, SEQ ID NO: 5, SEQ ID NO: 6, or SEQ ID NO: 7. These CARs can be incorporated into an immune cell (such as, for example, a T cell (including but not limited to CD4 T cells and CD8 T cells), natural killer (NK) cells, NK-T cells, and/or macrophage) thereby creating CAR T cell, CAR Natural Killer Cell (CAR NK cell), CAR NK T cell, CAR Macrophage (CARMA). Thus, in one aspect The immune cells used can come from any autologous or allogeneic donor source.

1. Delivery of the Compositions to Cells

As disclosed herein the synthetic antigens can be transfected or transduced into a cell and chimeric antigen receptors can be transduced into a cell (a cancer cell in the case of the synthetic antigen or an immune cell in the case of the CAR). It is understood and herein contemplated that the synthetic antigen and/or chimeric antigen receptor expression can be achieved by any means known in the art including techniques that manipulate genomic DNA, messenger and/or non-coding RNA and/or proteins. As such, the technologies or mechanisms that can be employed to insert the synthetic antigen of interest and/or chimeric antigen receptor include but are not limited to 1) technologies and reagents that target genomic DNA to result in an edited genome (e.g., homologous recombination to introduce a mutation such as a deletion into a gene, transposons (such as, for example, class II transposable elements comprising Sleeping Beauty transposase, Frog Prince, piggyBac, Tol2 and other Tc1/mariner-type transposases), zinc finger nucleases, meganucleases, transcription activator-like effectors (e.g., TALENs), triplexes, mediators of epigenetic modification, and CRISPR and rAAV technologies), 2) technologies and reagents that target RNA (e.g. agents that act through the RNAi pathway, antisense technologies, ribozyme technologies, retroviral vectors), 3) bacterial vectors (*Salmonella, E. coli*, mycobacteria, lactobacilli); and 4) technologies that target proteins (e.g., liposomes, including, but not limited to membrane fusogenic lipososmes).

There are a number of compositions and methods which can be used to deliver nucleic acids to cells, either ex vivo, in vitro, or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, transposons (such as, for example, class II transposable elements comprising Sleeping Beauty transposase, Frog Prince, piggyBac, Tol2 and other Tc1/mariner-type transposases), minicircle DNA, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Accordingly, also disclosed herein are synthetic antigen-chimeric antigen receptor systems, wherein the synthetic antigen and/or chimeric antigen receptor is encoded on a plasmid, viral vector (such as, for example, an Adenoviral vector, AAV vector, or lentiviral vector), transposon (such as, for example, class II transposable elements comprising Sleeping Beauty transposase, Frog Prince, piggyBac, Tol2 and other Tc1/mariner-type transposases), minicircle DNA, or mRNA. In some aspects the synthetic antigen of the synthetic antigen-chimeric antigen receptor system of any preceding aspect can be delivered by a fusogenic liposome (such as, for example a membrane fusogenic liposome (MFL)).

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

In one embodiment for incorporating synthetic antigen or chimeric antigen receptor expression is achieved using zinc finger nucleases (ZFNs). Synthetic ZFNs are composed of a custom designed zinc finger binding domain fused with e.g. a Fok1 DNA cleavage domain. As these reagents can be designed/engineered for editing the genome of a cell, including, but not limited to, knock out or knock in gene expression, in a wide range of organisms, they are considered one of the standards for developing stable engineered cell lines with desired traits. meganucleases, triplexes, CRISPR, and recombinant adeno-associated viruses have similarly been used for genome engineering in a wide array of cell types and are viable alternatives to ZFNs. The described reagents can be used to target promoters, protein-encoding regions (exons), introns, 5' and 3' UTRs, and more.

Another embodiment for modulating gene function utilizes the cell's endogenous or exogenous RNA interference (RNAi) pathways to target cellular messenger RNA. In this approach, gene targeting reagents include small interfering RNAs (siRNA) as well as microRNAs (miRNA). These reagents can incorporate a wide range of chemical modifications, levels of complementarity to the target transcript of interest, and designs (see U.S. Pat. No. 8,188,060) to enhance stability, cellular delivery, specificity, and functionality. In addition, such reagents can be designed to target diverse regions of a gene (including the 5 'UTR, the open reading frame, the 3' UTR of the mRNA), or (in some cases) the promoter/enhancer regions of the genomic DNA encoding the gene of interest. Gene modulation (e.g., knockdown) can be achieved by introducing (into a cell) a single siRNA or miRNA or multiple siRNAs or miRNAs (i.e., pools) targeting different regions of the same mRNA transcript. Synthetic siRNA/miRNA delivery can be achieved by any number of methods including but not limited to 1) self-delivery (US Patent Application No 2009/0280567A1), 2)

lipid-mediated delivery, 3) electroporation, or 4) vector/plasmid-based expression systems. An introduced RNA molecule may be referred to as an exogenous nucleotide sequence or polynucleotide.

As used herein, plasmid or viral vectors are agents that transport the disclosed nucleic acids, such as nucleic acids encoding synthetic antigens into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the cell of interest. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected, transduced, or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655

(1984); Seth, et al., *Mol. Cell. Biol.* 4:1528-1533 (1984); Varga et al., *J. Virology* 65:6061-6070 (1991); Wickham et al., *Cell* 73:309-319 (1993)).

A viral vector can be one based on an adenovirus which has had the E1 gene removed and these virions are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19 (such as, for example at AAV integration site 1 (AAVS1)). Vectors which contain this site-specific integration property are preferred. An especially preferred embodiment of this type of vector is the P4.1 C vector produced by Avigen, San Francisco, CA, which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically, the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., *Nature genetics* 8:33-41, 1994; Cotter and Robertson, *Curr Opin Mol Ther* 5:633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection or transduction, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the cells of interest (i.e., target cells) in a variety of ways. For example, the compositions can be delivered through electroporation, or through lipofection, or through calcium phosphate precipitation. The delivery mechanism chosen will depend in part on the type of cell targeted and whether the delivery is occurring for example in vivo, ex vivo, or in vitro.

Thus, the compositions can comprise, in addition to the disclosed plasmids, transpososns, or vectors for example, lipids such as liposomes, such as cationic liposomes (e.g., 1,2-di-O-octadecenyl-3-trimethylammonium propane (DOTMA), dioleoyl phosphatidylethanolamine (DOPE), dimyristoyl phosphatidylcholine (DMPC), dioleoyloxypropyltrimethylammonium (DOTAP), lipids conjugated to synthetic antigens (e.g., 1,2-Distearoyl-sn-glycero-3-phosphoethanolamine (DSPE)-polyethylene glycol (PEG)[2000], DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, MD), SUPERFECT (Qiagen, Inc. Hilden, Germany) and TRANSFECTAM (Promega Biotec, Inc., Madison, WI), as well as other liposomes developed according to procedures standard in the art. In addition, the disclosed nucleic acid or vector can be delivered in vivo by electroporation, the technology for which is available from Genetronics, Inc. (San Diego, CA) as well as by means of a SONOPORATION machine (ImaRx Pharmaceutical Corp., Tucson, AZ).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and Mckenzie, *Immunolog. Reviews,* 129:57-80, (1992); and Roffler, et al., *Biochem. Pharmacol,* 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

2. Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with synthetic antigens. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment.

Pepsin treatment yields a fragment that has two antigen combining sites and is still capable of cross-linking antigen.

As used herein, the term "antibody or fragments thereof" encompasses chimeric antibodies and hybrid antibodies, with dual or multiple antigen or epitope specificities, and fragments, such as F(ab')2, Fab', Fab, Fv, scFv, and the like, including hybrid fragments. Thus, fragments of the antibodies that retain the ability to bind their specific antigens are provided. For example, fragments of antibodies which maintain synthetic antigen binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

Also included within the meaning of "antibody or fragments thereof" are conjugates of antibody fragments and antigen binding proteins (single chain antibodies).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an sFv, Fv, Fab, Fab', F(ab')2, or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature,* 321:522-525 (1986), Reichmann et al., *Nature,* 332:323-327 (1988), and Presta, *Curr. Opin. Struct. Biol.,* 2:593-596 (1992)).

Methods for humanizing non-human antibodies are well known in the art. For example, humanized antibodies can be generated according to the methods of Winter and co-workers (Jones et al., *Nature,* 321:522-525 (1986), Riechmann et al., *Nature,* 332:323-327 (1988), Verhoeyen et al., *Science,* 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

3. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

C. METHOD OF TREATING CANCER

The disclosed synthetic antigen-chimeric antigen receptor systems can be used to treat any disease where uncontrolled cellular proliferation occurs such as cancers. Accordingly, in one aspect, disclosed herein are methods of treating, reducing, decreasing, inhibiting, ameliorating, and/or preventing a cancer and/or metastasis in a subject comprising: transfecting/transducing a cancerous cell, tumor associated fibroblast, myeloid-derived suppressor cell (MDSC), regulatory T cells (Tregs), or extracellular matrix (ECM) with a synthetic antigen (such as, for example small molecules (including, but not limited to Fluorescein isothiocyanate (FITC), 3-Amino-3-(2-nitro-phenyl)propionic Acid (ANP) or indocyanine green (ICG)) or genetically encoded antigens (including, but not limited to epidermal growth factor receptor viii (EGFRviii,) fluorescent proteins (including, but not limited to EBFP2, GFP, eGFP, hrGFP, d2GFP, TurboGFP, BFP, CFP, YFP, mYFP, Cerulean3, mCFP, Midoriishi Cyan, mCherry, tdTomato, mTangerine, mTagBFP2, mTurquoise2, mStrawberry, mGrape1, mGrape2, mRaspberry, mPlum, mOrange, mBanana, mHoneydew, Azami Green, ZsGreen, TagGFP2, Emerald, superfolder GFP, Clover, mNeonGreen, mVenus, mCitrine, Turbo YFP, mPapaya1, mOrange2, TagRFP, TagRFP-T, TurboRFP, mRuby2, FusionRed, mKate2, mCardinal, mNeptune2, T-Sapphire, mAmetrine, LSSmOrance, LssmKate2, iRFP, iRFP670, iRFP682, iRFP702, iRFP713, and iRFP720), luciferases (including, but not limited to (*gaussia* luciferase, *renilla* luciferase, firefly luciferase, or cypridina luciferase), congenic markers (such as, for example, thy1.1, thy1.2, CD45.1, and CD45.2), GCN4 (GCN4), anti-respiratory syncytial virus F glycoprotein (RSV-F) VHH single domain antibody, tobacco etch virus (TEV) protease, influenza hemagglutinin (HA) surface glycoprotein, a headless HA stem-based antigen (mini-HA), GILGFVFTL (9-mer flu peptide) (SEQ ID NO: 14), GPPQWNNPP (an all d-amino acid peptide) (SEQ ID NO: 15), Cytomegalovirus (CMV) peptide, Epstein-Barr virus (EBV) peptide, ovalbulmin, heat shock protein 70 (HSP70), HSP90, flag tag (DYJDDDDK) (SEQ ID NO: 16), and/or HA Tag (YPYDVPDYA) (SEQ ID NO: 17)); and adoptively transferring a chimeric antigen receptor immune cell into a host subject comprising the cancer by administering to the subject a chimeric antigen receptor (CAR) immune cell (such as, for example, a CAR T cell, CAR Natural Killer Cell (CAR NK cell), CAR NK T cell, CAR Macrophage (CARMA)); wherein the CAR immune cell specifically targets and binds the synthetic antigen thereby killing the cancer cell, tumor associated fibroblast, regulatory T cells (Tregs), or myeloid-derived suppressor cell (MDSC). It is understood and herein contemplated that the transfection/transduction of the synthetic antigen into the cancerous cell, tumor associated fibroblast, myeloid-derived suppressor cell (MDSC), regulatory T cells (Tregs), or extracellular matrix (ECM) occurs in vivo.

It is understood and herein contemplated that the for the chimeric antigen receptor to recognize a transfected/transduced cell, some portion or all of the expressed synthetic antigen should be visible (i.e., functionally available for binding/targeting) to the chimeric antigen receptor and thus on the cell surface. Accordingly, in one aspect, disclosed herein are methods of treating, reducing, decreasing, inhibiting, ameliorating, and/or preventing a cancer and/or metastasis of any preceding aspect wherein the synthetic antigen is expressed on the membrane of the transfected/transduced cell. As disclosed herein, the synthetic antigen can be transfected/transduced into the cancerous cell, tumor associated fibroblast, myeloid-derived suppressor cell (MDSC), regulatory T cells (Tregs), or extracellular matrix (ECM) via any means known in the art, including, but not limited to plasmid, liposome, viral vector, minicircle DNA, or mRNA.

As noted above, the disclosed synthetic antigen-chimeric antigen receptor systems can be used to treat any disease where uncontrolled cellular proliferation occurs such as cancers. A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

It is understood and herein contemplated that treatment of a primary tumor can have a protective against metastatic tumor formation or an abscopal effect on existing metastatic tumors. By treating the primary tumor, the protective immune response will guard against tumor spread and attack any secondary tumor formation. Accordingly, disclosed herein are methods of treating, reducing, decreasing, inhibiting, ameliorating, and/or preventing a secondary and/or metastasis tumor or tumor formation comprising transfecting/transducing a cancerous cell, tumor associated fibroblast, myeloid-derived suppressor cell (MDSC), regulatory T cells (Tregs), or extracellular matrix (ECM) with a synthetic antigen (such as, for example small molecules (including, but not limited to Fluorescein isothiocyanate (FITC), 3-Amino-3-(2-nitro-phenyl)propionic Acid (ANP) or indocyanine green (ICG)) or genetically encoded antigens (including, but not limited to epidermal growth factor receptor viii (EGFRviii,) fluorescent proteins (including, but not limited to EBFP2, GFP, eGFP, hrGFP, d2GFP, TurboGFP, BFP, CFP, YFP, mYFP, Cerulean3, mCFP, Midoriishi Cyan, mCherry, tdTomato, mTangerine, mTagBFP2, mTurquoise2, mStrawberry, mGrape1, mGrape2, mRaspberry, mPlum, mOrange, mBanana, mHoneydew, Azami Green, ZsGreen, TagGFP2, Emerald, superfolder GFP, Clover, mNeonGreen, m Venus, mCitrine, Turbo YFP, mPapaya1, mOrange2, TagRFP, TagRFP-T, TurboRFP, mRuby2, FusionRed, mKate2, mCardinal, mNeptune2, T-Sapphire, mAmetrine, LSSmOrance, LssmKate2, iRFP, iRFP670, iRFP682, iRFP702, iRFP713, and iRFP720), luciferases (including, but not limited to (gaussia luciferase, renilla luciferase, firefly luciferase, or cypridina luciferase), congenic markers (such as, for example, thy1.1, thy1.2, CD45.1, and CD45.2), GCN4 (GCN4), anti-respiratory syncytial virus F glycoprotein (RSV-F) VHH single domain antibody, tobacco etch virus (TEV) protease, influenza hemagglutinin (HA) surface glycoprotein, a headless HA stem-based antigen (mini-HA), GILGFVFTL (9-mer flu peptide) (SEQ ID NO: 14), GPPQWNNPP (an all d-amino acid peptide) (SEQ ID NO: 15), Cytomegalovirus (CMV) peptide, Epstein-Barr virus (EBV) peptide, ovalbulmin, heat shock protein 70 (HSP70), HSP90, flag tag (DYJDDDDK) (SEQ ID NO: 16), and/or HA Tag (YPYDVPDYA) (SEQ ID NO: 17)); and adoptively transferring a chimeric antigen receptor immune cell into a host subject comprising the cancer by administering to the subject a chimeric antigen receptor (CAR) immune cell (such as, for example, a CAR T cell, CAR Natural Killer Cell (CAR NK cell), CAR NK T cell, CAR Macrophage (CARMA)); wherein the CAR immune cell specifically targets and binds the synthetic antigen thereby killing the cancer cell, tumor associated fibroblast, regulatory T cells (Tregs), or myeloid-derived suppressor cell (MDSC).

It is understood and herein contemplated that the CAR immune cells (such as, for example, CAR T cells, CAR NK cells, CAR NK-T cells, and/or CARMA cells) administered in the disclosed methods of treating, reducing, decreasing, inhibiting, ameliorating, and/or preventing a cancer and/or metastasis can be synthetized ex vivo by transducing an immune cell (such as, for example, a T cell (including, but not limited to CD4 T cells and CD8 T cells), macrophage, NK cell, and/or NK T cell) with the chimeric antigen receptor. Said immune cells can come from a donor source such as the subject with cancer (autologous donor source) or a immunologically compatible donor (allogeneic donor source). Thus, also disclosed herein are methods of treating, reducing, decreasing, inhibiting, ameliorating, and/or preventing a cancer and/or metastasis further comprising obtaining an immune cell (such as, for example, T cell, Natural Killer (NK) cell, NK T cell, or macrophage) from a donor source (such as, for example, an immune cell obtained from an autologous or allogeneic donor. Also disclosed herein are methods of treating, reducing, decreasing, inhibiting, ameliorating, and/or preventing a cancer and/or metastasis of any preceding aspect further comprising transducing the immune cell with the chimeric antigen receptor. It is understood and herein contemplated that the chimeric antigen receptor can be made by any method known to those of skill in the art, including, but not limited to the incorporation of nucleic acid encoding the chimeric antigen receptor on any plasmid, viral vector, minicircle DNA, or mRNA disclosed herein.

In one aspect, disclosed herein are methods of treating, reducing, decreasing, inhibiting, ameliorating, and/or preventing a cancer and/or metastasis wherein the CAR immune cell is administered to the subject before, after, or concurrently with the transfection/transduction of the cancerous cell, tumor associated fibroblasts, regulatory T cells (Tregs), myeloid-derived suppressor cells (MDSCs), or extracellular matrix (ECM). For example, the CAR immune cell can be administered 1, 2, 3, 4, 5, 6, 7, 8, 9, 10, 15, 20, 25, 30, 35, 40, 45, 50, 55, 60, 65, 70, 75, 80, 85, 90, 120, 150, 180 minutes, 4, 5, 6, 7, 8, 9, 10, 11, 12, 13, 14, 15, 16, 17, 18, 19, 20, 21, 22, 23, 24, 30, 36, 42, 48, 54, 60, 66, 72 hours, 4, 5, 6, 7, 8, 9, 10, 11, 12, 13, 14, 15, 16, 17, 18, 19, 20, 21, 22, 23, 24, 25, 26, 27, 28, 29, 30, 31, 58, 59, 60, 61, 62, 90, 120 days, 4, 5, 6, 7, 8, 9, 10, 11, 12, 18, or 24 months before or after the transfection/transduction of the cancerous cell, tumor associated fibroblasts, myeloid-derived suppressor cells (MDSCs), regulatory T cells (Tregs), or extracellular matrix (ECM) with the synthetic antigen.

It is understood and herein contemplated that depending on the transfection/transduction system and expression system used, the expression of the synthetic antigen on the cell surface of the cancerous cell, tumor associated fibroblast, myeloid-derived suppressor cell (MDSC), regulatory T cells (Tregs), or extracellular matrix (ECM) can vary. For example, use of transposons, CRISPR/Cas9, TALENs, minicircle DNA, or lentiviral vectors can integrate the synthetic antigen into the host cell genome insuring long-term expression. However, other systems such as DNA plasmids have a more transient expression timeline. To counteract any transient expression of the synthetic antigen, the synthetic antigen can be transfected/transduced into the cancerous cell, tumor associated fibroblast, myeloid-derived suppressor cell (MDSC), regulatory T cells (Tregs), or extracellular matrix (ECM) 1, 2, 3, 4, 5, 6, 7, 8, 9, 10, 15, 20, 25, 30, 40, 45, 50, 55, 60, 65, 70, 75, 80, 85, 90, 95, 100 or more times until the tumor is gone. The interval of any subsequent transfection/transduction can occur 1, 2, 3, 4, 5 6, 7, 8, 10 times every, 1, 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, 72 hours, 4, 5, 6, 7, 8, 9, 10, 11, 12, 13, 14, 15, 16, 17, 18, 19, 20, 21, 22, 23, 24, 25, 26, 27, 28, 29, 30, 31, 58, 59, 60, 61, 62, 90, 120 days, 4, 5, 6, 7, 8, 9, 10, 11, 12, 18, or 24 months.

Similarly, it is understood and herein contemplated that a single administrative dose of CAR immune cells binding the synthetic antigen may not be sufficient to ablate a tumor in a subject. Thus, the CAR immune cell can be administered to the subject, 2, 3, 4, 5, 6, 7, 8, 9, 10, 15, 20, 25, 30, 40, 45, 50, 55, 60, 65, 70, 75, 80, 85, 90, 95, 100 or more times until the tumor is gone. The interval of any subsequent transfection/transduction can occur 1, 2, 3, 4, 5 6, 7, 8, 10 times every, 1, 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, 72 hours, 4, 5, 6, 7, 8, 9, 10, 11, 12, 13, 14, 15, 16, 17, 18, 19, 20, 21, 22, 23, 24, 25, 26, 27, 28, 29, 30, 31, 58, 59, 60, 61, 62, 90, 120 days, 4, 5, 6, 7, 8, 9, 10, 11, 12, 18, or 24 months.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 2:
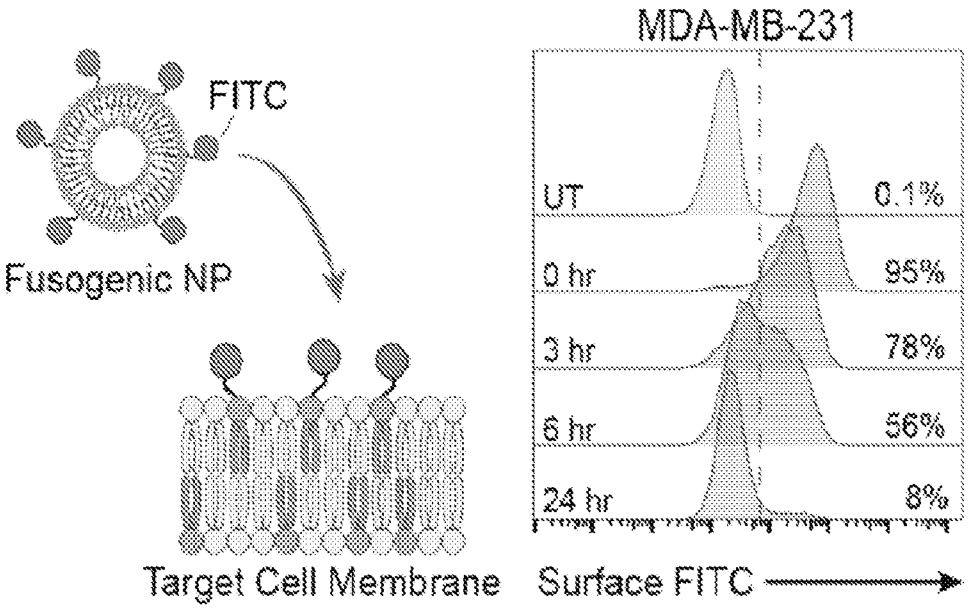
FIG. 2 shows the time course of expression of fluorescein (FITC) on the surface MDA-MB-231 tumor cells following delivery using membrane fusogenic liposomes.

1. Example 1: Achieving Synthetic Antigen Expression Using Non-Viral Approaches Synthetic antigen expression can be achieved by a variety of non-viral methods (e.g., membrane fusogenic liposomes, mRNA transfection, plasmid DNA transfection, mini-circle DNA transfection). In one embodiment, membrane fusogenic liposomes (MFLs) comprising of dimyristoyl phosphatidylcholine (DMPC), dioleoyloxypropyltrimethylammonium (DOTAP), and lipids conjugated to synthetic antigens (e.g., 1,2-Distearoyl-sn-glycero-3-phosphoethanolamine (DSPE)-polyethylene glycol (PEG)[2000]-Fluorescein isothiocyanate (FITC)) were prepared using the lipid film hydration method. MDA-MB-231 tumor cells are treated with 40 μM MFLs for 30 min at 37° C., washed, and stained for surface expression of the synthetic antigen, FITC. It was found that surface FITC expression was detected on the surface of MDA-MB-231 tumor cells for at least 6 hours (FIG. 2).

Figure 3:
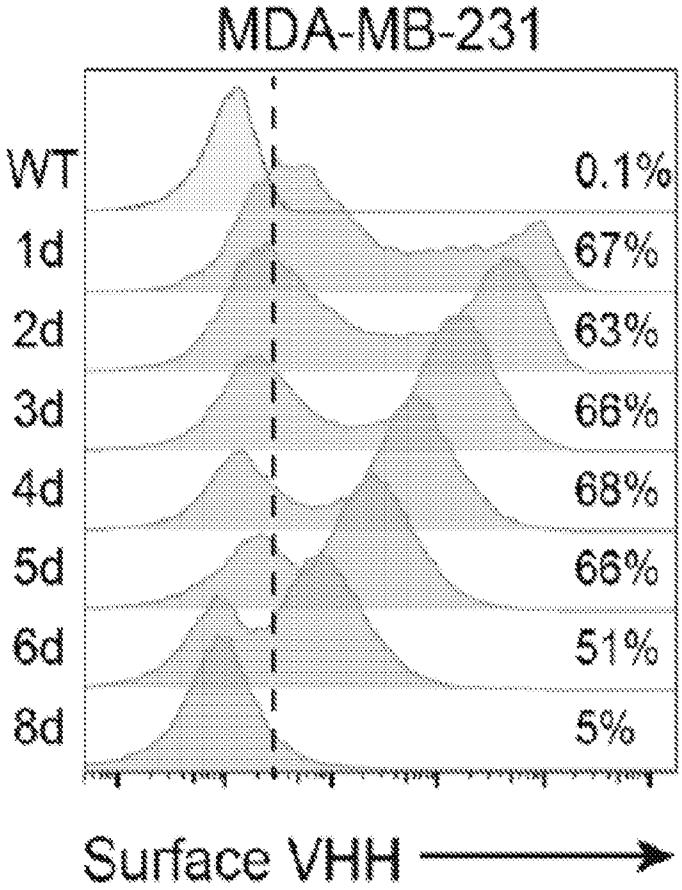
FIG. 3 shows the time course of expression of GPI-anchored RSV-F VHH on the surface MDA-MB-231 tumor cells following mRNA transfection.
Figure 4:
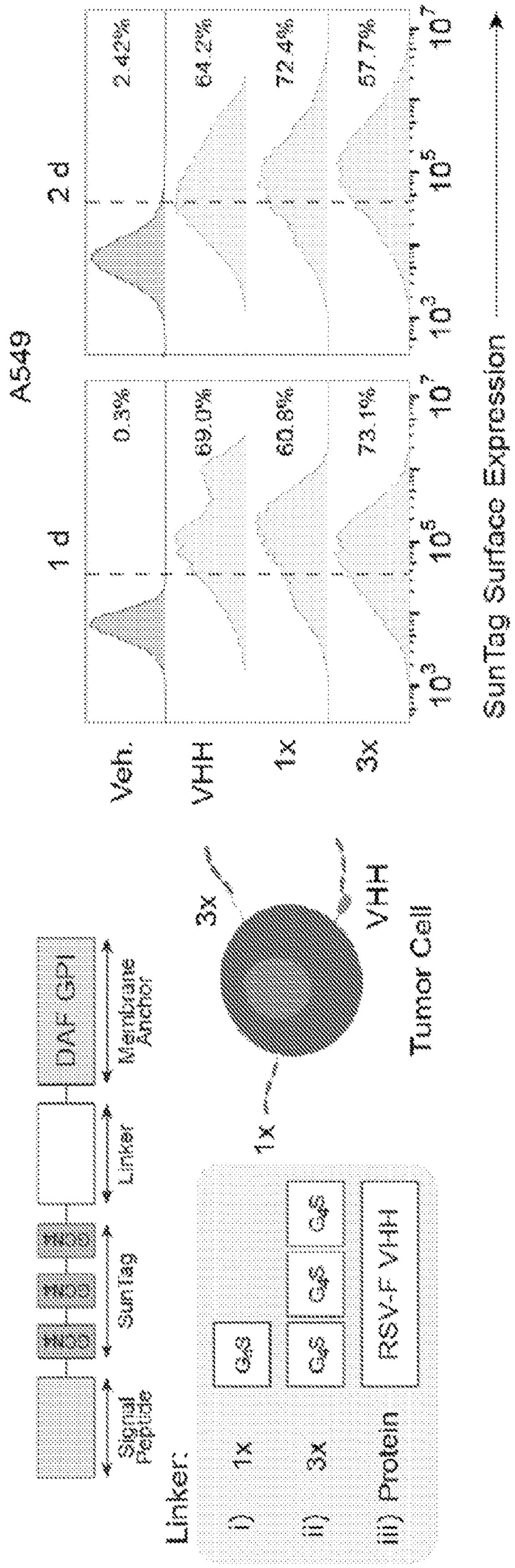
FIG. 4 shows the expression of GPI-anchored SunTag constructs with different linkers (i.e., 1×G4S, 3×G4S, or RSV-F VHH) on the surface of A549 tumor cells following mRNA transfection.

In another embodiment, non-viral synthetic antigen expression was achieved by mRNA transfection of glycosylphosphatidylinositol (GPI)-anchored camelid single domain antibody, respiratory syncytial virus F glycoprotein (RSV-F) VHH (SEQ ID: 11). Surface RSV-F VHH expression was detected on the surface of MDA-MB-231 tumor cells for at least 6 days (FIG. 3). In another embodiment, non-viral synthetic antigen expression was achieved by mRNA transfection of a GPI-anchored array of general control protein GCN4 (GCN4) peptides (i.e., "SunTag", SEQ IDs: 8-10). SunTag constructs were linked to the GPI-anchor using either a 1×G4S, 3×G4S, or RSV-F protein linker. SunTag expression on the surface of A549 tumor cells was detected 1 day and 2 days post mRNA transfection (FIG. 4).

Figure 5:
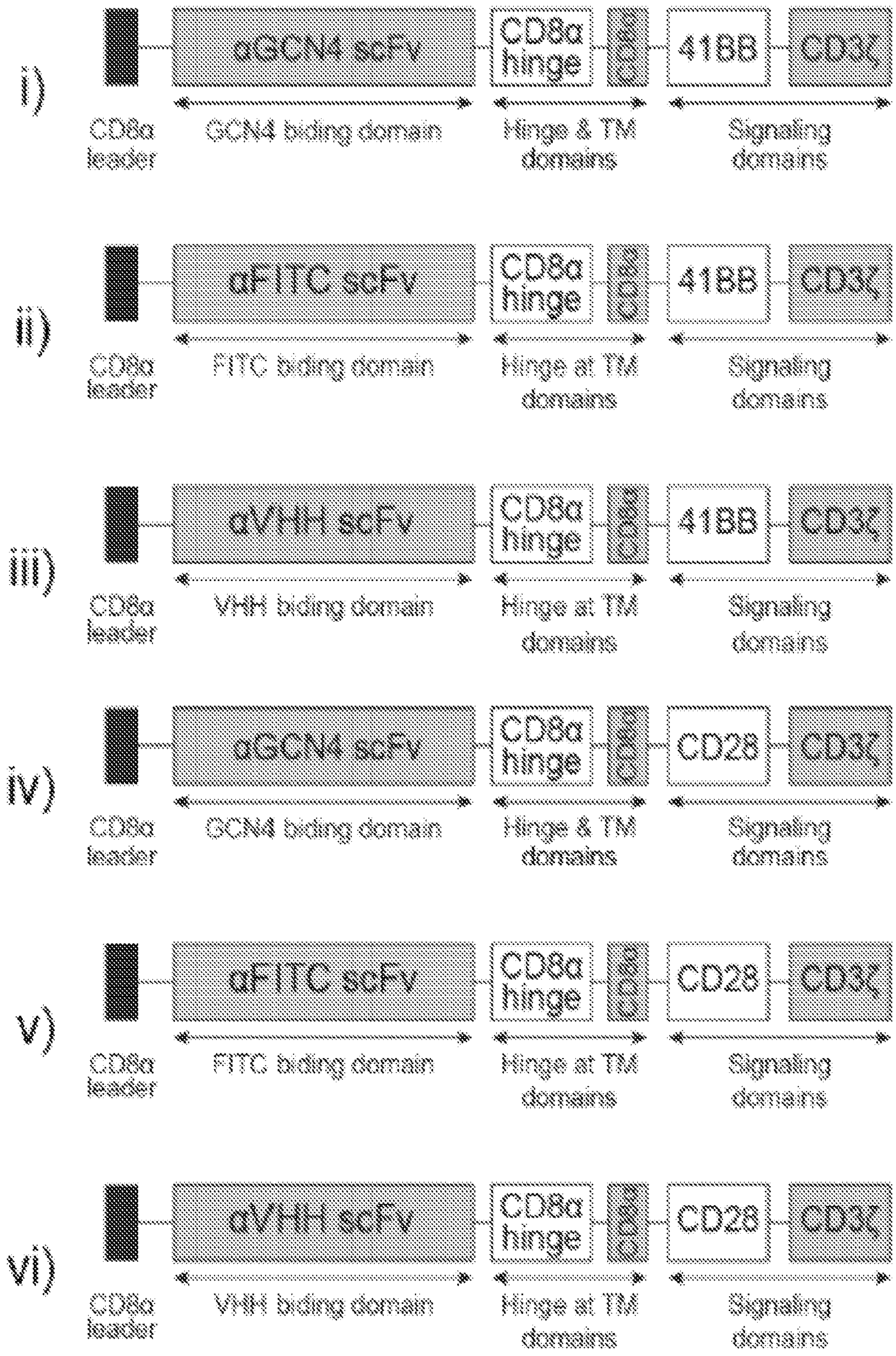
FIG. 5 shows examples of (i-iii) human CAR constructs and (iv-vi) murine CAR constructs for targeting synthetic antigens expressed on the surface of tumor cells (see SEQ IDs 1-2, 4-7)

2. Example 2: Chimeric Antigen Receptors (CARs) Targeted to Synthetic Antigens A variety of CARs can be used to target synthetic antigens (FIG. 5, Seq IDs 1,2, 4-7). CARs comprise an scFv targeted to a synthetic antigen (e.g., FITC, GCN4, VHH), a hinge (e.g., IgG4 hinge, CD8α hinge), a transmembrane domain (e.g., CD4 transmembrane domain, CD8 transmembrane domain, CD28 transmembrane domain, CD3ξ transmembrane domain), a costimulatory domain (e.g., a CD28 co-stimulatory domain, a 4-1 BB co-stimulatory domain, or both a CD28 co-stimulatory domain and a 4-1 BB co-stimulatory domain), and a CD3ξ signaling domain. In one embodiment, the scFv is targeted against fluorescein (FITC). In another embodiment, the scFv is targeted against GCN4 peptides. In another embodiment, the scFv is targeted against a camelid-derived single domain antibody (e.g., RSV-F VHH, Seq ID 3).

3. Example 3: Sensitizing Tumors to CAR-Mediated Cytotoxicity Using Synthetic Antigens a) Results

Figure 6:
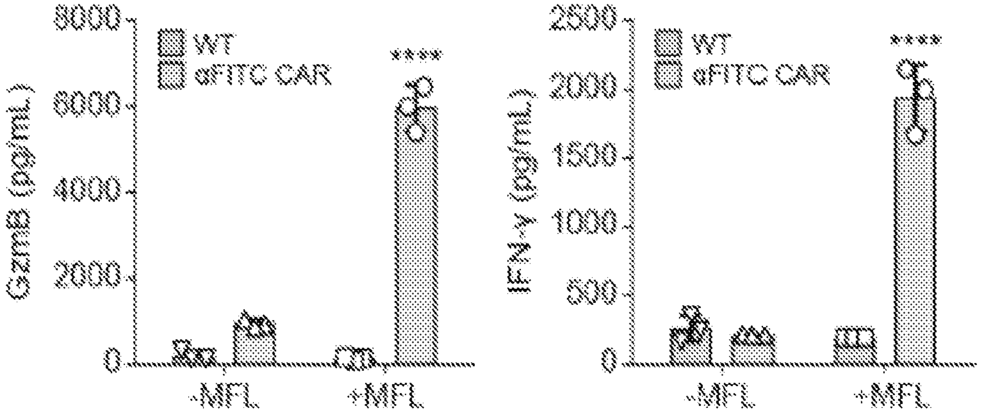
FIG. 6 shows granzyme B (GzmB) and interferon gamma (IFN-γ) secretion by αFITC CAR T or untransduced (WT) T cells following a 24 hr coculture with MFL-treated MDA-MB-231 cells at a 10:1 effector:target (E:T) ratio.
Figure 7:
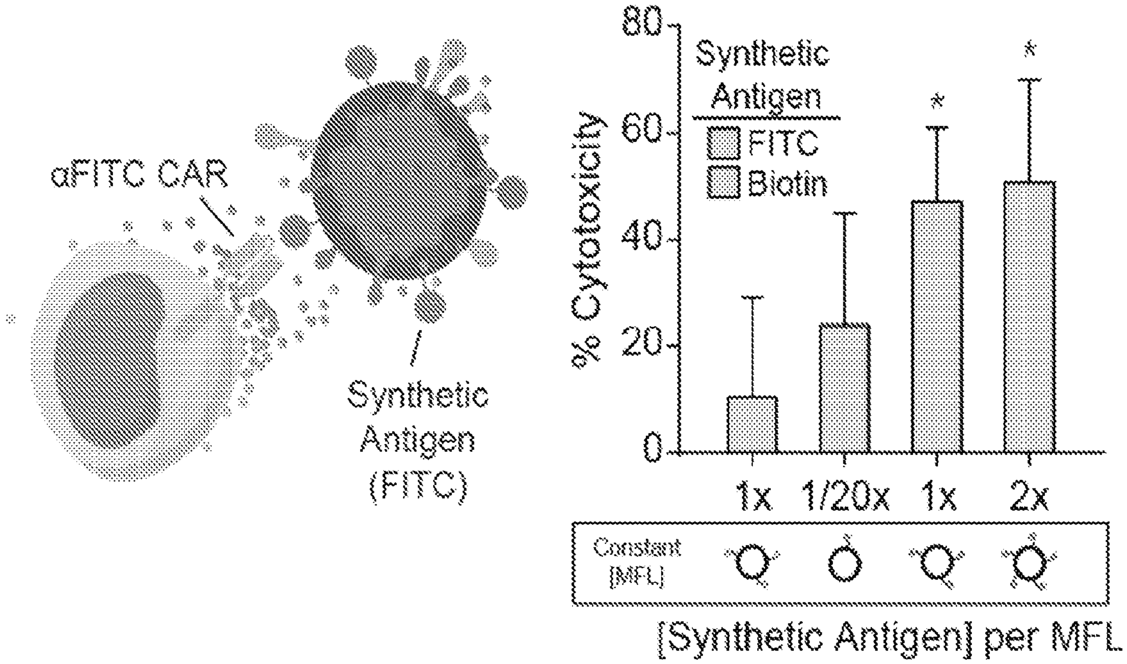
FIG. 7 shows killing of FITC-MFL or Biotin-MFL treated MDA-MB-231 tumor cells following a 24 hr coculture with αFITC CAR T or untransduced (WT) T cells at a 10:1 effector:target (E:T) ratio.
Figure 8:
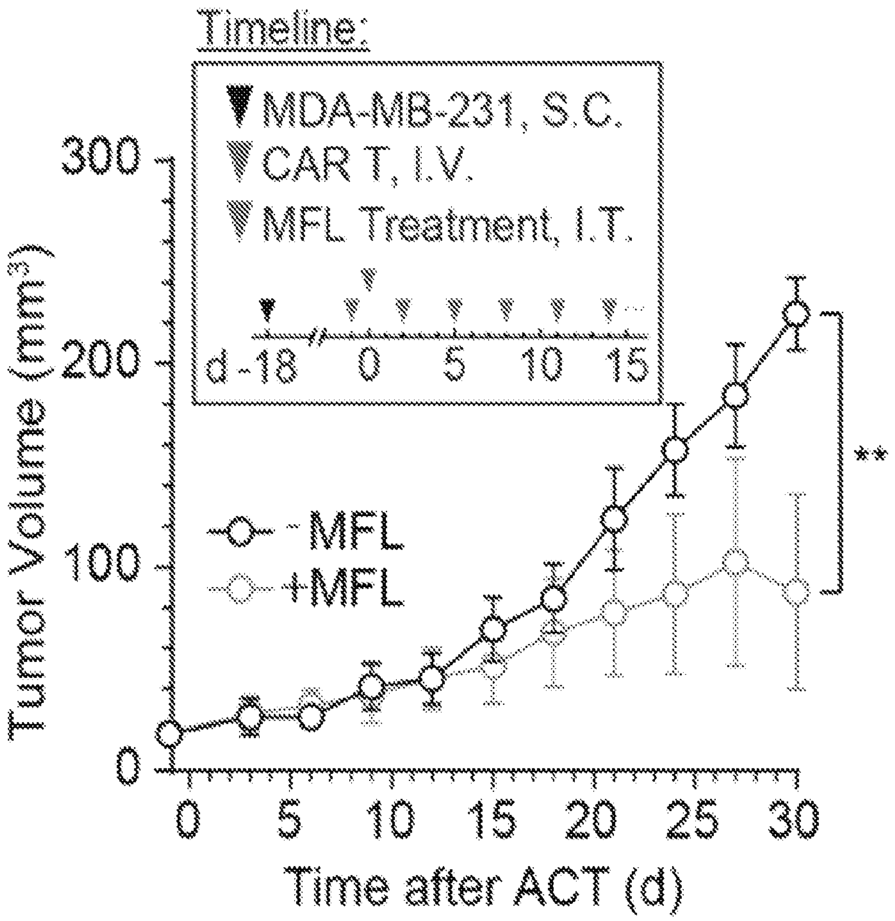
FIG. 8 shows tumor growth of MDA-MB-231 tumor-bearing mice treated with αFITC CAR T cells and either FITC MFLs or no MFLs. (n=3-4, mean±s.e.m, **p<0.01). The P-values was determined by an RM two-way ANOVA.

To sensitize solid tumors to CAR-mediated cytotoxicity, surface expression of synthetic antigens is first achieved by non-viral approaches (e.g., membrane fusogenic liposomes, nucleic acid transfection). In one embodiment, the delivery of the synthetic antigen, FITC, to the surface of MDA-MB-231 tumor cells using membrane fusogenic liposomes (MFLs) led to a significant increase in granzyme B (GzmB) and interferon gamma (IFN-γ) secretion when tumor cells were co-cultured with αFITC CAR T cells (**$p<0.0001$, FIG. 6), while WT T cells co-cultured with either treated or untreated tumor cells did not result in significant changes to IFN-γ ($p>0.05$, FIG. 6). In accordance with these results, CAR-mediated cytotoxicity increased significantly as the molar ratio of lipid-bound FITC was increased within the liposomes, and remained low when target cells were treated with an orthogonal antigen, biotin (FIG. 7). MDA-MB-231 tumor bearing mice administered αFITC CARs showed a significant delay in tumor growth when treated with FITC-MFLs intratumorally ($p<0.01$, FIG. 8).

Figure 9:
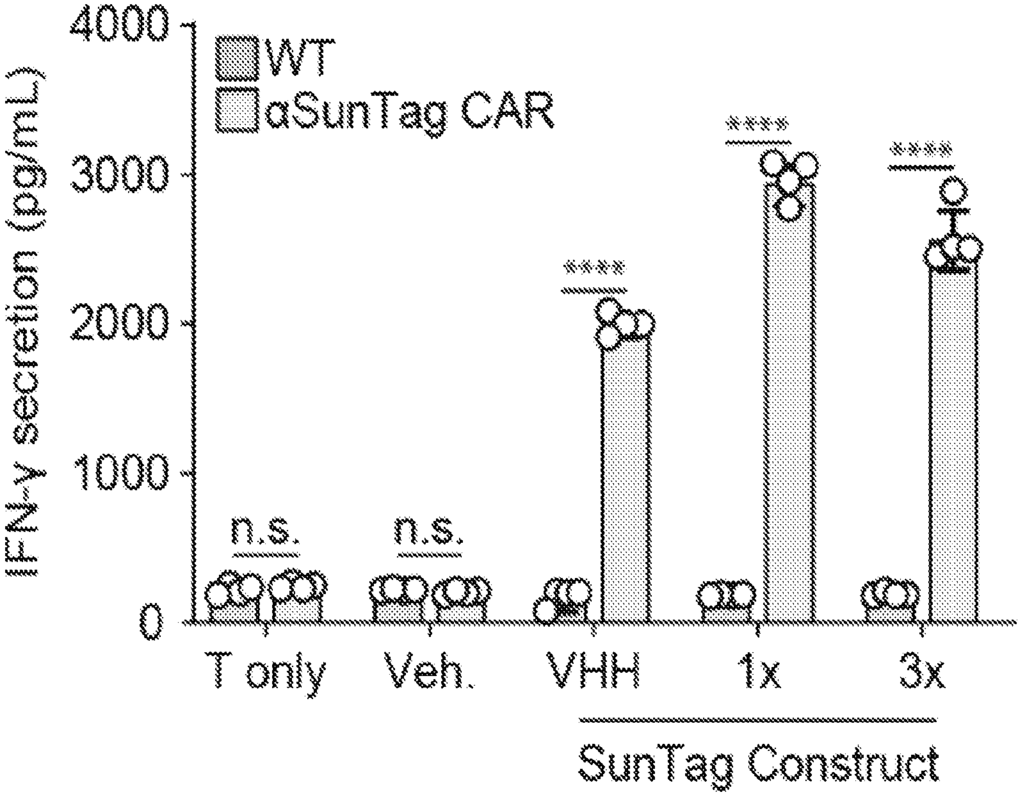
FIG. 9 shows interferon gamma (IFN-γ) secretion by αSunTag CAR T or untransduced (WT) T cells following a 24 hr coculture with A549 tumor cells expressing indicated SunTag constructs at a 1:1 effector:target (E:T) ratio.
Figure 10:
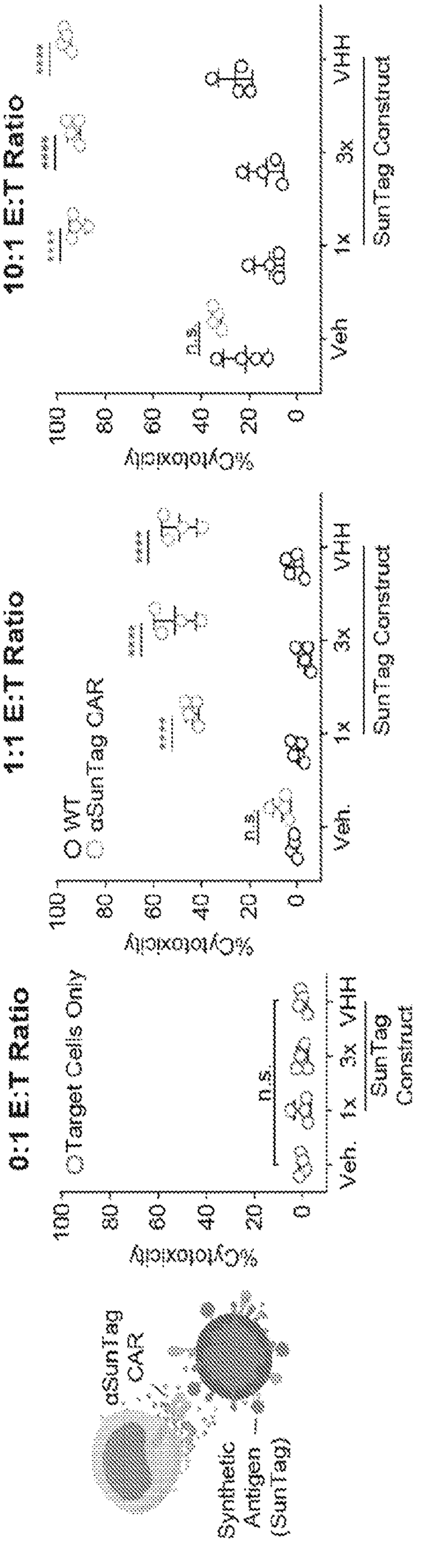
FIG. 10 shows killing of A549 tumor cells expressing SunTag constructs following a 24 hr coculture with αSunTag CAR T or untransduced (WT) T cells at indicated effector:target (E:T) ratios.
Figure 11:
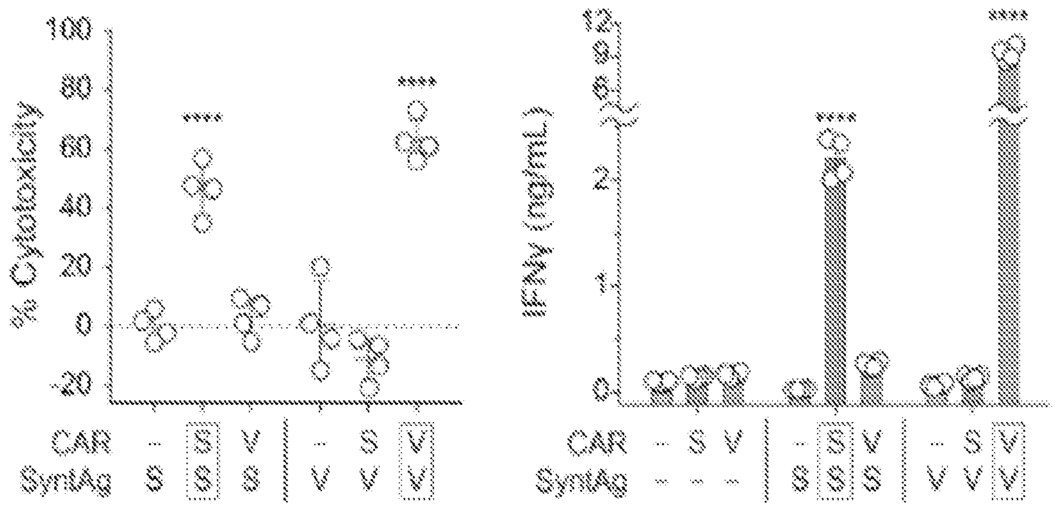
FIG. 11 shows killing of E0771 murine tumor cells expressing the synthetic antigen (SyntAg) constructs 1×SunTag(S) or VHH (V) following a 24 hr coculture with murine αSunTag CAR T, αVHH CAR T or untransduced (WT) T cells at a 2:1 effector:target (E:T) ratio (left panel). Interferon gamma (IFN-γ) secretion following the same 24-hr coculture (right panel).
Figure 12:
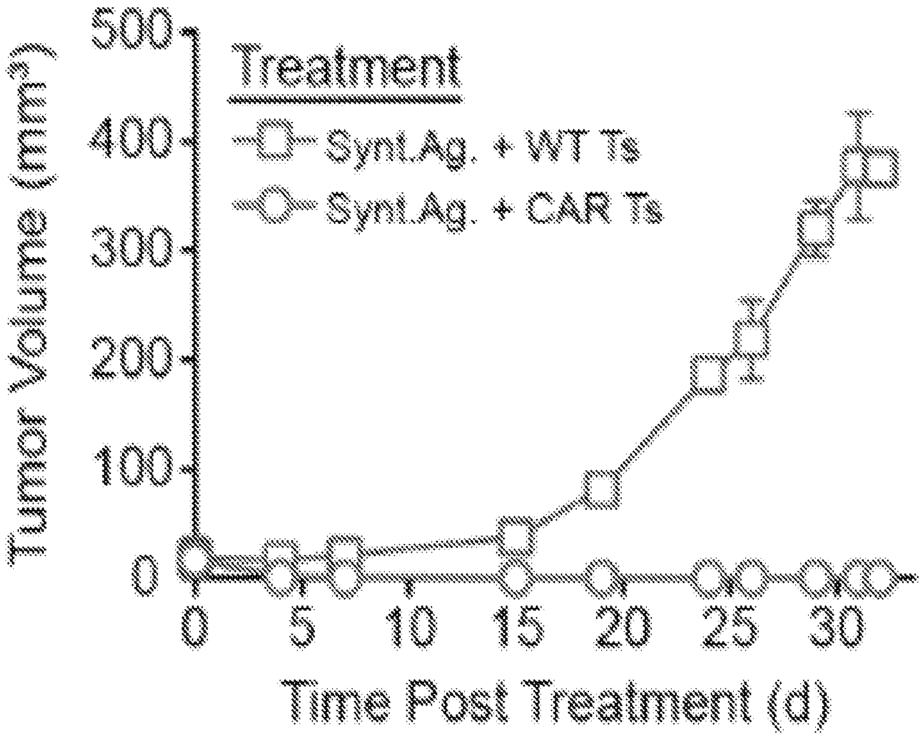
FIG. 12 shows tumor growth curves of E0771 tumor-bearing mice treated with the 1×SunTag synthetic antigen construct and either murine WT T cells or αSunTag CAR T cells. The synthetic antigen construct was delivered intratumorally via mRNA transfection and the T cells delivered intravenously.

In another embodiment, the delivery of the synthetic antigen, SunTag, to the surface of tumor cells by way of mRNA transfection led to a significant increase in IFN-γ secretion when co-cultured with αSunTag CAR T cells (**$p<0.0001$, FIG. 9), while CAR T cells alone or WT T cells co-cultured with either treated or untreated A549 tumor cells did not result in significant changes to IFN-γ ($p>0.05$, FIG. 9). In accordance with these results, CAR-mediated cytotoxicity increased significantly when either human (FIG. 10) or murine (FIG. 11**) αSunTag CAR T cells were cocultured with tumor cells transfected with SunTag mRNA constructs (*$p<0.05$, $p<0.01$, $p<0.0001$). Similarly, coincubation of the murine αVHH CAR with E0771 tumor cells transfected with the GPI-anchored VHH construct (SEQ ID: 11) led to significant cytoxicity and IFNγ production (FIG. 11). Intratumoral transfection of the 1×SunTag construct and systemic delivery of αSunTag CAR T cells led to a complete response in E0771 tumor bearing mice (FIG. 12). Complete responders were resistant to tumor rechallenge 19 days after initial treatment (FIG. 13**).

(1) Synthetic Antigens (SyntAg) are Robustly Expressed by Multiple Tumor Types Following mRNA Delivery In Vitro mRNA expression is transient, enables us to look at kinetics. We designed and tested several genetically encoded constructs, with different membrane anchors, linkers, and either the SunTag (3× repeat of the 19 aa epitope (EELLSKNYHLENEVARLKK) (SEQ ID NO: 12)) or VHH recognition domain (FIG. 14*a*). The constructes were trnafected into tumor cells an mRNA measured following transfection (FIG. 14*b*). We first compared two different membrane anchors, the GPI anchor and the CD4TM (FIG. 14*c*). We linked the well-characterized glycosylphosphatidylinositol (GPI) membrane anchor sequence from the decay accelerating factor (DAF) or the CD4 transmembrane (CD4TM)

domain to the VHH recognition domain using one repeat of a flexible G4S peptide. GPI-anchored VHH demonstrated greater surface intensity (median fluorescence intensity). Since antigen density is key for CAR T cell responses, we moved forward with GPI-anchor. We next compared different linkers to the recognition domain (FIG. 14*d*). We linked the GPI anchor to the SunTag recognition domain with either a 1× repeat of the flexible $G_4S$ peptide, a 3× repeat of $G_4S$, or a longer, protein linker mimicked by VHH. All three constructs became undetectable by flow cytometry 3 days post transfection. Finally, we compared recognition domains (FIG. 14*e*). We compared surface expression kinetics of GPI-anchored SunTag vs. GPI-anchored VHH across multiple cell lines (human: A549; murine: E0771, MC38). GPI-anchored SunTag persisted on the surface with a half-life of ~1d, while GPI-anchored VHH was characterized with a half-life of ~5d. GPI-anchored VHH was detected on the surface of multiple tumor lines, both human and murine, up to 7d post transfection (FIG. 14*e*, FIG. 3). For comparison, the Kb-SIINFEKL (SEQ ID NO: 13) pMHC complex has a half-life of ~8 hrs on the surface of MC38 cells, while various human immune cells such as DCs, B cells, and monocytes have a half-life HLA-A*02:01-gp100154-162 of 1.5-22.5 hrs.

(2) αSunTag and αVHH CARs Recognize and Kill Tumor Cells Expressing their Cognate Synthetic Antigen In Vitro To target synthetic antigens SunTag and VHH, we designed both murine and human CAR T cell constructs (FIG. 16*a-b* and FIG. 17*a*). Expression of new CAR constructs was validated in both murine and human T cells (FIG. 16*c* and FIG. 17*b*). CAR T cells activate when they see their cognate synthetic antigen (FIG. 16*c*). When we co-culture SyntAg-treated tumor cells with CAR T cells, we see a significant increase in IFNg and cytotoxicity only when the cognate antigen. (FIGS. 16*f-g* and FIGS. 17*c-f*).

(3) αVHH CAR T Cells are not Toxic

A key concern with new CAR T cell development is the potential for toxicity in off-tumor tissues. No elevations in various hematological parameters, including renal function (urea nitrogen and creatinine), proteins (total protein), and liver enzymes (AST, ALT) in mice treated with CARs compared to controls after 7 days. This indicates there are no acute compromise in liver function (+renal function) after 7 days. (FIG. 18*a* and FIG. 19). VHH antigen on its own does not lead to tumor shrinkage (FIG. 18*b* and FIG. 20).

(4) VHH CARs Treatment Enhances Antitumor Response to Solid Tumors in Immunocompetent Mice 137. Mice bearing MC38-VHH tumors were treated with αVHH CAR T cells (FIG. 21*a*). We monitored tumor growth in mice following ACT. We observed that ACT of αVHH CAR T cells into mice with VHH-expressing tumors delays tumor growth (FIG. 21*b*). Additionally, VHH CAR T cell treatment recruits tumor-reactive endogenous T cells specific for the untargeted neoepitope Reps1 (FIGS. 21*c*-21*e*).

Next we used a tumor challenge model to determine if αVHH-CAR treated mice are resistant to tumor challenge with wildtype tumors. Mice bearing E0771-VHH tumors (FIG. 22A) were treated with αVHH-CAR T cells. We observed that VHH CAR T cell treatment leads to a complete response in 3/4 mice (FIG. 22*b*). We further observed that complete responders are resistant to rechallenge with wildtype TNBC line, E0771. (FIG. 22*c*) and in feact, survival is enhanced (FIG. 22*d*).

(5) AAV-Mediated Expression of VHH in a Murine Model of TNBC Followed by Treatment with a VHH CAR T Cells Leads to a Potent Antitumor Response To see the effect of AAV-mediated expression of VHH in a murine model of TNBC we induced expression of VHH in wildtype, TNBC tumor using AAV2 (FIG. 23*a*) or wildtype MC38 (FIG. 24). Tumors expressed VHH following intratumoral injection of AAV2-VHH (FIG. 23*b*, and FIG. 24). We observed that combination treatment of AAV2-VHH and αVHH CAR T cells leads to a potent antitumor response (FIG. 23*c* and FIG. 25) b) METHODS (1) Animals Six- to twelve-week old female mice were used for all experiments. C57BL/6J mice were purchased from the Jackson Laboratory™ (000664, Bar Harbor, ME, USA) and NSG mice were bred in-house at the Georgia Tech Physical Research Laboratory using breeding pairs purchased from the Jackson Laboratory™ (005557). All protocols were approved by the Georgia Tech Institutional Animal Care and Use Committee (IACUC). Tumor dimensions were measured with calipers in three dimensions and reported as an ellipsoidal volume.

(2) Cell Culture and Generation of Cell Lines

Human embryonic kidney (HEK) 293T cells were obtained from ATCC, and the murine MC38 colon carcinoma cells were a kind gift from the NCI. HEK293T and MC38 cells were maintained in Dulbecco's Modified Eagle's Medium (DMEM, Life Technologies™ 11995073) supplemented with 10% fetal bovine serum (FBS, Thermo Fisher™ 16140071) and 1% penicillin/streptomycin (Life Technologies™, 15140-122). E0771 cells were cultured in RPMI-1640 (Corning 10-040-CV) supplemented with 10% FBS and 1% penicillin/streptomycin. E0771-VHH and MC38-VHH cell lines were generated by lentiviral transduction of wildtype E0771 or MC38 cells, respectively, with the VHH gene driven by the EF1α core promoter in a LeGO-C lentiviral backbone (Addgene™ #27348). VHH+ cells were single cell sorted using the BD FACS Fusion in the Georgia Institute of Technology's Cellular Analysis Core. Similarly, E0771-Thy1.1 and MC38-Thy1.1 were generated by lentiviral transduction of the Thy1.1 gene, single cell sorted, and stably maintained using Blasticidin (Thermo Fisher™ A1113903). All cells were cultured at 37° C. in 5% $CO_2$.

(3) Construction and Murine CARs

To obtain the anti-VHH scFv sequence, REmAb® Protein Sequencing with WILD™ analysis (Rapid Novor, Ontario, Canada) was performed on the MonoRab™ Rabbit Anti-Camelid VHH Antibody (Clone 96A3F5, Genscript™ #A01860). The CAR is composed of a mouse CD8 signal peptide, antigen-specific scFv (anti-GCN4 scFv Cho J H, et al. *Cell* (2018); for SunTag and anti-VHH scFv for VHH), mouse CD8α hinge and transmembrane domain, as well as the mouse CD28 and CD3ξ intracellular domains. The murine CAR constructs were designed to co-express a fluorescent reporter (eGFP) using the T2A sequence and were generated using DNA fragments (custom order from Eurofins Genomics). CAR constructs were cloned into a retroviral vector (pMKO.1, kindly provided by Dr. Koichi Araki) using the EcoRI and NotI restriction sites.

(4) Lenti- and Retroviral Production

Plasmid DNA was purified using with the E.Z.N.A.® Endo Free Plasmid Maxi Kit (Omega Bio-Tek D6926-03). Recombinant retrovirus was made by co-transfection with pCL-Eco (Imgenex, San Diego, CA) and pMKO.1 retroviral vectors encoding for murine CARs in HEK293T cells using TransIT-293 (MIR2705, Mirus). Virus containing supernatant was collected 48 hrs later, filtered through a 0.45 μm syringe filter (Pall Acrodisc, #4654) to remove cell debris, mixed with Retro-Concentin Virus Precipitation Solution (RV100A-1, System Biosciences, Palo Alto, CA), and stored overnight at 4° C. The next day, retroviral mixture was concentrated at 1500×g for 30 min at 4° C., resuspended in murine T cell media, and immediately used for transduction of primary murine T cells.

Lentivirus was produced by co-transfection of lentiviral expression plasmids with psPAX2 (Addgene™ #12260) and pMD2.G (Addgene™ #12259) using TransIT-LT1 transfection reagent (Mirus Bio MIR2300) and HEK293T cells. Viral supernatant collected after 48 hrs, was concentrated using PEG-It™ Virus Precipitation Solution (LV825A-1, System Biosciences, Palo Alto, CA) following the manufacturer's protocol and stored at −80° C. until use.

(5) AAV Production for In Vivo Delivery

The GPI-anchored VHH gene was synthesized as a custom DNA fragment (Eurofins Genomics). To generate AAV expression vectors, the VHH, GFP or Fluc genes were amplified by PCR and placed under the control of a CMV promoter via restriction enzyme cloning using EcoRI and BamHI in the pAAV-CMV expression vector (Takara™ #6230). Recombinant AAV2 vector was prepared using an AAVpro Helper Free System (Takara™ #6230). To produce the AAV9 or AAVDJ serotypes, the pRC-mi342 plasmid encoding for the AAV2 Rep and Cap genes was replaced with either the AAV9 (Genemedi) or AAV-DJ (Cell BioLabs #VPK-420-DJ) rep-cap plasmids. AAV particles were produced by co-transfecting HEK293T cells with the packaging plasmids (pRC and pHelper) and either pAAV-VHH, pAAV-Fluc, or pAAV-GFP using the calcium phosphate transfection method (Takara™ #631312). Cells were collected 72 h post transfection and AAV particles were extracted and purified using the AAVpro Purification Kit (Takara™ #6232) following the manufacturer's instructions. Genomic copy number (GC) of AAVs were determined by qPCR using AAVpro Titration Kit Ver. 2 (Takara™ #6233).

(6) Primary Murine CAR T Cell Production

Cells from Pmel-1 or P14 mouse spleens and lymph nodes were harvested by gently dissociating the tissues using frosted glass slides. Cells were centrifuged at 1000×g for 5 min and resuspended in 1×RBC lysis buffer (420301, Biolegend™) for 5 min at 4° C. Following the addition of 1×PBS to quench the lysis reaction, cells were centrifuged again, resuspended in complete murine T cell media (cTCM; RPMI+10% FBS+1% Pen/Strep+1×NEAA+1× Sodium Pyruvate+50 μM Beta-mercaptoethanol) containing 100 IU/mL of recombinant human IL-2 (TECIN™ Teceleukin, Bulk Ro 23-6019, National Cancer Institute, Frederick, MD), and passed through a 40 μm cell strainer (732-2757, VWR) prior to counting. Cells were cultured in the presence of either 1 μM human $gp100_{25-33}$ (Pmel-1) or $gp33_{33-41}$ (P14). On day 2, cells were collected, washed, and resuspended at $8\times10^6$ cells/mL in concentrated retroviral supernatant supplemented with 100 IU/mL hIL2 and 8 μg/mL polybrene. Spinfection was performed in a U-bottom 96-well plate at 2,000×g for 90 min at 32° C. Transduced cells were resuspended and maintained at $1\times10^6$ cells/mL in fresh cTCM supplemented with 100 IU/mL hIL-2 and passaged daily until use for in vitro or in vivo experiments on day 6. CAR expression was evaluated by surface staining with biotinylated antigen (biotinylated VHH, Chromotek #gtb-250; biotinylated GCN4, synthesized in-house) followed by a secondary stain with streptavidin-APC (Thermo Fisher™ #S868). For staining, biotinylated SunTag was synthesized on Rink Amide ProTide (LL) resin using CEM Liberty Blue, including Fmoc deprotection in piperidine, amino acid coupling in N,N'-diisopropylcarbodiimide and Oxyma Pure, N-terminal biotinylation by biotin p-nitrophenyl ester in presence of Oxyma Pure. The peptide was cleaved off resin in trifluoroacetic acid, precipitated in diethyl ether, dried overnight, and resuspended in 10 mg/mL in water for storage at −20° C.

(7) In Vitro Transcription of Synthetic Antigen mRNA mRNA was produced. Briefly, plasmids were linearized with NotI-HF (New England Biolabs) overnight at 37° C., purified the following day by sodium acetate precipitation and subsequently rehydrated with nuclease-free water. In vitro transcription (IVT) was performed using the HiScribe™ T7 Kit (NEB) following the manufacturer's instructions using N1-methylpseudouridine-5'-triphosphate. The resulting RNA was treated with DNase for 30 min and purified using lithium chloride precipitation. RNAs were capped using guanylyl transferase and 2'-O-methyltransferase (Aldevron), purified by lithium chloride precipitation, treated with alkaline phosphatase (NEB), and re-purified. The concentration of the purified mRNA was measured using a Nanodrop and subsequently stored at −80° C. at stock concentrations of 1-4 mg/mL. Purified RNA product was analyzed by gel electrophoresis to ensure purity.

(8) Therapy Studies

C57BL6/J mice were shaved and inoculated with either $1\times10^6$ MC38-VHH, $5\times10^5$ E0771-VHH, or $5\times10^5$ E0771-wt tumor cells. For E0771 experiments, cells were resuspended in 30 μL PBS (−/−) and implanted i.d. in the left mammary fat pad (fourth). For MC38 experiments, cells were resuspended in 100 μL PBS (−/−) and implanted s.c. into the left flank. Tumor burden, quantified as 0.52×length×width×depth, was monitored until average tumor volume was approximately 100 $mm^3$ before initiating treatment. On treatment day, mice were sublethally irradiated with 500 cGy and $5\times10^6$ CAR transduced pmel-1 splenocytes were adoptive transferred via tail vein injections. Recombinant human IL-2 (rhIL-2) was administered intraperitoneally twice daily for 3 days. Mice were classified as complete (CR) or partial responders (PR), or as having progressive disease (PD) or stable disease (SD) based on the RECIST criteria. On Day 18 post ACT, MC38-VHH tumors and lymph nodes were isolated for flow cytometry analysis. For E0771-VHH experiments, CRs were rechallenged 45 days after initial treatment with $5\times10^5$ synthetic antigen negative (E0771-wt) tumor cells in the right mammary fat pat (fourth).

(9) Flow Cytometry Analysis of T Cells In Vivo

All antibodies for flow cytometry were purchased from Biolegend™. Single cell suspensions from spleens and lymph nodes were prepared by homogenizing the tissue between the frosted end of glass slides. Homogenized cells were passed through a 40 μm cell strainer, depleted of red blood cells using 1×RBC lysis buffer (Biolegend™ 420302). For tumors, less than 1 g of MC38-VHH tumors were enzymatically and mechanically dissociated using the Mouse Tumor Dissociation Kit (Miltenyi, 130-096-730) and gentleMACS Dissociator (Miltenyi, 130-093-235). TILs were then isolated from the single cell suspension using a density gradient with Percoll Centrifugation Media (VWR, 17-5445-01) and DMEM Media (10% FBS, 1% Penstrep) at a 44:56 volume ratio. All antibodies were used for staining at 1:100 dilution from stock concentrations. For surface staining, cells were blocked with anti-Fc receptor anti-CD16/CD32, and then stained with surface marker antibodies in FACS Buffer (1×DPBS, 2% FBS, 1 mM EDTA, 25 mM HEPES). Fixation was performed using eBioscience Intracellular Fixation & Permeabilization Buffer Set following the manufacturer's instructions (Thermo, 88-8823-88). Counting beads (Thermo, C36950) were added to each sample of stained cells prior to analysis by the LSR Fortessa Flow Cytometer (BD).

(10) Liver Function Analysis

Blood was drawn via the jugular vein and collected in either. Blood samples were obtained Blood was taken via jugular vein. Serum was separated, and samples were sent for blood chemistry testing at Antech Diagnostics. Blood samples were collected in serum separator tubes

(11) Statistical Analysis

Appropriate statistical analyses were performed using GraphPad Prism (*P<0.05, P<0.01, *P<0.001, ****P<0.001). Central values represent mean and error bars depict s.e.m. Flow cytometry data were analyzed using FlowJo X (FlowJo, LLC). Power analyses were performed using G*Power 3.1 (HHUD).

E. REFERENCES hn, S., Woo, J. W., Lee, K. & Park, S. Y. HER2 status in breast cancer: changes in guidelines and complicating factors for interpretation. *J Pathol Transl Med* 54, 34-44, doi:10.4132/jptm.2019.11.03 (2020).

Blanchard, E. L. et al. Treatment of influenza and SARS-COV-2 infections via mRNA-encoded Cas13a in rodents. *Nature Biotechnology, doi:*10.1038/s41587-021-00822-w (2021).

Bushnell, G. G. et al. Breast cancer dormancy: need for clinically relevant models to address current gaps in knowledge. *npj Breast Cancer* 7, 66, doi:10.1038/s41523-021-00269-x (2021).

Cho, J. H., Collins, J. J. & Wong, W. W. Universal Chimeric Antigen Receptors for Multiplexed and Logical Control of T Cell Responses. *Cell* 173, 1426-1438.e1411, doi:10.1016/j.cell.2018.03.038 (2018).

Choi, B. D. et al. CAR-T cells secreting BiTEs circumvent antigen escape without detectable toxicity. *Nature Biotechnology* 37, 1049-1058, doi:10.1038/s41587-019-0192-1 (2019).

Du, Y., Pattnaik, A. K., Song, C., Yoo, D. & Li, G. Glycosyl-phosphatidylinositol (GPI)-anchored membrane association of the porcine reproductive and respiratory syndrome virus GP4 glycoprotein and its co-localization with CD163 in lipid rafts. *Virology* 424, 18-32

Fried, S. et al. Early and late hematologic toxicity following CD19 CAR-T cells. *Bone Marrow Transplantation* 54, 1643-1650, doi:10.1038/s41409-019-0487-3 (2019).

Hou, A. J., Chen, L. C. & Chen, Y. Y. Navigating CAR-T cells through the solid-tumour microenvironment. *Nature Reviews Drug Discovery* 20, 531-550, doi:10.1038/s41573-021-00189-2 (2021).

Landgraf, K. E. et al. convertibleCARs: A chimeric antigen receptor system for flexible control of activity and antigen targeting. *Communications Biology* 3, 296, doi:10.1038/s42003-020-1021-2 (2020).

Lee, Y. G. et al. Regulation of CAR T cell-mediated cytokine release syndrome-like toxicity using low molecular weight adapters. *Nat Commun* 10, 2681, doi:10.1038/s41467-019-10565-7 (2019).

Lee, Y. G. et al. Use of a Single CAR T Cell and Several Bispecific Adapters Facilitates Eradication of Multiple Antigenically Different Solid Tumors. *Cancer Research* 79, 387-396, doi:10.1158/0008-5472.Can-18-1834 (2019).

Leko, V. & Rosenberg, S. A. Identifying and Targeting Human Tumor Antigens for T Cell-Based Immunotherapy of Solid Tumors. *Cancer Cell* 38, 454-472, doi:10.1016/j.ccell.2020.07.013 (2020).

Lohmueller, J. J., Ham, J. D., Kvorjak, M. & Finn, O. J. mSA2 affinity-enhanced biotin-binding CAR T cells for universal tumor targeting. *Oncoimmunology* 7, e1368604, doi:10.1080/2162402x.2017.1368604 (2017).

Ma, L. et al. Enhanced CAR& #x2013; T cell activity against solid tumors by vaccine boosting through the chimeric receptor. *Science* 365, 162-168, doi:doi:10.1126/science.aav8692 (2019).

Millar, D. G. et al. Antibody-mediated delivery of viral epitopes to tumors harnesses CMV-specific T cells for cancer therapy. *Nature Biotechnology* 38, 420-425, doi:10.1038/s41587-019-0404-8 (2020).

Miller, I. C. et al. Enhanced intratumoural activity of CAR T cells engineered to produce immunomodulators under photothermal control. *Nature Biomedical Engineering, doi:*10.1038/s41551-021-00781-2 (2021).

Morgan, R. A. et al. Case report of a serious adverse event following the administration of T cells transduced with a chimeric antigen receptor recognizing ERBB2. *Mol Ther* 18, 843-851, doi:10.1038/mt.2010.24 (2010).

Nahas, G. et al. Persistent Cytopenias after Chimeric Antigen Receptor T-Cell Immunotherapy for CD19+Aggressive Lymphoma: A Single Institution Experience. *Biology of Blood and Marrow Transplantation* 25, S180.

Nickells, M. W., Alvarez, J. I., Lublin, D. M. & Atkinson, J. P. Characterization of DAF-2, a high molecular weight form of decay-accelerating factor (DAF; CD55), as a covalently cross-linked dimer of DAF-1. *J Immunol* 152, 676-685 (1994).

Park, A. K. et al. Effective combination immunotherapy using oncolytic viruses to deliver CAR targets to solid tumors. *Science Translational Medicine* 12, eaaz1863, doi:doi:10.1126/scitranslmed.aaz1863 (2020).

Ramakrishna, S., Barsan, V. & Mackall, C. Prospects and challenges for use of CAR T cell therapies in solid tumors. *Expert Opinion on Biological Therapy* 20, 503-516, doi:10.1080/14712598.2020.1738378 (2020).

Rodgers, D. T. et al. Switch-mediated activation and retargeting of CAR-T cells for B-cell malignancies. *Proceedings of the National Academy of Sciences* 113, E459-E468, doi:10.1073/pnas.1524155113 (2016).

Roybal, Kole T. et al. Precision Tumor Recognition by T Cells With Combinatorial Antigen-Sensing Circuits. *Cell* 164, 770-779.

Schwartz, L. H. et al. RECIST 1.1-Update and clarification: From the RECIST committee. *Eur J Cancer* 62, 132-137, doi:10.1016/j.ejca.2016.03.081 (2016).

Tanenbaum, M. E., Gilbert, L. A., Qi, L. S., Weissman, J. S. & Vale, R. D. A protein-tagging system for signal amplification in gene expression and fluorescence imaging. *Cell* 159, 635-646, doi:10.1016/j.cell.2014.09.039 (2014).

Tiwari, P. M. et al. Engineered mRNA-expressed antibodies prevent respiratory syncytial virus infection. *Nat Commun* 9, 3999, doi:10.1038/s41467-018-06508-3 (2018).

Viswanathan, S. et al. High-performance probes for light and electron microscopy. *Nature Methods* 12, 568-576, doi: 10.1038/nmeth.3365 (2015).

Won, K.-A. & Spruck, C. Triple-negative breast cancer therapy: Current and future perspectives (Review). *Int J Oncol* 57, 1245-1261, doi:10.3892/ijo.2020.5135 (2020).

Wudhikarn, K. et al. Infection during the first year in patients treated with CD19 CAR T cells for diffuse large B cell lymphoma. *Blood Cancer Journal* 10, 79, doi:10.1038/s41408-020-00346-7 (2020).

Zehn, D., Cohen, C. J., Reiter, Y. & Walden, P. Extended presentation of specific MHC-peptide complexes by mature dendritic cells compared to other types of antigen-presenting cells. *European Journal of Immunology* 34, 1551-1560.

F. Sequences

SEQ ID 1: Murine αSunTag (αGCN4) CAR, Amino Acid Sequence:
```
MASPLTRFLSLNLLLLGESIILGSGEAGPDIVMTQSPSSLSASVGDRVTITCRSSTGAVTTS
NYASWVQEKPGKLFKGLIGGTNNRAPGVPSRFSGSLIGDKATLTISSLQPEDFATYFCAL
WYSNHWVFGQGTKVELKRGGGGSGGGGSGGGGSSGGGSEVKLLESGGGLVQPGGSL
KLSCAVSGFSLTDYGVNWVRQAPGRGLEWIGVIWGDGITDYNSALKDRFIISKDNGKN
TVYLQMSKVRSDDTALYYCVTGLFDYWGQGTLVTVSSTTTKPVLRTPSPVHPTGTSQP
QRPEDCRPRGSVKGTGLDFACDIYIWAPLAGICVALLLSLIITLICYHRSRNSRRNRLLQS
DYMNMTPRRPGLTRKPYQPYAPARDFAAYRPSRSAETAANLQDPNQLYNELNLGRREE
YDVLEKKRARDPEMGGKQQRRRNPQEGVYNALQKDKMAEAYSEIGTKGERRRGKGH
DGLYQGLSTATKDTYDALHMQTLA
```

SEQ ID 2: Murine αFITC CAR, Amino Acid Sequence:
```
MASPLTRFLSLNLLLLGESIILGSGEAGVKLDETGGGLVQPGGAMKLSCVTSGFTFGHY
WMNWVRQSPEKGLEWVAQFRNKPYNYETYYSDSVKGRFTISRDDSKSSVYLQMNNLR
VEDTGIYYCTGASYGMEYLGQGTSVTVSGGGGSGGGGSGGGGSGGGGSDVVMTQTPL
SLPVSLGDQASISCRSSQSLVHSNGNTYLRWYLQKPGQSPKVLIYKVSNRVSGVPDRES
GSGSGTDFTLKINRVEAEDLGVYFCSQSTHVPWTFGGGTKLEIKTTTKPVLRTPSPVHPT
GTSQPQRPEDCRPRGSVKGTGLDFACDIYIWAPLAGICVALLLSLIITLICYHRSRNSRRN
RLLQSDYMNMTPRRPGLTRKPYQPYAPARDFAAYRPSRSAETAANLQDPNQLYNELNL
GRREEYDVLEKKRARDPEMGGKQQRRRNPQEGVYNALQKDKMAEAYSEIGTKGERRR
GKGHDGLYQGLSTATKDTYDALHMQTLA
```

SEQ ID 3: αVHH scFv, Amino Acid Sequence:
```
ANIVMTQTPASVSGAVGGTVTIKCQASQSISTYLSWYQQKPGQPPKLLIYQASELAYGV
SSRFKGSGSGTEFTLTISGVECADAATYYCQQGYSDINVDNFFGGGTEVVVKGGGGSGG
GGSGGGGSQSVEESGGRLVTPGTPLTLTCTVSGFSLNNYTVIWVRQAPGKGLEWIGIIFG
SGGTYYATWAEGRFTISRTSTTVDLKMTSPTTEDTATYFCARGYFGNTFWAMDPWGPG
TLVTVSS
```

SEQ ID 4: Murine αVHH CAR, Amino Acid Sequence:
```
MASPLTRFLSLNLLLLGESIILGSGEAANIVMTQTPASVSGAVGGTVTIKCQASQSISTYL
SWYQQKPGQPPKLLIYQASELAYGVSSRFKGSGSGTEFTLTISGVECADAATYYCQQGY
SDINVDNFFGGGTEVVVKGGGGSGGGGSGGGGSQSVEESGGRLVTPGTPLTLTCTVSGF
SLNNYTVIWVRQAPGKGLEWIGIIFGSGGTYYATWAEGRFTISRTSTTVDLKMTSPTTED
TATYFCARGYFGNTFWAMDPWGPGTLVTVSSTTTKPVLRTPSPVHPTGTSQPQRPEDCR
PRGSVKGTGLDFACDIYIWAPLAGICVALLLSLIITLICYHRSRNSRRNRLLQSDYMNMT
PRRPGLTRKPYQPYAPARDFAAYRPSRSAETAANLQDPNQLYNELNLGRREEYDVLEK
KRARDPEMGGKQQRRRNPQEGVYNALQKDKMAEAYSEIGTKGERRRGKGHDGLYQG
LSTATKDTYDALHMQTLA
```

SEQ ID 5: Human αSunTag CAR, Amino Acid Sequence
```
MALPVTALLLPLALLLHAARPGPDIVMTQSPSSLSASVGDRVTITCRSSTGAVTTSNYAS
WVQEKPGKLFKGLIGGTNNRAPGVPSRFSGSLIGDKATLTISSLQPEDFATYFCALWYSN
HWVFGQGTKVELKRGGGGSGGGGSGGGGSSGGGSEVKLLESGGGLVQPGGSLKLSCA
VSGFSLTDYGVNWVRQAPGRGLEWIGVIWGDGITDYNSALKDRFIISKDNGKNTVYLQ
MSKVRSDDTALYYCVTGLFDYWGQGTLVTVSSTTTPAPRPPTPAPTIASQPLSLRPEACR
PAAGGAVHTRGLDFACDIYIWAPLAGTCGVLLLSLVITLYCKRGRKKLLYIFKQPFMRP
VQTTQEEDGCSCRFPEEEEGGCELRVKFSRSADAPAYKQGQNQLYNELNLGRREEYDV
LDKRRGRDPEMGGKPRRKNPQEGLYNELQKDKMAEAYSEIGMKGERRRGKGHDGLY
QGLSTATKDTYDALHMQALPPR
```

SEQ ID 6: Human αFITC CAR, Amino Acid Sequence
```
MALPVTALLLPLALLLHAARPGVKLDETGGGLVQPGGAMKLSCVTSGFTFGHYWMN
WVRQSPEKGLEWVAQFRNKPYNYETYYSDSVKGRFTISRDDSKSSVYLQMNNLRVED
TGIYYCTGASYGMEYLGQGTSVTVSGGGGSGGGGSGGGGSGGGGSDVVMTQTPLSLP
VSLGDQASISCRSSQSLVHSNGNTYLRWYLQKPGQSPKVLIYKVSNRVSGVPDRESGSG
SGTDFTLKINRVEAEDLGVYFCSQSTHVPWTFGGGTKLEIKTTTPAPRPPTPAPTIASQPL
SLRPEACRPAAGGAVHTRGLDFACDIYIWAPLAGTCGVLLLSLVITLYCKRGRKKLLYIF
KQPFMRPVQTTQEEDGCSCRFPEEEEGGCELRVKFSRSADAPAYKQGQNQLYNELNLG
RREEYDVLDKRRGRDPEMGGKPRRKNPQEGLYNELQKDKMAEAYSEIGMKGERRRGK
GHDGLYQGLSTATKDTYDALHMQALPPR
```

SEQ ID 7: Human αVHH CAR, Amino Acid Sequence
```
MALPVTALLLPLALLLHAARPANIVMTQTPASVSGAVGGTVTIKCQASQSISTYLSWYQ
QKPGQPPKLLIYQASELAYGVSSRFKGSGSGTEFTLTISGVECADAATYYCQQGYSDINV
DNFFGGGTEVVVKGGGGSGGGGSGGGGSQSVEESGGRLVTPGTPLTLTCTVSGFSLNN
YTVIWVRQAPGKGLEWIGIIFGSGGTYYATWAEGRFTISRTSTTVDLKMTSPTTEDTATY
FCARGYFGNTFWAMDPWGPGTLVTVSSTTTPAPRPPTPAPTIASQPLSLRPEACRPAAG
```

-continued

F. Sequences

GAVHTRGLDFACDIYIWAPLAGTCGVLLLSLVITLYCKRGRKKLLYIFKQPFMRPVQTT
QEEDGCSCRFPEEEEGGCELRVKFSRSADAPAYKQGQNQLYNELNLGRREEYDVLDKR
RGRDPEMGGKPRRKNPQEGLYNELQKDKMAEAYSEIGMKGERRRGKGHDGLYQGLST
ATKDTYDALHMQALPPR

SEQ ID 8: DAF GPI 3x SunTag with 1x Linker, mRNA sequence
Gaaataagagagaaaagaagagtaagaagaaatataagagccaccatgaaatgggtcacatttatatctctgctcttccttttctcttcagcct
acagcgaggaactgctgagcaagaactaccacctggaaaacgaggtggcccggctgaaaaaaggctctggctctggcgaagaactgct
gtctaagaattatcacctcgagaatgaggtcgcccgcctcaagaaaggatctggaagtggcgaggaactcctctccaaaaactaccatctc
gagaacgaagtcgctaggcttaagaaaggaggcgggggcagccacgagaccacccccaacaaggggagcgggaccacgtccggca
caactagactgctttccggccatacatgctttacacttactgggctgctggggactcttgtaactatggggctcctcacatgataggctgccttc
tgcggggcttgccttctggccatgcccttcttctctcccttgcacctgtacctcttggtctttgaataaagcctgagtaggaaggc SEQ ID 9: DAF GPI 3x SunTag with 1x Linker, mRNA sequence
Gaaataagagagaaaagaagagtaagaagaaatataagagccaccatgaaatgggtcacatttatatctctgctcttccttttctcttcagcct
acagcgaggaactgctgagcaagaactaccacctggaaaacgaggtggcccggctgaaaaaggctctggctctggcgaagaactgct
gtctaagaattatcacctcgagaatgaggtcgcccgcctcaagaaaggatctggaagtggcgaggaactcctctccaaaaactaccatctc
gagaacgaagtcgctaggcttaagaaaggaggcgggggcagcggaggcgggggcagcggaggcgggggcagccacgagaccac
cccaacaaggggagcgggaccacgtccggcacaactagactgctttccggccatacatgctttacacttactgggctgctggggactctt
gtaactatggggctcctcacatgataggctgccttctgcggggcttgccttctggccatgcccttcttctctcccttgcacctgtacctcttggtc
tttgaataaagcctgagtaggaaggc SEQ ID 10: DAF GPI 3x SunTag with RSV-F VHH, mRNA sequence
gaaataagagagaaaagaagagtaagaagaaatataagagccaccatgaaatgggtcacatttatatctctgctcttccttttctcttcagcct
acagcgaggaactgctgagcaagaactaccacctggaaaacgaggtggcccggctgaaaaaggctctggctctggcgaagaactgct
gtctaagaattatcacctcgagaatgaggtcgcccgcctcaagaaaggatctggaagtggcgaggaactcctctccaaaaactaccatctc
gagaacgaagtcgctaggcttaagaaaggaggcgggggcagccaggtacagttgcaggagtccggaggtggtctggtacaaccaggt
ggatccctcagattgtcttgtgcagctagtggctttacgctcgactactattatatcgggtggtttcggcaagcaccgggtaaagagagggag
gctgttagctgtatcagcggctcttcagggtccacgtattaccctgacagtgttaaagggagatttaccatatcccgcgataacgcaaagaac
actgtgtacttgcagatgaatagcctgaagcccgaggacacagccgtttactactgtgccacgattcgctcctcttcatggggaggatgcgtt
cattacgggatggattactggggcaaaggcactcaggtgacggttagctctggaggcgggggcagccacgagaccacccccaacaagg
ggagcgggaccacgtccggcacaactagactgctttccggccatacatgctttacacttactgggctgctggggactcttgtaactatgggg
ctcctcacatgataggctgccttctgcggggcttgccttctggccatgcccttcttctctcccttgcacctgtacctcttggtctttgaataaagcc
tgagtaggaaggc SEQ ID 11: DAF GPI VHH, mRNA sequence
gaaataagagagaaaagaagagtaagaagaaatataagagccaccatgaaatgggtcacatttatatctctgctcttccttttctcttcagcct
acagccaggtacagttgcaggagtccggaggtggtctggtacaaccaggtggatccctcagattgtcttgtgcagctagtggctttacgctc
gactactattatatcgggtggtttcggcaagcaccgggtaaagagagggaggctgttagctgtatcagcggctcttcagggtccacgtatta
ccctgacagtgttaaagggagatttaccatatcccgcgataacgcaaagaacactgtgtacttgcagatgaatagcctgaagcccgaggac
acagccgtttactactgtgccacgattcgctcctcttcatggggaggatgcgttcattacgggatggattactggggcaaaggcactcaggt
gacggttagctctggaggcgggggcagccacgagaccacccccaacaaggggagcgggaccacgtccggcacaactagactgctttc
cggccatacatgctttacacttactgggctgctggggactcttgtaactatggggctcctcacatgataggctgccttctgcggggcttgcctt
ctggccatgcccttcttctctcccttgcacctgtacctcttggtctttgaataaagcctgagtaggaaggc

What is claimed is:

1. A synthetic antigen-chimeric antigen receptor system comprising a synthetic antigen and a chimeric antigen receptor (CAR) that targets said antigen;

wherein the synthetic antigen is encoded by SEQ ID NO: 8, SEQ ID NO: 9, SEQ ID NO: 10, or SEQ ID NO: 11.

2. The synthetic antigen-chimeric antigen receptor system of claim 1, wherein the synthetic antigen comprises small molecules or genetically encoded antigens.

3. The synthetic antigen-chimeric antigen receptor system of claim 2, wherein the synthetic antigen comprises a small molecule comprising Fluorescein isothiocyanate (FITC), 3-Amino-3-(2-nitro-phenyl)propionic Acid (ANP) or indocyanine green (ICG).

4. The synthetic antigen-chimeric antigen receptor system of claim 1, wherein the synthetic antigen is encoded by a plasmid, viral vector, minicircle DNA, or mRNA.

5. The synthetic antigen-chimeric antigen receptor system of claim 1, wherein the synthetic antigen is delivered by a fusogenic liposome.

6. The synthetic antigen-chimeric antigen receptor system of claim 1, wherein the chimeric antigen receptor comprises a single chain (sc) FV (scFv);

wherein the scFv comprises:

a) HCDR1-3 and LCDR1-3 of either amino acid SEQ ID NO: 1 or 5 according to the Kabat, IGMT, Chothia, or AbM scheme, and binds general control protein GCN4 (GCN4);

b) HCDR1-3 and LCDR1-3 of either amino acid SEQ ID NO: 3 or 7 according to the Kabat, IGMT, Chothia, or AbM scheme, and binds a VHH anti-respiratory syncytial virus (RSV) F glycoprotein (RSV-F) single domain antibody; or c) HCDR1-3 and LCDR1-3 of either amino acid SEQ ID NO: 2 or 6 according to the Kabat, IGMT, Chothia, or AbM scheme, and binds fluorescein isothiocyanate (FITC).

7. The synthetic antigen-chimeric antigen receptor system of claim 6, wherein the chimeric antigen receptor comprises the amino acid sequence as set forth in SEQ ID NO: 1, SEQ ID NO: 2, SEQ ID NO: 3, SEQ ID NO: 4, SEQ ID NO: 5, SEQ ID NO: 6, or SEQ ID NO: 7.

8. The synthetic antigen-chimeric antigen receptor system of claim 1, wherein the chimeric antigen receptor is encoded on a plasmid, viral vector, minicircle DNA, or mRNA.

9. An immune cell comprising the chimeric antigen receptor of claim 6.

10. The immune cell of claim 9, wherein the immune cell has been transfected or transduced with the chimeric antigen receptor.

11. The immune cell of claim 9, wherein the immune cell comprises a CAR T cell, CAR Natural Killer Cell (CAR NK cell), CAR NK T cell, or CAR Macrophage (CARMA).

12. A method of treating a cancer in a subject comprising:

a) transfecting or transducing a cancerous cell, tumor associated fibroblast, myeloid derived suppressor cell (MDSC), regulatory T cells (Tregs), or extracellular matrix (ECM) with a synthetic antigen, wherein the synthetic antigen is encoded by a nucleic acid selected from SEQ ID NO: 8, 9, 10, or 11;

b) administering to the subject the immune cell of claim 9;

wherein the immune cell specifically targets and binds the synthetic antigen thereby killing the cancer cell, tumor associated fibroblast, myeloid-derived suppressor cell (MDSC), regulatory T cells (Tregs), or extracellular matrix (ECM).

13. The method of treating a cancer of claim 12, wherein the synthetic antigen is expressed on the membrane of the transfected cancerous cell.

14. The method treating a cancer of claim 12, wherein the synthetic antigen is transfected or transduced into the cancerous cell, tumor associated fibroblast, myeloid-derived suppressor cell (MDSC), regulatory T cells (Tregs), or extracellular matrix (ECM) via plasmid, liposome, viral vector, bacteria, minicircle DNA, or mRNA.

15. The method of treating a cancer of claim 12, wherein the immune cell comprises a CAR T cell, CAR Natural Killer Cell (CAR NK cell), CAR NK T cell, or CAR Macrophage (CARMA).

16. The method of treating a cancer of claim 12, further comprising obtaining an immune cell.

17. The method of treating a cancer of claim 16, wherein the immune cell is obtained from an autologous or allogeneic donor.

18. The method of treating a cancer of claim 16, further comprising transfecting or transducing the immune cell with the chimeric antigen receptor.

19. The method of treating a cancer of claim 12, wherein the immune cell is administered to the subject concurrently with the transfection or transduction of the cancerous cell, tumor associated fibroblast, myeloid-derived suppressor cell (MDSC), regulatory T cells (Tregs), or extracellular matrix (ECM).

20. The method of treating a cancer of claim 12, wherein the immune cell is administered to the subject before the transfection or transduction of the cancerous cell, tumor associated fibroblast, myeloid-derived suppressor cell (MDSC), regulatory T cells (Tregs), or extracellular matrix (ECM).

21. The method of treating a cancer of claim 12, wherein the immune cell is administered to the subject after the transfection or transduction of the cancerous cell, tumor associated fibroblast, myeloid-derived suppressor cell (MDSC), regulatory T cells (Tregs), or extracellular matrix (ECM).

22. A method of treating metastasis in a subject comprising a) transfecting or transducing a primary cancerous cell, tumor associated fibroblast, myeloid-derived suppressor cell (MDSC), regulatory T cells (Tregs), or extracellular matrix (ECM) with a synthetic antigen, wherein the synthetic antigen is encoded by a nucleic acid selected from SEQ ID NO: 8, 9, 10, or 11;

b) administering to the subject the immune cell of claim 9;

wherein the immune cell specifically targets and binds the synthetic antigen thereby killing the cancer cell, tumor associated fibroblast, myeloid-derived suppressor cell (MDSC), regulatory T cells (Tregs), or extracellular matrix (ECM); wherein treatment of the primary tumor results in abscopal treatment of the metastatic tumor.

* * * * *

SEQUENCE LISTING

<160> NUMBER OF SEQ ID NOS: 17

<210> SEQ ID NO 1
<211> LENGTH: 493
<212> TYPE: PRT
<213> ORGANISM: Artificial Sequence
<220> FEATURE:
<223> OTHER INFORMATION: Synthetic construct

<400> SEQUENCE: 1

```
Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Gly Pro Asp Ile Val
            20                  25                  30

Met Thr Gln Ser Pro Ser Ser Leu Ser Ala Ser Val Gly Asp Arg Val
        35                  40                  45

Thr Ile Thr Cys Arg Ser Ser Thr Gly Ala Val Thr Thr Ser Asn Tyr
    50                  55                  60

Ala Ser Trp Val Gln Glu Lys Pro Gly Lys Leu Phe Lys Gly Leu Ile
65                  70                  75                  80
```

```
Gly Gly Thr Asn Asn Arg Ala Pro Gly Val Pro Ser Arg Phe Ser Gly
                85                  90                  95

Ser Leu Ile Gly Asp Lys Ala Thr Leu Thr Ile Ser Ser Leu Gln Pro
            100                 105                 110

Glu Asp Phe Ala Thr Tyr Phe Cys Ala Leu Trp Tyr Ser Asn His Trp
        115                 120                 125

Val Phe Gly Gln Gly Thr Lys Val Glu Leu Lys Arg Gly Gly Gly Gly
    130                 135                 140

Ser Gly Gly Gly Gly Ser Gly Gly Gly Gly Ser Ser Gly Gly Gly Ser
145                 150                 155                 160

Glu Val Lys Leu Leu Glu Ser Gly Gly Gly Leu Val Gln Pro Gly Gly
                165                 170                 175

Ser Leu Lys Leu Ser Cys Ala Val Ser Gly Phe Ser Leu Thr Asp Tyr
            180                 185                 190

Gly Val Asn Trp Val Arg Gln Ala Pro Gly Arg Gly Leu Glu Trp Ile
        195                 200                 205

Gly Val Ile Trp Gly Asp Gly Ile Thr Asp Tyr Asn Ser Ala Leu Lys
    210                 215                 220

Asp Arg Phe Ile Ile Ser Lys Asp Asn Gly Lys Asn Thr Val Tyr Leu
225                 230                 235                 240

Gln Met Ser Lys Val Arg Ser Asp Asp Thr Ala Leu Tyr Tyr Cys Val
                245                 250                 255

Thr Gly Leu Phe Asp Tyr Trp Gly Gln Gly Thr Leu Val Thr Val Ser
            260                 265                 270

Ser Thr Thr Thr Lys Pro Val Leu Arg Thr Pro Ser Pro Val His Pro
        275                 280                 285

Thr Gly Thr Ser Gln Pro Gln Arg Pro Glu Asp Cys Arg Pro Arg Gly
    290                 295                 300

Ser Val Lys Gly Thr Gly Leu Asp Phe Ala Cys Asp Ile Tyr Ile Trp
305                 310                 315                 320

Ala Pro Leu Ala Gly Ile Cys Val Ala Leu Leu Leu Ser Leu Ile Ile
                325                 330                 335

Thr Leu Ile Cys Tyr His Arg Ser Arg Asn Ser Arg Arg Asn Arg Leu
            340                 345                 350

Leu Gln Ser Asp Tyr Met Asn Met Thr Pro Arg Arg Pro Gly Leu Thr
        355                 360                 365

Arg Lys Pro Tyr Gln Pro Tyr Ala Pro Ala Arg Asp Phe Ala Ala Tyr
    370                 375                 380

Arg Pro Ser Arg Ser Ala Glu Thr Ala Ala Asn Leu Gln Asp Pro Asn
385                 390                 395                 400

Gln Leu Tyr Asn Glu Leu Asn Leu Gly Arg Arg Glu Glu Tyr Asp Val
                405                 410                 415

Leu Glu Lys Lys Arg Ala Arg Asp Pro Glu Met Gly Gly Lys Gln Gln
            420                 425                 430

Arg Arg Arg Asn Pro Gln Glu Gly Val Tyr Asn Ala Leu Gln Lys Asp
        435                 440                 445

Lys Met Ala Glu Ala Tyr Ser Glu Ile Gly Thr Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Thr Leu Ala
                485                 490
```

<210> SEQ ID NO 2
<211> LENGTH: 496
<212> TYPE: PRT
<213> ORGANISM: Artificial Sequence
<220> FEATURE:
<223> OTHER INFORMATION: Synthetic construct

<400> SEQUENCE: 2

Met Ala Ser Pro Leu Thr Arg Phe Leu Ser Leu Asn Leu Leu Leu Leu
1 5 10 15

Gly Glu Ser Ile Ile Leu Gly Ser Gly Glu Ala Gly Val Lys Leu Asp
20 25 30

Glu Thr Gly Gly Gly Leu Val Gln Pro Gly Gly Ala Met Lys Leu Ser
35 40 45

Cys Val Thr Ser Gly Phe Thr Phe Gly His Tyr Trp Met Asn Trp Val
50 55 60

Arg Gln Ser Pro Glu Lys Gly Leu Glu Trp Val Ala Gln Phe Arg Asn
65 70 75 80

Lys Pro Tyr Asn Tyr Glu Thr Tyr Tyr Ser Asp Ser Val Lys Gly Arg
85 90 95

Phe Thr Ile Ser Arg Asp Asp Ser Lys Ser Ser Val Tyr Leu Gln Met
100 105 110

Asn Asn Leu Arg Val Glu Asp Thr Gly Ile Tyr Tyr Cys Thr Gly Ala
115 120 125

Ser Tyr Gly Met Glu Tyr Leu Gly Gln Gly Thr Ser Val Thr Val Ser
130 135 140

Gly Gly Gly Gly Ser Gly Gly Gly Gly Ser Gly Gly Gly Gly Ser Gly
145 150 155 160

Gly Gly Gly Ser Asp Val Val Met Thr Gln Thr Pro Leu Ser Leu Pro
165 170 175

Val Ser Leu Gly Asp Gln Ala Ser Ile Ser Cys Arg Ser Ser Gln Ser
180 185 190

Leu Val His Ser Asn Gly Asn Thr Tyr Leu Arg Trp Tyr Leu Gln Lys
195 200 205

Pro Gly Gln Ser Pro Lys Val Leu Ile Tyr Lys Val Ser Asn Arg Val
210 215 220

Ser Gly Val Pro Asp Arg Phe Ser Gly Ser Gly Ser Gly Thr Asp Phe
225 230 235 240

Thr Leu Lys Ile Asn Arg Val Glu Ala Glu Asp Leu Gly Val Tyr Phe
245 250 255

Cys Ser Gln Ser Thr His Val Pro Trp Thr Phe Gly Gly Gly Thr Lys
260 265 270

Leu Glu Ile Lys Thr Thr Thr Lys Pro Val Leu Arg Thr Pro Ser Pro
275 280 285

Val His Pro Thr Gly Thr Ser Gln Pro Gln Arg Pro Glu Asp Cys Arg
290 295 300

Pro Arg Gly Ser Val Lys Gly Thr Gly Leu Asp Phe Ala Cys Asp Ile
305 310 315 320

Tyr Ile Trp Ala Pro Leu Ala Gly Ile Cys Val Ala Leu Leu Leu Ser
325 330 335

Leu Ile Ile Thr Leu Ile Cys Tyr His Arg Ser Arg Asn Ser Arg Arg
340 345 350

Asn Arg Leu Leu Gln Ser Asp Tyr Met Asn Met Thr Pro Arg Arg Pro
355 360 365

Gly Leu Thr Arg Lys Pro Tyr Gln Pro Tyr Ala Pro Ala Arg Asp Phe

```
    370                 375                 380

Ala Ala Tyr Arg Pro Ser Arg Ser Ala Glu Thr Ala Ala Asn Leu Gln
385                 390                 395                 400

Asp Pro Asn Gln Leu Tyr Asn Glu Leu Asn Leu Gly Arg Arg Glu Glu
                405                 410                 415

Tyr Asp Val Leu Glu Lys Lys Arg Ala Arg Asp Pro Glu Met Gly Gly
            420                 425                 430

Lys Gln Gln Arg Arg Arg Asn Pro Gln Glu Gly Val Tyr Asn Ala Leu
        435                 440                 445

Gln Lys Asp Lys Met Ala Glu Ala Tyr Ser Glu Ile Gly Thr Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Thr Leu Ala
                485                 490                 495


<210> SEQ ID NO 3
<211> LENGTH: 243
<212> TYPE: PRT
<213> ORGANISM: Artificial Sequence
<220> FEATURE:
<223> OTHER INFORMATION: Synthetic construct

<400> SEQUENCE: 3

Ala Asn Ile Val Met Thr Gln Thr Pro Ala Ser Val Ser Gly Ala Val
1               5                   10                  15

Gly Gly Thr Val Thr Ile Lys Cys Gln Ala Ser Gln Ser Ile Ser Thr
            20                  25                  30

Tyr Leu Ser Trp Tyr Gln Gln Lys Pro Gly Gln Pro Pro Lys Leu Leu
        35                  40                  45

Ile Tyr Gln Ala Ser Glu Leu Ala Tyr Gly Val Ser Ser Arg Phe Lys
    50                  55                  60

Gly Ser Gly Ser Gly Thr Glu Phe Thr Leu Thr Ile Ser Gly Val Glu
65                  70                  75                  80

Cys Ala Asp Ala Ala Thr Tyr Tyr Cys Gln Gln Gly Tyr Ser Asp Ile
                85                  90                  95

Asn Val Asp Asn Phe Phe Gly Gly Gly Thr Glu Val Val Val Lys Gly
            100                 105                 110

Gly Gly Gly Ser Gly Gly Gly Gly Ser Gly Gly Gly Gly Ser Gln Ser
        115                 120                 125

Val Glu Glu Ser Gly Gly Arg Leu Val Thr Pro Gly Thr Pro Leu Thr
    130                 135                 140

Leu Thr Cys Thr Val Ser Gly Phe Ser Leu Asn Asn Tyr Thr Val Ile
145                 150                 155                 160

Trp Val Arg Gln Ala Pro Gly Lys Gly Leu Glu Trp Ile Gly Ile Ile
                165                 170                 175

Phe Gly Ser Gly Gly Thr Tyr Tyr Ala Thr Trp Ala Glu Gly Arg Phe
            180                 185                 190

Thr Ile Ser Arg Thr Ser Thr Thr Val Asp Leu Lys Met Thr Ser Pro
        195                 200                 205

Thr Thr Glu Asp Thr Ala Thr Tyr Phe Cys Ala Arg Gly Tyr Phe Gly
    210                 215                 220

Asn Thr Phe Trp Ala Met Asp Pro Trp Gly Pro Gly Thr Leu Val Thr
225                 230                 235                 240

Val Ser Ser
```

<210> SEQ ID NO 4
<211> LENGTH: 490
<212> TYPE: PRT
<213> ORGANISM: Artificial Sequence
<220> FEATURE:
<223> OTHER INFORMATION: Synthetic construct

<400> SEQUENCE: 4

```
Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Ala Asn Ile Val Met
            20                  25                  30

Thr Gln Thr Pro Ala Ser Val Ser Gly Ala Val Gly Gly Thr Val Thr
        35                  40                  45

Ile Lys Cys Gln Ala Ser Gln Ser Ile Ser Thr Tyr Leu Ser Trp Tyr
    50                  55                  60

Gln Gln Lys Pro Gly Gln Pro Pro Lys Leu Leu Ile Tyr Gln Ala Ser
65                  70                  75                  80

Glu Leu Ala Tyr Gly Val Ser Ser Arg Phe Lys Gly Ser Gly Ser Gly
                85                  90                  95

Thr Glu Phe Thr Leu Thr Ile Ser Gly Val Glu Cys Ala Asp Ala Ala
            100                 105                 110

Thr Tyr Tyr Cys Gln Gln Gly Tyr Ser Asp Ile Asn Val Asp Asn Phe
        115                 120                 125

Phe Gly Gly Gly Thr Glu Val Val Val Lys Gly Gly Gly Gly Ser Gly
    130                 135                 140

Gly Gly Gly Ser Gly Gly Gly Gly Ser Gln Ser Val Glu Glu Ser Gly
145                 150                 155                 160

Gly Arg Leu Val Thr Pro Gly Thr Pro Leu Thr Leu Thr Cys Thr Val
                165                 170                 175

Ser Gly Phe Ser Leu Asn Asn Tyr Thr Val Ile Trp Val Arg Gln Ala
            180                 185                 190

Pro Gly Lys Gly Leu Glu Trp Ile Gly Ile Ile Phe Gly Ser Gly Gly
        195                 200                 205

Thr Tyr Tyr Ala Thr Trp Ala Glu Gly Arg Phe Thr Ile Ser Arg Thr
    210                 215                 220

Ser Thr Thr Val Asp Leu Lys Met Thr Ser Pro Thr Thr Glu Asp Thr
225                 230                 235                 240

Ala Thr Tyr Phe Cys Ala Arg Gly Tyr Phe Gly Asn Thr Phe Trp Ala
                245                 250                 255

Met Asp Pro Trp Gly Pro Gly Thr Leu Val Thr Val Ser Ser Thr Thr
            260                 265                 270

Thr Lys Pro Val Leu Arg Thr Pro Ser Pro Val His Pro Thr Gly Thr
        275                 280                 285

Ser Gln Pro Gln Arg Pro Glu Asp Cys Arg Pro Arg Gly Ser Val Lys
    290                 295                 300

Gly Thr Gly Leu Asp Phe Ala Cys Asp Ile Tyr Ile Trp Ala Pro Leu
305                 310                 315                 320

Ala Gly Ile Cys Val Ala Leu Leu Leu Ser Leu Ile Ile Thr Leu Ile
                325                 330                 335

Cys Tyr His Arg Ser Arg Asn Ser Arg Arg Asn Arg Leu Leu Gln Ser
            340                 345                 350

Asp Tyr Met Asn Met Thr Pro Arg Arg Pro Gly Leu Thr Arg Lys Pro
        355                 360                 365
```

```
Tyr Gln Pro Tyr Ala Pro Ala Arg Asp Phe Ala Ala Tyr Arg Pro Ser
    370                 375                 380

Arg Ser Ala Glu Thr Ala Ala Asn Leu Gln Asp Pro Asn Gln Leu Tyr
385                 390                 395                 400

Asn Glu Leu Asn Leu Gly Arg Arg Glu Glu Tyr Asp Val Leu Glu Lys
                405                 410                 415

Lys Arg Ala Arg Asp Pro Glu Met Gly Gly Lys Gln Gln Arg Arg Arg
            420                 425                 430

Asn Pro Gln Glu Gly Val Tyr Asn Ala Leu Gln Lys Asp Lys Met Ala
        435                 440                 445

Glu Ala Tyr Ser Glu Ile Gly Thr Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Thr Leu Ala
                485                 490


<210> SEQ ID NO 5
<211> LENGTH: 490
<212> TYPE: PRT
<213> ORGANISM: Artificial Sequence
<220> FEATURE:
<223> OTHER INFORMATION: Synthetic construct

<400> SEQUENCE: 5

Met Ala Leu Pro Val Thr Ala Leu Leu Leu Pro Leu Ala Leu Leu Leu
1               5                   10                  15

His Ala Ala Arg Pro Gly Pro Asp Ile Val Met Thr Gln Ser Pro Ser
            20                  25                  30

Ser Leu Ser Ala Ser Val Gly Asp Arg Val Thr Ile Thr Cys Arg Ser
        35                  40                  45

Ser Thr Gly Ala Val Thr Thr Ser Asn Tyr Ala Ser Trp Val Gln Glu
    50                  55                  60

Lys Pro Gly Lys Leu Phe Lys Gly Leu Ile Gly Gly Thr Asn Asn Arg
65                  70                  75                  80

Ala Pro Gly Val Pro Ser Arg Phe Ser Gly Ser Leu Ile Gly Asp Lys
                85                  90                  95

Ala Thr Leu Thr Ile Ser Ser Leu Gln Pro Glu Asp Phe Ala Thr Tyr
            100                 105                 110

Phe Cys Ala Leu Trp Tyr Ser Asn His Trp Val Phe Gly Gln Gly Thr
        115                 120                 125

Lys Val Glu Leu Lys Arg Gly Gly Gly Gly Ser Gly Gly Gly Gly Ser
    130                 135                 140

Gly Gly Gly Gly Ser Ser Gly Gly Gly Ser Glu Val Lys Leu Leu Glu
145                 150                 155                 160

Ser Gly Gly Gly Leu Val Gln Pro Gly Gly Ser Leu Lys Leu Ser Cys
                165                 170                 175

Ala Val Ser Gly Phe Ser Leu Thr Asp Tyr Gly Val Asn Trp Val Arg
            180                 185                 190

Gln Ala Pro Gly Arg Gly Leu Glu Trp Ile Gly Val Ile Trp Gly Asp
        195                 200                 205

Gly Ile Thr Asp Tyr Asn Ser Ala Leu Lys Asp Arg Phe Ile Ile Ser
    210                 215                 220

Lys Asp Asn Gly Lys Asn Thr Val Tyr Leu Gln Met Ser Lys Val Arg
225                 230                 235                 240
```

```
Ser Asp Asp Thr Ala Leu Tyr Tyr Cys Val Thr Gly Leu Phe Asp Tyr
                245                 250                 255

Trp Gly Gln Gly Thr Leu Val Thr Val Ser Ser Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 6
<211> LENGTH: 493
<212> TYPE: PRT
<213> ORGANISM: Artificial Sequence
<220> FEATURE:
<223> OTHER INFORMATION: Synthetic construct

<400> SEQUENCE: 6

```
Met Ala Leu Pro Val Thr Ala Leu Leu Leu Pro Leu Ala Leu Leu Leu
1               5                   10                  15

His Ala Ala Arg Pro Gly Val Lys Leu Asp Glu Thr Gly Gly Gly Leu
            20                  25                  30

Val Gln Pro Gly Gly Ala Met Lys Leu Ser Cys Val Thr Ser Gly Phe
        35                  40                  45

Thr Phe Gly His Tyr Trp Met Asn Trp Val Arg Gln Ser Pro Glu Lys
    50                  55                  60

Gly Leu Glu Trp Val Ala Gln Phe Arg Asn Lys Pro Tyr Asn Tyr Glu
65                  70                  75                  80

Thr Tyr Tyr Ser Asp Ser Val Lys Gly Arg Phe Thr Ile Ser Arg Asp
                85                  90                  95

Asp Ser Lys Ser Ser Val Tyr Leu Gln Met Asn Asn Leu Arg Val Glu
            100                 105                 110
```

```
Asp Thr Gly Ile Tyr Tyr Cys Thr Gly Ala Ser Tyr Gly Met Glu Tyr
        115                 120                 125

Leu Gly Gln Gly Thr Ser Val Thr Val Ser Gly Gly Gly Gly Ser Gly
    130                 135                 140

Gly Gly Gly Ser Gly Gly Gly Gly Ser Gly Gly Gly Gly Ser Asp Val
145                 150                 155                 160

Val Met Thr Gln Thr Pro Leu Ser Leu Pro Val Ser Leu Gly Asp Gln
                165                 170                 175

Ala Ser Ile Ser Cys Arg Ser Ser Gln Ser Leu Val His Ser Asn Gly
            180                 185                 190

Asn Thr Tyr Leu Arg Trp Tyr Leu Gln Lys Pro Gly Gln Ser Pro Lys
        195                 200                 205

Val Leu Ile Tyr Lys Val Ser Asn Arg Val Ser Gly Val Pro Asp Arg
    210                 215                 220

Phe Ser Gly Ser Gly Ser Gly Thr Asp Phe Thr Leu Lys Ile Asn Arg
225                 230                 235                 240

Val Glu Ala Glu Asp Leu Gly Val Tyr Phe Cys Ser Gln Ser Thr His
                245                 250                 255

Val Pro Trp Thr Phe Gly Gly Gly Thr Lys Leu Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 7
<211> LENGTH: 487
<212> TYPE: PRT
<213> ORGANISM: Artificial Sequence
<220> FEATURE:

<223> OTHER INFORMATION: Synthetic construct

<400> SEQUENCE: 7

```
Met Ala Leu Pro Val Thr Ala Leu Leu Leu Pro Leu Ala Leu Leu Leu
1               5                   10                  15

His Ala Ala Arg Pro Ala Asn Ile Val Met Thr Gln Thr Pro Ala Ser
            20                  25                  30

Val Ser Gly Ala Val Gly Gly Thr Val Thr Ile Lys Cys Gln Ala Ser
        35                  40                  45

Gln Ser Ile Ser Thr Tyr Leu Ser Trp Tyr Gln Gln Lys Pro Gly Gln
    50                  55                  60

Pro Pro Lys Leu Leu Ile Tyr Gln Ala Ser Glu Leu Ala Tyr Gly Val
65                  70                  75                  80

Ser Ser Arg Phe Lys Gly Ser Gly Ser Gly Thr Glu Phe Thr Leu Thr
                85                  90                  95

Ile Ser Gly Val Glu Cys Ala Asp Ala Ala Thr Tyr Tyr Cys Gln Gln
            100                 105                 110

Gly Tyr Ser Asp Ile Asn Val Asp Asn Phe Phe Gly Gly Gly Thr Glu
        115                 120                 125

Val Val Val Lys Gly Gly Gly Gly Ser Gly Gly Gly Gly Ser Gly Gly
    130                 135                 140

Gly Gly Ser Gln Ser Val Glu Glu Ser Gly Gly Arg Leu Val Thr Pro
145                 150                 155                 160

Gly Thr Pro Leu Thr Leu Thr Cys Thr Val Ser Gly Phe Ser Leu Asn
                165                 170                 175

Asn Tyr Thr Val Ile Trp Val Arg Gln Ala Pro Gly Lys Gly Leu Glu
            180                 185                 190

Trp Ile Gly Ile Ile Phe Gly Ser Gly Gly Thr Tyr Tyr Ala Thr Trp
        195                 200                 205

Ala Glu Gly Arg Phe Thr Ile Ser Arg Thr Ser Thr Thr Val Asp Leu
    210                 215                 220

Lys Met Thr Ser Pro Thr Thr Glu Asp Thr Ala Thr Tyr Phe Cys Ala
225                 230                 235                 240

Arg Gly Tyr Phe Gly Asn Thr Phe Trp Ala Met Asp Pro Trp Gly Pro
                245                 250                 255

Gly Thr Leu Val Thr Val Ser Ser Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Lys Gln Gly Gln Asn Gln Leu Tyr Asn Glu Leu Asn
385                 390                 395                 400
```

```
Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485


<210> SEQ ID NO 8
<211> LENGTH: 539
<212> TYPE: DNA
<213> ORGANISM: Artificial Sequence
<220> FEATURE:
<223> OTHER INFORMATION: Synthetic construct

<400> SEQUENCE: 8

gaaataagag agaaaagaag agtaagaaga aatataagag ccaccatgaa atgggtcaca      60

tttatatctc tgctcttcct tttctcttca gcctacagcg aggaactgct gagcaagaac     120

taccacctgg aaaacgaggt ggcccggctg aaaaaaggct ctggctctgg cgaagaactg     180

ctgtctaaga attatcacct cgagaatgag gtcgcccgcc tcaagaaagg atctggaagt     240

ggcgaggaac tcctctccaa aaactaccat ctcgagaacg aagtcgctag gcttaagaaa     300

ggaggcgggg gcagccacga gaccaccccc aacaagggga gcgggaccac gtccggcaca     360

actagactgc tttccggcca tacatgcttt acacttactg ggctgctggg gactcttgta     420

actatggggc tcctcacatg ataggctgcc ttctgcgggg cttgccttct ggccatgccc     480

ttcttctctc ccttgcacct gtacctcttg gtctttgaat aaagcctgag taggaaggc      539


<210> SEQ ID NO 9
<211> LENGTH: 569
<212> TYPE: DNA
<213> ORGANISM: Artificial Sequence
<220> FEATURE:
<223> OTHER INFORMATION: Synthetic construct

<400> SEQUENCE: 9

gaaataagag agaaaagaag agtaagaaga aatataagag ccaccatgaa atgggtcaca      60

tttatatctc tgctcttcct tttctcttca gcctacagcg aggaactgct gagcaagaac     120

taccacctgg aaaacgaggt ggcccggctg aaaaaaggct ctggctctgg cgaagaactg     180

ctgtctaaga attatcacct cgagaatgag gtcgcccgcc tcaagaaagg atctggaagt     240

ggcgaggaac tcctctccaa aaactaccat ctcgagaacg aagtcgctag gcttaagaaa     300

ggaggcgggg gcagcggagg cgggggcagc ggaggcgggg gcagccacga gaccaccccc     360

aacaagggga gcgggaccac gtccggcaca actagactgc tttccggcca tacatgcttt     420

acacttactg ggctgctggg gactcttgta actatggggc tcctcacatg ataggctgcc     480

ttctgcgggg cttgccttct ggccatgccc ttcttctctc ccttgcacct gtacctcttg     540

gtctttgaat aaagcctgag taggaaggc                                      569


<210> SEQ ID NO 10
<211> LENGTH: 929
```

```
<212> TYPE: DNA
<213> ORGANISM: Artificial Sequence
<220> FEATURE:
<223> OTHER INFORMATION: Synthetic construct

<400> SEQUENCE: 10

gaaataagag agaaaagaag agtaagaaga aatataagag ccaccatgaa atgggtcaca     60

tttatatctc tgctcttcct tttctcttca gcctacagcg aggaactgct gagcaagaac    120

taccacctgg aaaacgaggt ggcccggctg aaaaaaggct ctggctctgg cgaagaactg    180

ctgtctaaga attatcacct cgagaatgag gtcgcccgcc tcaagaaagg atctggaagt    240

ggcgaggaac tcctctccaa aaactaccat ctcgagaacg aagtcgctag gcttaagaaa    300

ggaggcgggg gcagccaggt acagttgcag gagtccggag gtggtctggt acaaccaggt    360

ggatccctca gattgtcttg tgcagctagt ggctttacgc tcgactacta ttatatcggg    420

tggtttcggc aagcaccggg taaagagagg gaggctgtta gctgtatcag cggctcttca    480

gggtccacgt attaccctga cagtgttaaa gggagattta ccatatcccg cgataacgca    540

aagaacactg tgtacttgca gatgaatagc ctgaagcccg aggacacagc cgtttactac    600

tgtgccacga ttcgctcctc ttcatgggga ggatgcgttc attacgggat ggattactgg    660

ggcaaaggca ctcaggtgac ggttagctct ggaggcgggg gcagccacga gaccaccccc    720

aacaagggga gcgggaccac gtccggcaca actagactgc tttccggcca tacatgcttt    780

acacttactg ggctgctggg gactcttgta actatggggc tcctcacatg ataggctgcc    840

ttctgcgggg cttgccttct ggccatgccc ttcttctctc ccttgcacct gtacctcttg    900

gtctttgaat aaagcctgag taggaaggc                                      929


<210> SEQ ID NO 11
<211> LENGTH: 713
<212> TYPE: DNA
<213> ORGANISM: Artificial Sequence
<220> FEATURE:
<223> OTHER INFORMATION: Synthetic construct

<400> SEQUENCE: 11

gaaataagag agaaaagaag agtaagaaga aatataagag ccaccatgaa atgggtcaca     60

tttatatctc tgctcttcct tttctcttca gcctacagcc aggtacagtt gcaggagtcc    120

ggaggtggtc tggtacaacc aggtggatcc ctcagattgt cttgtgcagc tagtggcttt    180

acgctcgact actattatat cgggtggttt cggcaagcac cgggtaaaga gagggaggct    240

gttagctgta tcagcggctc ttcagggtcc acgtattacc ctgacagtgt taaagggaga    300

tttaccatat cccgcgataa cgcaaagaac actgtgtact tgcagatgaa tagcctgaag    360

cccgaggaca cagccgttta ctactgtgcc acgattcgct cctcttcatg gggaggatgc    420

gttcattacg ggatggatta ctggggcaaa ggcactcagg tgacggttag ctctggaggc    480

gggggcagcc acgagaccac ccccaacaag gggagcggga ccacgtccgg cacaactaga    540

ctgctttccg gccatacatg ctttacactt actgggctgc tggggactct tgtaactatg    600

gggctcctca catgataggc tgccttctgc ggggcttgcc ttctggccat gcccttcttc    660

tctcccttgc acctgtacct cttggtcttt gaataaagcc tgagtaggaa ggc           713


<210> SEQ ID NO 12
<211> LENGTH: 19
<212> TYPE: PRT
<213> ORGANISM: Artificial Sequence
<220> FEATURE:
```

-continued

<223> OTHER INFORMATION: Synthetic construct

<400> SEQUENCE: 12

Glu Glu Leu Leu Ser Lys Asn Tyr His Leu Glu Asn Glu Val Ala Arg
1 5 10 15

Leu Lys Lys

<210> SEQ ID NO 13
<211> LENGTH: 8
<212> TYPE: PRT
<213> ORGANISM: Gallus gallus

<400> SEQUENCE: 13

Ser Ile Ile Asn Phe Glu Lys Leu
1 5

<210> SEQ ID NO 14
<211> LENGTH: 9
<212> TYPE: PRT
<213> ORGANISM: Influenza A virus

<400> SEQUENCE: 14

Gly Ile Leu Gly Phe Val Phe Thr Leu
1 5

<210> SEQ ID NO 15
<211> LENGTH: 9
<212> TYPE: PRT
<213> ORGANISM: Influenza A virus

<400> SEQUENCE: 15

Gly Pro Pro Gln Trp Asn Asn Pro Pro
1 5

<210> SEQ ID NO 16
<211> LENGTH: 8
<212> TYPE: PRT
<213> ORGANISM: Artificial Sequence
<220> FEATURE:
<223> OTHER INFORMATION: Synethtic construct
<220> FEATURE:
<221> NAME/KEY: MISC_FEATURE
<222> LOCATION: (3)..(3)
<223> OTHER INFORMATION: X is leucine (Leu) or Isoleucine (Ile)

<400> SEQUENCE: 16

Asp Tyr Xaa Asp Asp Asp Asp Lys
1 5

<210> SEQ ID NO 17
<211> LENGTH: 9
<212> TYPE: PRT
<213> ORGANISM: Artificial Sequence
<220> FEATURE:
<223> OTHER INFORMATION: Synthetic construct

<400> SEQUENCE: 17

Tyr Pro Tyr Asp Val Pro Asp Tyr Ala
1 5